(12) United States Patent
Bolli et al.

(10) Patent No.: US 12,312,362 B2
(45) Date of Patent: May 27, 2025

(54) SPIRO DERIVATIVES OF ALPHA-D-GALACTOPYRANOSIDES

(71) Applicant: Idorsia Pharmaceuticals Ltd, Allschwil (CH)

(72) Inventors: Martin Bolli, Allschwil (CH); John Gatfield, Allschwil (CH); Corinna Grisostomi, Allschwil (CH); Lubos Remen, Allschwil (CH); Christoph Sager, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 97 days.

(21) Appl. No.: 18/248,007

(22) PCT Filed: Oct. 5, 2021

(86) PCT No.: PCT/EP2021/077381
§ 371 (c)(1),
(2) Date: Apr. 5, 2023

(87) PCT Pub. No.: WO2022/073969
PCT Pub. Date: Apr. 14, 2022

(65) Prior Publication Data
US 2023/0295182 A1 Sep. 21, 2023

(30) Foreign Application Priority Data
Oct. 6, 2020 (WO) ............... PCT/EP2020/077968

(51) Int. Cl.
*C07H 19/12* (2006.01)
*C07D 413/14* (2006.01)
*C07D 498/10* (2006.01)

(52) U.S. Cl.
CPC ......... *C07D 498/10* (2013.01); *C07D 413/14* (2013.01); *C07H 19/12* (2013.01)

(58) Field of Classification Search
None
See application file for complete search history.

(56) References Cited

U.S. PATENT DOCUMENTS

| | | |
|---|---|---|
| 2014/0099319 A1 | 4/2014 | Traber |
| 2022/0281855 A1 | 9/2022 | Bolli et al. |
| 2022/0306674 A1 | 9/2022 | Bolli et al. |
| 2022/0315619 A1 | 10/2022 | Bolli et al. |
| 2022/0324847 A1 | 10/2022 | Bolli et al. |
| 2023/0348442 A1 | 11/2023 | Bolli et al. |
| 2024/0109930 A1 | 4/2024 | Bolli et al. |
| 2024/0124427 A1 | 4/2024 | Bolli et al. |

FOREIGN PATENT DOCUMENTS

| | | | |
|---|---|---|---|
| WO | WO 2002/057284 A1 | 7/2002 | |
| WO | WO 2005/113568 A1 | 12/2005 | |
| WO | WO 2005/113569 A1 | 12/2005 | |
| WO | WO 2014/067986 A1 | 5/2014 | |
| WO | WO 2014/078655 A1 | 5/2014 | |
| WO | WO-2016120403 A1 * | 8/2016 | ......... A61K 31/7056 |
| WO | WO 2017/007689 A1 | 1/2017 | |
| WO | WO 2018/011094 A1 | 1/2018 | |
| WO | WO 2018/209255 A1 | 11/2018 | |
| WO | WO 2018/209276 A1 | 11/2018 | |
| WO | WO 2019/067702 A1 | 4/2019 | |
| WO | WO 2019/075045 A1 | 4/2019 | |
| WO | WO 2019/089080 A1 | 5/2019 | |
| WO | WO 2020/078807 A1 | 4/2020 | |
| WO | WO 2020/078808 A1 | 4/2020 | |
| WO | WO 2020/104335 A1 | 5/2020 | |
| WO | WO 2020/210308 A1 | 10/2020 | |
| WO | WO 2021/001528 A1 | 1/2021 | |
| WO | WO 2021/004940 A1 | 1/2021 | |
| WO | WO 2021/028323 A1 | 2/2021 | |
| WO | WO 2021/028336 A1 | 2/2021 | |

(Continued)

OTHER PUBLICATIONS

U.S. Appl. No. 18/251,273, filed May 1, 2023, Bolli et al.
U.S. Appl. No. 18/264,751, filed Aug. 8, 2023, Bolli et al.
U.S. Appl. No. 18/548,833, filed Sep. 1, 2023, Bolli et al.
U.S. Appl. No. 17/633,895, filed Feb. 8, 2022, Bolli et al.
U.S. Appl. No. 17/633,941, filed Feb. 8, 2022, Bolli et al.
U.S. Appl. No. 17/634,512, filed Feb. 10, 2022, Bolli et al.
U.S. Appl. No. 17/638,799, filed Feb. 25, 2022, Bolli et al.
Arciniegas, E. et al., "Galectin-1 and Galectin-3 and Their Potential Binding Partners in the Dermal Thickening of Keloid Tissues," The American Journal of Dermatopathology, 2019, 41 (3), 193-204.

(Continued)

*Primary Examiner* — Traviss C McIntosh, III
(74) *Attorney, Agent, or Firm* — Hoxie & Associates LLC

(57) ABSTRACT

The present invention relates to compounds of Formula (I)

Formula (I)

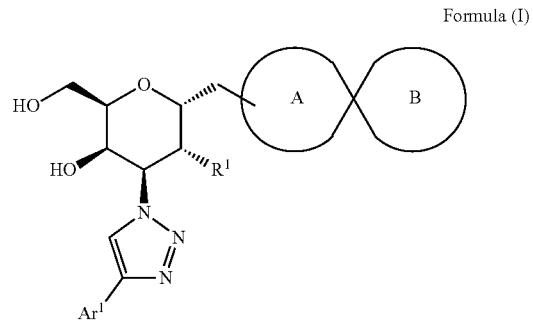

wherein $Ar^1$, A, B, and $R^1$ are as described in the description, their preparation, to pharmaceutically acceptable salts thereof, and to their use as pharmaceuticals, to pharmaceutical compositions containing one or more compounds of Formula (I), and especially to their use as Galectin-3 inhibitors.

18 Claims, No Drawings

(56) References Cited

FOREIGN PATENT DOCUMENTS

| WO | WO 2021/028570 A1 | 2/2021 |
|---|---|---|
| WO | WO 2021/038068 A1 | 3/2021 |
| WO | WO 2022/090544 A1 | 5/2022 |
| WO | WO 2022/171594 A1 | 8/2022 |
| WO | WO 2022/184755 A1 | 9/2022 |

OTHER PUBLICATIONS

Barondes, S. et al., "Galectins: A Family of Animal ß-Galactoside-Binding Lectins," Cell, 1994, 76, 597-598.

Burguillos, M. et al., "Macroglia-Secreted Galectin-3 Acts as a Toll-like Receptor 4 Ligand and Contributes to Microglial Activation," Cell Reports, 2015, 10, 1626-1638.

Caniglia, J. et al., "A potential role for Galectin-3 inhibitors in the treatment of COVID-19," PeerJ, 2020, 8:e9392, 10 pages, doi: 10.7717/peerj.9392.

Chen, W-S. et al., "Galectin-3 Inhibition by a Small-Molecule Inhibitor Reduces both Pathological Corneal Neovascularization and Fibrosis," Investigative Ophthalmology & Visual Science, 2017, 58 (1), 9-20.

Chen, Y-J. et al., "Galectin-3 Enhances Avian H5N1 Influenza A Virus-Induced Pulmonary Inflammation by Promoting NLRP3 Inflammasome Activation," The American Journal of Pathology, 2018, 188 (4), 1031-1042.

Chiariotti, L. et al., "Galectin genes: Regulation of expression," Glycoconjugate Journal, 2004, 19, 441-449.

Dang, Z. et al., "Tubular Atrophy and Interstitial Fibrosis After Renal Transplantation Is Dependent on Galectin-3," Transplantation, 2012, 93 (5), 477-484.

Deroo, E. et al., "The role of galectin-3 and galectin-3-binding protein in venous thrombosis," Blood, 2015, 125 (11), 1813-1821.

Falcone, C. et al., "Galectin-3 Plasma Levels and Coronary Artery Disease: A New Possible Biomarker of Acute Coronary Syndrome," International Journal of Immunopathology and Pharmacology, 2011, 24 (4), 905-913.

Farhad, M. et al., "The role of Galectin-3 in modulating tumor growth and immunosuppression within the tumor microenvironment," OncoImmunology, 2018, 7 (6), e1434467, 8 pages, https://doi.org/10.1080/2162402X.2018.1434467.

Galectin Therapeutics, "Combination Immunotherapy with Galectin-3 Inhibitor GR-MD-02 Enhances Effects in Pre-clinical Models and Early Results of Phase 1 Clinical Trials," Press Release, dated 2017, 3 pages.

Galectin Therapeutics, "Galectin Therapeutics Announces Results from Phase 2b NASH-CX Trial," Bloomberg, Press Release, dated 2017, 5 pages.

Galecto Biotech, "Galecto Biotech's Lead Molecule TD139 is Safe, Well Tolerated, with Direct Target Engagement and Biomarker Effects in a Clinical Phase Ib/IIa trial in IPF Patients," Press Release, dated 2017, 4 pages.

Gao, P. et al., "Galectin-3: its role in asthma and potential as an anti-inflammatory target," Respiratory Research, 2013, 14:136, 9 pages, doi: 10.1186/1465-9921-14-136.

Gehlken, C. et al., "Galectin-3 in Heart Failure: An Update of the Last 3 Years," Heart Failure Clinics, 2018, 14, 75-92.

Greene, T. et al., Eds., Protective Groups in Organic Synthesis, Wiley-Interscience, 1999.

Guha, P. et al., "Cod glycopeptide with picomolar affinity to galectin-3 suppresses T-cell apoptosis and prostate cancer metastasis," Proceedings of the National Academy of Sciences, 2013, 110 (13), 5052-5057.

Henderson, N. et al., "Galectin-3 regulates myofibroblast activation and hepatic fibrosis," Proceedings of the National Academy of Sciences, 2006, 103 (13), 5060-5065.

Henderson, N. et al., "Galectin-3 Expression and Secretion Links Macrophages to the Promotion of Renal Fibrosis," The American Journal of Pathology, 2008, 172 (2), 288-298.

Henderson, N. et al., "The regulation of inflammation by galectin-3," Immunological Reviews, 2009, 230, 160-171.

Hsu, D. et al., " Galectin-3 Expression is Induced in Cirrhotic Liver and Hepatocellular Carcinoma," International Journal of Cancer, 1999, 81, 519-526.

Jin, Q-h. et al., "Serum galectin-3: a risk factor for vascular complications in type 2 diabetes mellitus," Chinese Medical Journal, 2013, 126 (11), 2109-2115.

Johannes, L. et al., "Galectins at a glance," Journal of Cell Science, 2018, 131, jcs208884, 9 pages, doi:10.1242/jcs.208884.

Kikuchi, Y. et al., "Galectin-3-positive call infiltration in human diabetic nephropathy," Nephrology Dialysis Transplantation, 2004, 19 (3), 602-607.

Lacina, L. et al., "Glycophenotype of Psoriatic Skin," Folia Biologica (Praha), 2006, 52, 10-15.

Leffler, H. et al., "Introduction to galectins," Glycoconjugate Journal, 2004, 19, 433-440.

Li, P. et al., "Hematopoietic-derived Galectin-3 Causes Cellular and Systemic Insulin Resistance," HHS Public Access, Author manuscript, available in PMC 2017, 22 pages, face of article states: Published in final edited form as: Cell, 2016, 167(4), 973-984, doi:10.1016/j.cell.2016.10.025.

Liu, F-T. et al., "Galectins in acute and chronic inflammation," Annals of the New York Academy of Sciences, 2012, 1253, 80-91.

Lowary, T. et al., "Recognition of synthetic O-methyl, epimeric, and amino analogues of the acceptor $\alpha$-L-Fuc p-(1 $\dashrightarrow$ 2)-$\beta$-D-Gal p-OR by the blood-group A and B gene-specified glycosyltransferases," Carbohydrate Research, 1994, 251, 33-67.

Mackinnon, A. et al., "Regulation of Transforming Growth Factor-$\beta$1-driven Lung Fibrosis by Galectin-3," American Journal of Respiratory and Critical Care Medicine, 2012, 185 (5), 537-546.

Nachtigal, M. et al., "Galectin-3 Expression in Human Atherosclerotic Lesions," American Journal of Pathology, 1998, 152 (5), 1199-1208.

Nishi, Y. et al., "Role of Galectin-3 in Human Pulmonary Fibrosis," Allergology International, 2007, 56 (1), 57-65.

Noël, J-C. et al., "Galectin-3 is Overexpressed in Various Forms of Endometriosis," Applied Immunohistochemistry & Molecular Morphology, 2011, 19 (3), 253-257.

Rao, S. et al., "Regulation of Eosinophil Recruitment and Activation by Galectins in Allergic Asthma," Frontiers in Medicine, 2017, 4:68, 12 pages, doi:10.3389/fmed.2017.00068.

Rebholz, C. et al., "Plasma galectin-3 levels are associated with the risk of incident chronic kidney disease," Kidney International, 2018, 93, 252-259.

Remington, The Science and Practice of Pharmacy, 21st Edition, 2005, Part 5, "Pharmaceutical Manufacturing," published by Lippincott Williams & Wilkins.

Ruvolo, P., "Galectin 3 as a guardian of the tumor microenvironment," Biochimica et Biophysica Acta, 2016, 1863, 427-437.

Saegusa J. et al., "Galectin-3 Is Critical for the Development of the Allergic Inflammatory Response in a Mouse Model of Atopic Dermatitis," The American Journal of Pathology, 2009, 174 (3), 922-931.

Sano, H. et al., "Human Galectin-3 Is a Novel Chemoattractant for Monocytes and Macrophages," The Journal of Immunology, 2000, 165 (4), 2156-2164.

Sciacchitano, S. et al., "Galectin-3: One Molecule for an Alphabet of Diseases, from A to Z," International Journal of Molecular Sciences, 2018, 19, 379, 59 pages, doi:10.3390/ijms19020379.

Sharma, U. et al., "Novel anti-inflammatory mechanisms of N-Acetyl-Ser-Asp-Lys-Pro in hypertension-induced target organ damage," HHS Public Access, Author manuscript, available in PMC 2019, 17 pages, face of article states: Published in final edited form as: Am J Physiol Heart Circ Physiol., 2008, 294(3): H1226-H1232, doi:10.1152/ajpheart.00305.2007.

Stahl, P. et al., Eds., Handbook of Pharmaceutical Salts, Properties, Selection, and Use, Wiley-VCH, 2008.

Sundblad, V. et al., "Regulated expression of galectin-3, a multifunctional glycan-binding protein, in haematopoietic and non-haematopoietic tissues," Histology and Histopathology, 2011, 26, 247-265.

(56) References Cited

OTHER PUBLICATIONS

Taniguchi, T. et al., "Serum Levels of Galectin-3: Possible Association with Fibrosis, Aberrant Angiogenesis, and Immune Activation in Patients with Systemic Sclerosis," Journal of Rheumatology, 2012, 39 (3), 539-544.

Thandavarayan, R. et al., "14-3-3 protein regulates Ask1 signaling and protects against diabetic cardiomyopathy," Biochemical Pharmacology, 2008, 75, 1797-1806.

Vuong, L. et al., "An Orally Active Galectin-3 Antagonist Inhibits Lung Adenocarcinoma Growth and Augments Response to PD-L1 Blockade," Cancer Research, 2019, 79 (7), 1480-1492.

Wouters, J. et al., Eds., Pharmaceutical Salts and Co-crystals, RSC Publishing, 2012.

Zhong, X. et al., "The role of galectin-3 in heart failure and cardiovascular disease," Clinical and Experimental Pharmacology and Physiology, 2019, 46, 197-203.

\* cited by examiner

SPIRO DERIVATIVES OF ALPHA-D-GALACTOPYRANOSIDES

CROSS REFERENCE TO RELATED APPLICATIONS

This application is a National Stage Entry under 35 U.S.C. § 371 of International Application No. PCT/EP2021/077381 filed Oct. 5, 2021, which claims priority to International Application No. PCT/EP2020/077968 filed Oct. 6, 2020, the contents of each of which are hereby incorporated by reference in their entireties.

The present invention relates to compounds of formula (I) which are galectin-3 inhibitors and their use in the prevention/prophylaxis or treatment of diseases and disorders that are related to galectin-3 binding to natural ligands. The invention also concerns related aspects including processes for the preparation of the compounds, pharmaceutical compositions containing one or more compounds of formula (I), and their medical use as Galectin-3 inhibitors. The compounds of formula (I)) may especially be used as single agents or in combination with one or more therapeutic agents.

Galectins are defined as a protein family based on conserved β-galactoside-binding sites found within their characteristic ~130 amino acid (aa) carbohydrate recognition domains (CRDs) (Barondes S H et al., Cell 1994; 76, 597-598). Human, mouse and rat genome sequences reveal the existence of at least 16 conserved galectins and galectin-like proteins in one mammalian genome (Leffler H. et al., Glycoconj. J. 2002, 19, 433-440). So far, three galectin subclasses were identified, the prototypical galectins containing one carbohydrate-recognition domain (CRD); the chimaera galectin consisting of unusual tandem repeats of proline- and glycine-rich short stretches fused onto the CRD; and the tandem-repeat-type galectins, containing two distinct CRDs in tandem connected by a linker (Zhong X., Clin Exp Pharmacol Physiol. 2019; 46:197-203). As galectins can bind either bivalently or multivalently, they can e.g. cross-link cell surface glycoconjugates to trigger cellular signaling events. Through this mechanism, galectins modulate a wide variety of biological processes (Sundblad V. et al., Histol Histopathol 2011; 26: 247-265).

Galectin-3 (Gal-3), the only chimaera type in the galectin family, has a molecular weight of 32-35 kDa and consists of 250 amino acid residues in humans, a highly conserved CRD and an atypical N-terminal domain (ND). Galectin-3 is monomeric up to high concentrations (100 μM), but can aggregate with ligands at much lower concentrations, which is promoted by its N-terminal non-CRD region via an oligomerisation mechanism that is not yet completely understood (Johannes, L. et al., Journal of Cell Science 2018; 131, jcs208884).

Gal-3 is widely distributed in the body, but the expression level varies among different organs. Depending on its extracellular or intracellular localization, it can display a broad diversity of biological functions, including immunomodulation, host-pathogen interactions, angiogenesis, cell migration, wound healing and apoptosis (Sundblad V. et al., Histol Histopathol 2011; 26: 247-265). Gal-3 is highly expressed in many human tumours and cell types, such as myeloid cells, inflammatory cells (macrophages, mast cells, neutrophils, T cells, eosinophils, etc.), fibroblasts and cardiomyocytes (Zhong X. et al., Clin Exp Pharmacol Physiol. 2019; 46:197-203), indicating that Gal-3 is involved in the regulation of inflammatory and fibrotic processes (Henderson N C. Et al., Immunological Reviews 2009; 230: 160-171; Sano H. et al., J Immunol. 2000; 165(4):2156-64). Furthermore, Gal-3 protein expression levels are up-regulated under certain pathological conditions, such as neoplasms and inflammation (Chiariotti L. et al., Glycoconjugate Journal 2004 19, 441-449; Farhad M. et al., Oncolmmunology 2018, 7:6, e1434467).

There are multiple lines of evidence supporting functional involvement of Gal-3 in the development of inflammatory/autoimmune diseases, such as asthma (Gao P. et al. Respir Res. 2013, 14:136; Rao S P et al. Front Med (Lausanne) 2017; 4:68), rheumatoid arthritis, multiple sclerosis, diabetes, plaque psoriasis (Lacina L. et al. Folia Biol (Praha) 2006; 52(1-2):10-5) atopic dermatitis (Saegusa J. et al. Am J Pathol. 2009, 174(3):922-31), endometriosis (Noel J C et al. Appl Immunohistochem Mol Morphol. 2011 19(3):253-7), or viral encephalitis (Liu F T et al., Ann N Y Acad Sci. 2012; 1253:80-91; Henderson N C, et al., Immunol Rev. 2009; 230(1):160-71; Li P et al., Cell 2016; 167:973-984). Recently Gal-3 has emerged as a key player of chronic inflammation and organ fibrogenesis development e.g. liver (Henderson N C et al., PNAS 2006; 103: 5060-5065; Hsu D K et al. Int J Cancer. 1999, 81(4):519-26), kidney (Henderson N C et al., Am. J. Pathol. 2008; 172:288-298; Dang Z. et al. Transplantation. 2012, 93(5):477-84), lung (Mackinnon A C et al., Am. J. Respir. Crit. Care Med 2012, 185: 537-546; Nishi Y. et al. Allergol Int. 2007, 56(1):57-65), heart (Thandavarayan R A et al. Biochem Pharmacol. 2008, 75(9):1797-806; Sharma U. et al. Am J Physiol Heart Circ Physiol. 2008; 294(3):H1226-32), as well as the nervous system (Burguillos M A et al. Cell Rep. 2015, 10(9):1626-1638), and in corneal neovascularization (Chen W S. Et al., Investigative Ophthalmology & Visual Science 2017, Vol. 58, 9-20). Additionally, Gal-3 was found to be associated with dermal thickening of keloid tissues (Arciniegas E. et al., The American Journal of dermatopathology 2019; 41(3): 193-204) and systemic sclerosis (SSc) especially with skin fibrosis and proliferative vasculopathy observed in such condition (Taniguchi T. et al. J Rheumatol. 2012, 39(3):539-44). Gal-3 was found to be up-regulated in patient suffering chronic kidney disease (CKD) associated-kidney failure, and especially in those affected by diabetes. Interestingly, data obtained from this patient population showed correlation between Gal-3 upregulation in glomeruli and the observed urinary protein excretion (Kikuchi Y. et al. Nephrol Dial Transplant. 2004, 19(3):602-7). Additionally, a recent prospective study from 2018 demonstrated that higher Gal-3 plasma levels are associated with an elevated risk of developing incident CKD, particularly among hypertension-suffering population (Rebholz C M. et al. Kidney Int. 2018 January; 93(1): 252-259). Gal-3 is highly elevated in cardiovascular diseases (Zhong X. et al. Clin Exp Pharmacol Physiol. 2019, 46(3):197-203), such as atherosclerosis (Nachtigal M. et al. Am J Pathol. 1998; 152(5):1199-208), coronary artery disease (Falcone C. et al. Int J Immunopathol Pharmacol 2011, 24(4):905-13), heart failure and thrombosis (Nachtigal M. et al., Am J Pathol. 1998; 152(5): 1199-208; Gehlken C. et al., Heart Fail Clin. 2018, 14(1): 75-92; DeRoo E P. et al., Blood. 2015, 125(11):1813-21). Gal-3 blood concentration is elevated in obese and diabetic patients and is associated with a higher risk for micro- and macro-vascular complication (such as heart failure, nephropathy/retinopathy, peripheral arterial disease, cerebrovascular event, or myocardial infarction) (Qi-hui-Jin et al. Chin Med J (Engl). 2013,126(11):2109-15). Gal-3 influences oncogenesis, cancer progression, and metastasis (Vuong L. et al., Cancer Res 2019 (79) (7) 1480-1492), and was shown to exert a role as a pro-tumor factor by acting within the micro tumor environment to suppress immune surveillance (Ruvolo P P. et al. Biochim Biophys Acta. 2016 March, 1863(3):427-437; Farhad M. et al. Oncoimmunology 2018 Feb. 20; 7(6):e1434467). Among the cancers that express high level of Gal-3 are found those affecting the thyroid gland, the central nervous system, the tongue, the breast, the gastric cancer, the head and neck squamous cell, the pancreas, the bladder, the kidney, the liver, the parathyroid, the salivary glands, but also lymphoma, carcinoma, non-small cell lung cancer, melanoma and neuroblastoma (Sciacchitano S. et al. Int J Mol Sci 2018 Jan. 26, 19(2):379).

Also, Gal-3 inhibition has been proposed to be beneficial in the treatment of COVID-19 (Caniglia J L et al. PeerJ 2020, 8:e9392) and influenza H5N1 (Chen Y J et al. Am. J. Pathol. 2018, 188(4), 1031-1042) possibly due to anti-inflammatory effects.

Recently, Gal-3 inhibitors have shown to have positive effects when used in combination immunotherapy (Galectin Therapeutics. Press Release, Feb. 7, 2017) and idiopathic pulmonary fibrosis (Galecto Biotech. Press Release, Mar. 10, 2017) and in NASH cirrhosis (Dec. 5, 2017). WO20180209276, WO2018209255 and WO2019089080 disclose compounds having binding affinity with galectin proteins for the treatment of systemic insulin resistance disorders. Thus, Gal-3 inhibitors, alone or in combination with other therapies, may be useful for the prevention or treatment of diseases or disorders such as fibrosis of organs, cardiovascular diseases and disorders, acute kidney injury and chronic kidney disease, liver diseases and disorders, interstitial lung diseases and disorders, ocular diseases and disorders, cell proliferative diseases and cancers, inflammatory and autoimmune diseases and disorders, gastrointestinal tract diseases and disorders, pancreatic diseases and disorders, abnormal angiogenesis-associated diseases and disorders, brain-associated diseases and disorders, neuropathic pain and peripheral neuropathy, and/or transplant rejection.

Several publications and patent applications describe synthetic inhibitors of Gal-3 that are being explored as antifibrotic agents (see for example WO2005113568, WO2005113569, WO2014067986, WO2016120403, US20140099319, WO2019067702, WO2019075045, WO2014078655, WO2020078807 and WO2020078808). WO2002057284, WO2005113569, and WO2014078655 disclose a broad generic scope of beta-configured galectin inhibitors. WO2016120403, WO2020104335, WO2021001528, WO2021038068 and WO2021004940 disclose a broad generic scope of alpha-D-galactoside inhibitors of galectins.

The present invention provides novel compounds of Formula (I) which are alpha-configured galectin-3 inhibitors. The present compounds may, thus, be useful for the prevention/prophylaxis or treatment of diseases and disorders where modulation of Gal-3 binding to its natural carbohydrate ligands is indicated.

1) In a first embodiment, the invention relates to a compound of the Formula (I),

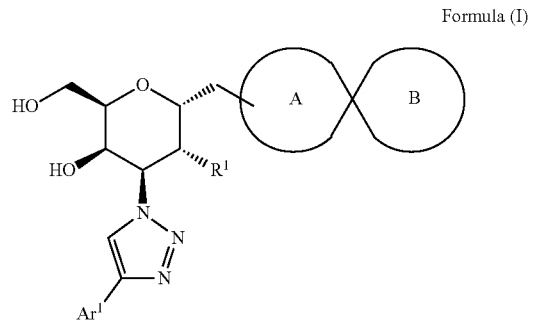

Formula (I)

wherein
$Ar^1$ represents
aryl (especially phenyl) which is unsubstituted, or mono-, di-, tri-, tetra-, or penta-substituted (especially di-, or tri-substituted), wherein the substituents are independently selected from halogen, methyl, cyano, methoxy, trifluoromethyl, and trifluoromethoxy;
[in a sub-embodiment said aryl is phenyl which is di-, or tri-substituted wherein at least one of said substituents is attached in a meta- or in para-position of said phenyl; wherein in particular, if present, such substituent in para-position is selected from halogen and methyl];
5- or 6-membered heteroaryl, wherein said 5- or 6-membered heteroaryl independently is unsubstituted, mono- or di-substituted, wherein the substituents are independently selected from halogen, methyl, cyano, and methoxy; or
9- or 10-membered heteroaryl, wherein said 9- or 10-membered heteroaryl independently is unsubstituted, or mono-substituted with methyl;
$R^1$ represents
hydroxy;
$C_{1-4}$-alkoxy (especially methoxy);
O—CO—$C_{1-3}$-alkyl;
O—CO—NH—$R^{N11}$ wherein $R^{N11}$ represents hydrogen or $C_{1-3}$-alkyl;
—O—CH$_2$—$C_1$-fluoroalkyl; or
—O—CH$_2$—CO—$R^{LX}$ wherein $R^{LX}$ represents
hydroxy;
$C_{1-3}$-alkoxy (especially methoxy);
morpholin-4-yl; or
—$NR^{N21}R^{N22}$ wherein $R^{N21}$ and $R^{N22}$ both independently represent hydrogen or methyl; and

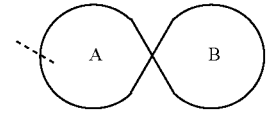

represents a spirocyclic fragment, wherein:
ring A represents a heterocycloalkylene selected from

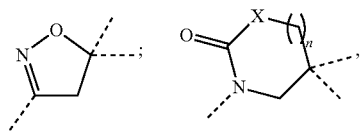

wherein X represents nitrogen or oxygen, and n represents the integer 0 or 1 (especially X represents nitrogen and n represents the integer 0 or 1; or X represents oxygen and n represents the integer 0); and wherein in case X represents nitrogen, said nitrogen is unsubstituted or mono-substituted with $C_{1-4}$-alkyl (especially said nitrogen is unsubstituted);
and

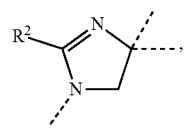

wherein R² represents hydrogen or $C_{1-4}$-alkyl (especially methyl); and ring B represents $C_{4-7}$-cycloalkane-diyl wherein said $C_{4-7}$-cycloalkane-diyl is unsubstituted, mono-, or di-substituted wherein the substituents are independently selected from $C_{1-4}$-alkyl (especially methyl, isopropyl); $C_{1-3}$-fluoroalkyl; $C_{1-4}$-alkoxy; halogen (especially fluoro); cyano; oxo; hydroxy; hydroxy-$C_{1-4}$-alkyl (especially 2-hydroxy-prop-2-yl); hydroxyimino; morpholin-4-yl; and —NH—$R^{N11}$ wherein $R^{N11}$ represents $C_{1-6}$-alkyl (especially isopropyl or pent-3-yl), $C_{2-4}$-alkoxy, $C_{3-6}$-cycloalkyl (especially cyclopropyl), $C_{2-3}$-fluoroalkyl (especially 2,2-difluoroethyl or 2,2,2-trifluoroethyl), —CO—$C_{1-4}$-alkyl, or —CO—$C_{1-4}$-alkoxy;

4- to 7-membered heterocycloalkane-diyl wherein said heterocycloalkane-diyl contains one ring oxygen atom; or 4- to 7-membered heterocycloalkane-diyl wherein said heterocycloalkane-diyl contains one ring nitrogen atom, wherein said ring nitrogen atom is unsubstituted or mono-substituted with $C_{1-4}$-alkyl (especially methyl), —CO—$C_{1-4}$-alkyl, —$SO_2$—$C_{1-4}$-alkyl, —CO—$C_{1-4}$-alkoxy, or —CO—NH—$C_{1-4}$-alkyl; and wherein said 4- to 7-membered heterocycloalkane-diyl carries no further substituent in addition to said substituent on the ring nitrogen atom, or carries one further substituent on a ring carbon atom that is attached to said ring nitrogen atom wherein said substituent is oxo, or —CO—OH;

or, in addition, ring B represents bridged bicyclic $C_{6-9}$-cycloalkane-diyl (especially bicyclo[2,2,1]heptane-2,2-diyl or bicyclo[3,2,1]-octane-3,3-diyl).

In a sub-embodiment of embodiment 1), ring B represents bridged bicyclic $C_{6-9}$-cycloalkane-diyl (especially bicyclo[2,2,1]heptane-2,2-diyl or bicyclo[3,2,1]-octane-3,3-diyl).

In another sub-embodiment of embodiment 1), ring B is different from bridged bicyclic $C_{6-9}$-cycloalkane-diyl.

The compounds of Formula (I) contain five stereogenic or asymmetric centers, which are situated on the tetrahydropyran moiety and which are in the absolute configuration as drawn for Formula (I). In addition, the compounds of Formula (I) may contain one, and possibly more, further stereogenic or asymmetric centers, such as one or more additional asymmetric carbon atoms. The compounds of Formula (I) may thus be present as mixtures of stereoisomers or preferably as pure stereoisomers. Mixtures of stereoisomers may be separated in a manner known to a person skilled in the art.

In case a particular compound (or generic structure) is designated as being in a certain absolute configuration, e.g. as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center.

In case a particular compound contains (in addition to the tetrahydropyran moiety) one or more stereogenic or asymmetric centers, wherein said one (or more) of said stereogenic or asymmetric center(s) is/are not explicitly designated as (R)- or (S)-, it is understood that said stereogenic or asymmetric center(s) independently may be in (R)- or (S)-configuration. Such compound name is understood to encompass the compound where such center is in (R)- or (S)-configuration, or any mixture of epimers with regard to such center. Likewise, in case such stereogenic or asymmetric center is designated as being in (RS)-configuration, this means that such stereogenic or asymmetric center in such compound may be present in (R)-configuration, in (S)-configuration, or in any mixture of epimers with regard to such center. In case two or more such stereogenic or asymmetric centers (in undesignated or designated (RS)-configuration) are present in one molecule, it is understood that, if not explicitly defined otherwise, the order of absolute configuration does not indicate any defined relative configuration with regard to the two or more centers. It is understood that explicitly designated (R)- or (S)-configuration(s) and undesignated or designated (RS)-configuration(s), can co-exist in one and the same molecule and are to be interpreted accordingly.

In case for certain compounds wherein ring B represents "$C_{4-7}$-cycloalkane-diyl wherein said $C_{4-7}$-cycloalkane-diyl is mono- or di-substituted", the stereogenic centers on said $C_{4-7}$-cycloalkane-diyl are not specifically assigned, this means that such stereogenic centers may be present in (r,R)- or (s,S)-configuration, or in any mixture thereof. For example, the compound "tert-butyl (3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate" encompasses diastereoisomerically enriched, especially essentially pure, "tert-butyl ((5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate", diastereoisomerically enriched, especially essentially pure, "tert-butyl ((5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate", or any mixture of said diastereomers.

In this patent application, a bond drawn as a dotted line, or interrupted by a wavy line, shows the point of attachment of the radical drawn. For example, the radicals drawn below

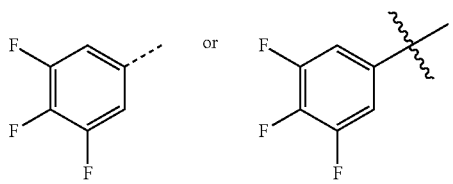

describe a 3,4,5-trifluorophenyl group.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2$H (deuterium) labelled compounds of Formula (I) according to embodiments 1) to 17), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Where the plural form is used for compounds, salts, pharmaceutical compositions, diseases and the like, this is intended to mean also a single compound, salt, or the like.

Any reference to compounds of Formula (I) according to embodiments 1) to 17) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of Formula (I), as defined in any one of embodiments 1) to 14), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

In this patent application, the compounds are named using IUPAC nomenclature, but can also be named using carbohydrate nomenclature. Thus, the moiety:

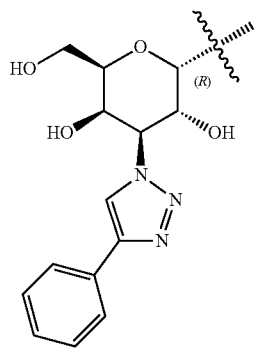

can be named (2R,3R,4R,5R,6R)-3,5-dihydroxy-6-(hydroxymethyl)-4-(4-phenyl-1H-1,2,3-triazol-1-yl)tetrahydro-2H-pyran-2-yl or, alternatively, 1,3-di-deoxy-3-[4-phenyl-1H-1,2,3-triazol-1-yl]-α-D-galactopyranoside-1-yl, wherein the absolute configuration of carbon atom carrying the point of attachment to the rest of the molecule is (2R)-, respectively, alpha. For example, compound (2R,3R,4S,5R,6R)-6-((1-oxa-2-azaspiro[4.5]dec-2-en-3-yl)methyl)-4-(4-(3-chloro-4,5-difluorophenyl)-1H-1,2,3-triazol-1-yl)-2-(hydroxymethyl)-5-methoxytetrahydro-2H-pyran-3-ol is to be understood as also referring to: 1-(1,3-di-deoxy-2-O-methyl-3-[4-(3-chloro-4,5-difluorophenyl)-1H-1,2,3-triazol-1-yl]-α-D-galacto-pyranose)-1(1-oxa-2-azaspiro[4.5]dec-2-en-3-yl)-methane.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined. If not explicitly defined otherwise in the respective embodiment or claim, groups defined herein are unsubstituted.

The term "halogen" means fluorine, chlorine, or bromine, preferably fluorine.

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example, a $C_{1-6}$-alkyl group contains from one to six carbon atoms. Representative examples of alkyl groups are methyl, ethyl, propyl, isopropyl, butyl, isobutyl, tert.-butyl, and pent-3-yl. For avoidance of any doubt, in case a group is referred to as e.g. propyl or butyl, it is meant to be n-propyl, respectively n-butyl. In case $R^2$ represents "$C_{1-4}$-alkyl", the term especially refers to methyl.

The term "hydroxy-$C_{1-4}$-alkyl" refers to a $C_{1-4}$-alkyl group as defined before in which one hydrogen atom has been replaced with hydroxy. An example is 2-hydroxy-prop-2-yl.

The term "—$C_{x-y}$-alkylene-", used alone or in combination, refers to bivalently bound alkyl group as defined before containing x to y carbon atoms. The term "—$C_{0-y}$-alkylene-"

refers to a direct bond, or to a —$(C_{1-y})$alkylene- as defined before. Preferably, the points of attachment of a —$C_{1-y}$-alkylene group are in 1,1-diyl, or in 1,2-diyl, or in 1,3-diyl arrangement. In case a $C_{0-y}$-alkylene group is used in combination with another substituent, the term means that either said substituent is linked through a $C_{1-y}$-alkylene group to the rest of the molecule, or it is directly attached to the rest of the molecule (i.e. a $C_0$-alkylene group represents a direct bond linking said substituent to the rest of the molecule).

The term "fluoroalkyl", used alone or in combination, refers to an alkyl group as defined before containing one to four carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Representative examples of fluoroalkyl groups include trifluoromethyl, difluoromethyl, 2-fluoroethyl, 2,2-difluoroethyl, and 2,2,2-trifluoroethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $C_1$-fluoroalkoxy groups such as trifluoromethoxy and difluoromethoxy.

The term "cycloalkyl", used alone or in combination, refers especially to a saturated monocyclic hydrocarbon ring containing three to seven carbon atoms. The term "$C_{x-y}$-cycloalkyl" (x and y each being an integer), refers to a cycloalkyl group as defined before containing x to y carbon atoms. For example, a $C_{3-6}$-cycloalkyl group contains from three to six carbon atoms. Representative examples of cycloalkyl groups are cyclopropyl, cyclobutyl, cyclopentyl, cyclohexyl, and cycloheptyl. Preferred are cyclopropyl, cyclobutyl, cyclopentyl and cyclohexyl. Said cycloalkyl groups are unsubstituted or substituted as explicitly defined.

The term "—$C_{x-y}$-cycloalkylene-", used alone or in combination, refers to bivalently bound cycloalkyl group as defined before containing x to y carbon atoms. Preferably, the points of attachment of any bivalently bound cycloalkyl group is in 1,1-diyl arrangement. In case ring B represents "$C_{4-7}$-cycloalkane-diyl", the term especially refers to cyclobutane-1,1-diyl, cyclopentane-1,1-diyl, cyclohexane-1,1-diyl, or cycloheptane-1,1-diyl. Said "$C_{4-7}$-cycloalkane-diyl" is unsubstituted or substituted as explicitly defined.

The term "bridged bicyclic $C_{6-9}$-cycloalkane-diyl" refers to a saturated bridged bicyclic hydrocarbon ring system containing six to nine carbon atoms. In case ring B represents "bridged bicyclic $C_{6-9}$-cycloalkane-diyl", the term especially refers to bicyclo[2,2,1]heptane-2,2-diyl or bicyclo[3,2,1]-octane-3,3-diyl.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. Representative examples of alkoxy groups are methoxy, ethoxy, isopropoxy, and tert-butoxy. Examples of $R^1$ representing "$C_{1-4}$-alkoxy" are methoxy and ethoxy; most preferred is methoxy.

The term "heterocycloalkyl", used alone or in combination, and if not explicitly defined in a broader or more narrow way, refers to a saturated or unsaturated non-aromatic monocyclic hydrocarbon ring containing one or two ring heteroatoms independently selected from nitrogen, sulfur, and oxygen (especially one oxygen atom, one sulfur atom, one nitrogen atom, two nitrogen atoms, two oxygen atoms, or one nitrogen atom and one oxygen atom). The term "x- to y-membered heterocycloalkyl" refers to such a heterocycle containing a total of x to y ring atoms.

The term "heterocycloalkylene" used alone or in combination, refers to bivalently bound heterocycloalkyl group as defined before. For avoidance of doubt, in case a certain 4- to 7-membered heterocycloalkane-diyl is defined as containing one ring heteroatom (such as one ring oxygen atom, or one ring nitrogen atom) it is understood that such 4- to 7-membered heterocycloalkane-diyl (e.g. as used for ring B) contains exactly said one ring heteroatom and no further ring heteroatoms. In case ring B represents "4- to 7-membered heterocycloalkane-diyl", it is to be understood that such heterocycloalkane-diyl is bivalently bound to ring A through one ring carbon atom of said heterocycloalkane-diyl. An example of ring B representing "4- to 7-membered heterocycloalkane-diyl containing one ring oxygen atom" is tetrahydro-2H-pyran-4,4-diyl. Examples of ring B representing "4- to 7-membered heterocycloalkane-diyl containing one ring nitrogen atom" are piperidin-4,4-diyl or azepan-4,4-diyl. Said heterocycloalkylene groups are unsubstituted or substituted as explicitly defined.

In case ring A represents the heterocycloalkylene

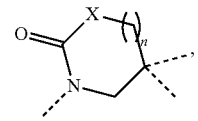

said heterocycloalkylene especially refers to the following structures:

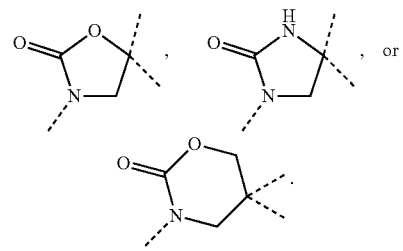

The term "aryl", used alone or in combination, means phenyl or naphthyl, preferably phenyl, wherein said aryl group is unsubstituted or substituted as explicitly defined.

The term "heteroaryl", used alone or in combination, and if not explicitly defined in a broader or more narrow way, means a 5- to 10-membered monocyclic or bicyclic aromatic ring containing one to a maximum of four heteroatoms, each independently selected from oxygen, nitrogen and sulfur. Representative examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

The term "heteroarylene" used alone or in combination, refers to bivalently bound heteroaryl group as defined before.

The term "cyano" refers to a group —CN.

The term "oxo" refers to a group =O which is preferably attached to a chain or ring carbon or sulfur atom as for example in a carbonyl group —(CO)— (or a sulfonyl group —(SO$_2$)—).

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to compounds according to embodiment 1), wherein Ar$^1$ represents phenyl which is di-, or tri-substituted, wherein the substituents are independently selected from halogen, methyl, cyano, methoxy, trifluoromethyl, and trifluoromethoxy (especially halogen or methyl).

In a sub-embodiment at least one of said substituents is attached in a meta- or in para-position of said phenyl.

3) Another embodiment relates to compounds according to embodiment 1), wherein Ar$^1$ represents phenyl which is mono-, di- or tri-substituted, wherein the substituents are independently selected from halogen and methyl.

4) Another embodiment relates to compounds according to embodiment 1), wherein Ar$^1$ represents phenyl which is di- or tri-substituted, wherein the substituents are independently selected from halogen and methyl; wherein at least one of said substituents is attached in a meta- and/or in para-position of said phenyl.

5) Another embodiment relates to compounds according to embodiment 1), wherein Ar$^1$ represents

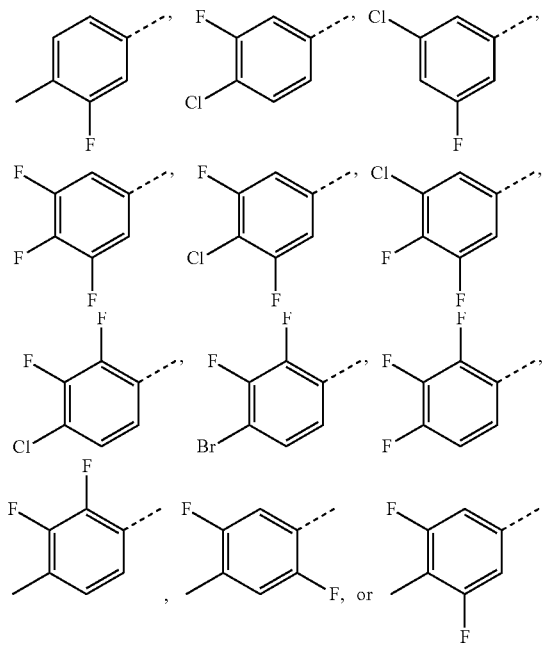

6) Another embodiment relates to compounds according to any one of embodiments 1) to 5), wherein R$^1$ represents
hydroxy;
C$_{1-4}$-alkoxy (especially methoxy);
O—CO—C$_{1-3}$-alkyl;
O—CO—NH—R$^{N11}$ wherein R$^{N11}$ represents hydrogen or C$_{1-3}$-alkyl;
O—CH$_2$—C$_1$-fluoroalkyl; or
—O—CH$_2$—CO—R$^{LX}$ wherein R$^{LX}$ represents
hydroxy; or
C$_{1-3}$-alkoxy (especially methoxy).

7) Another embodiment relates to compounds according to any one of embodiments 1) to 5), wherein R$^1$ represents methoxy.

8) Another embodiment relates to compounds according to any one of embodiments 1) to 7), wherein ring A represents a heterocycloalkylene selected from

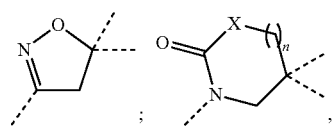

wherein X represents nitrogen or oxygen, and n represents the integer 0 or 1 (especially X represents nitrogen and n represents the integer 0 or 1; or X represents oxygen and n represents the integer 0); wherein in case X represents nitrogen, said nitrogen is unsubstituted; and

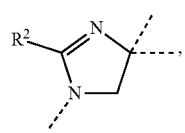

wherein R² represents hydrogen or methyl.
9) Another embodiment relates to compounds according to any one of embodiments 1) to 7), wherein ring A represents the heterocycloalkylene:

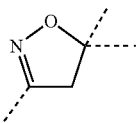

10) Another embodiment relates to compounds according to any one of embodiments 1) to 9), wherein ring B represents
unsubstituted $C_{4-7}$-cycloalkane-diyl;
$C_{4-7}$-cycloalkane-diyl wherein said $C_{4-7}$-cycloalkane-diyl is mono-substituted wherein the substituents are independently selected from $C_{1-4}$-alkyl (especially methyl, isopropyl); halogen (especially fluoro); cyano; oxo; hydroxy; hydroxy-$C_{1-4}$-alkyl (especially 2-hydroxy-prop-2-yl); morpholin-4-yl; and —NH—$R^{N11}$ wherein $R^{N11}$ represents $C_{1-6}$-alkyl (especially isopropyl or pent-3-yl), $C_{2-4}$-alkoxy, $C_{3-6}$-cycloalkyl (especially cyclopropyl), $C_{2-3}$-fluoroalkyl (especially 2,2-difluoroethyl or 2,2,2-trifluoroethyl), —CO—$C_{1-4}$-alkyl, or —CO—$C_{1-4}$-alkoxy;
$C_{4-7}$-cycloalkane-diyl wherein said $C_{4-7}$-cycloalkane-diyl is di-substituted wherein the substituents are independently selected from $C_{1-4}$-alkyl (especially methyl) and halogen (especially fluoro);
4- to 7-membered heterocycloalkane-diyl wherein said heterocycloalkane-diyl contains one ring oxygen atom; or
4- to 7-membered heterocycloalkane-diyl wherein said heterocycloalkane-diyl contains one ring nitrogen atom, wherein said nitrogen atom is unsubstituted or mono-substituted with $C_{1-4}$-alkyl (especially methyl), —CO—$C_{1-4}$-alkyl, —SO$_2$—$C_{1-4}$-alkyl, —CO—$C_{1-4}$-alkoxy, or —CO—NH—$C_{1-4}$-alkyl; and wherein said 4- to 7-membered heterocycloalkane-diyl carries no further substituent in addition to said substituent on the ring nitrogen atom, or carries one further substituent on a ring carbon atom that is attached to said ring nitrogen atom wherein said substituent is oxo.
11) Another embodiment relates to compounds according to any one of embodiments 1) to 9), wherein ring B represents
unsubstituted $C_{4-7}$-cycloalkane-diyl (especially cyclohexane-1,1-diyl or cycloheptane-1,1-diyl);
$C_{4-7}$-cycloalkane-diyl (especially cyclohexane-1,1-diyl) wherein said $C_{4-7}$-cycloalkane-diyl is mono-substituted wherein the substituents are independently selected from $C_{1-4}$-alkyl (especially methyl, isopropyl); cyano; hydroxy; hydroxy-$C_{1-4}$-alkyl (especially 2-hydroxy-prop-2-yl); and —NH—$R^{N11}$ wherein $R^{N11}$ represents $C_{1-6}$-alkyl (especially isopropyl or pent-3-yl), $C_{2-4}$-alkoxy, $C_{3-6}$-cycloalkyl (especially cyclopropyl), $C_{2-3}$-fluoroalkyl (especially 2,2-difluoroethyl or 2,2,2-trifluoroethyl), —CO—$C_{1-4}$-alkyl, or —CO—$C_{1-4}$-alkoxy;
$C_{4-7}$-cycloalkane-diyl (especially cyclohexane-1,1-diyl) wherein said $C_{4-7}$-cycloalkane-diyl is di-substituted wherein the substituents are independently selected from $C_{1-4}$-alkyl (especially methyl) and halogen (especially fluoro);
4- to 7-membered heterocycloalkane-diyl wherein said heterocycloalkane-diyl contains one ring oxygen atom (especially tetrahydropyran-4,4-diyl); or
4- to 7-membered heterocycloalkane-diyl wherein said heterocycloalkane-diyl contains one ring nitrogen atom (especially piperidin-4,4-diyl or azepan-4,4-diyl), wherein said nitrogen atom is unsubstituted or mono-substituted with $C_{1-4}$-alkyl (especially methyl), —CO—$C_{1-4}$-alkoxy, or —CO—NH—$C_{1-4}$-alkyl; and wherein said 4- to 7-membered heterocycloalkane-diyl carries no further substituent in addition to said substituent on the ring nitrogen atom, or carries one further substituent on a ring carbon atom that is attached to said ring nitrogen atom wherein said substituent is oxo.
12) Another embodiment relates to compounds according to any one of embodiments 1) to 9), wherein ring B represents
cyclohexane-1,1-diyl or cycloheptane-1,1-diyl;
cyclohexane-1,1-diyl which is mono-substituted wherein the substituents are selected from $C_{1-4}$-alkyl (especially methyl, isopropyl); cyano; hydroxy; hydroxy-$C_{1-4}$-alkyl (especially 2-hydroxy-prop-2-yl); and —NH—$R^{N11}$ wherein $R^{N11}$ represents cyclopropyl, $C_{2-3}$-fluoroalkyl (especially 2,2-difluoroethyl or 2,2,2-trifluoroethyl), —CO—$C_{1-4}$-alkyl, or —CO—$C_{1-4}$-alkoxy;
cyclohexane-1,1-diyl which is di-substituted wherein the substituents are selected from $C_{1-4}$-alkyl (especially methyl) and halogen (especially fluoro);
tetrahydropyran-4,4-diyl;
piperidin-4,4-diyl, wherein the nitrogen atom of said piperidin-4,4-diyl is mono-substituted with —CO—$C_{1-4}$-alkoxy, or —CO—NH—$C_{1-4}$-alkyl; and wherein said piperidin-4,4-diyl carries no further substituent in addition to said substituent on the ring nitrogen atom; or
azepan-4,4-diyl, wherein the nitrogen atom of said azepan-4,4-diyl is unsubstituted or mono-substituted with $C_{1-4}$-alkyl (especially methyl), or —CO—$C_{1-4}$-alkoxy; and wherein said azepan-4,4-diyl carries no further substituent in addition to said substituent on the ring nitrogen atom, or carries one further substituent on a ring carbon atom that is attached to said ring nitrogen atom wherein said substituent is oxo.
13) Another embodiment relates to compounds according to any one of embodiments 1) to 9), wherein ring B represents
cyclohexane-1,1-diyl;
cyclohexane-1,1-diyl which is mono-substituted wherein the substituents are selected from cyano; hydroxy-$C_{1-4}$-alkyl (especially 2-hydroxy-prop-2-yl); and —NH—$R^{N11}$ wherein $R^{N11}$ represents —CO—$C_{1-4}$-alkyl, or —CO—$C_{1-4}$-alkoxy;
cyclohexane-1,1-diyl which is di-substituted with fluoro; or
tetrahydropyran-4,4-diyl.
14) Another embodiment relates to compounds according to any one of embodiments 1) to 7), wherein

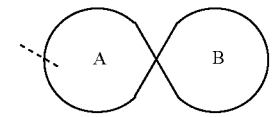

represents a spirocyclic fragment selected from the following groups:

A)

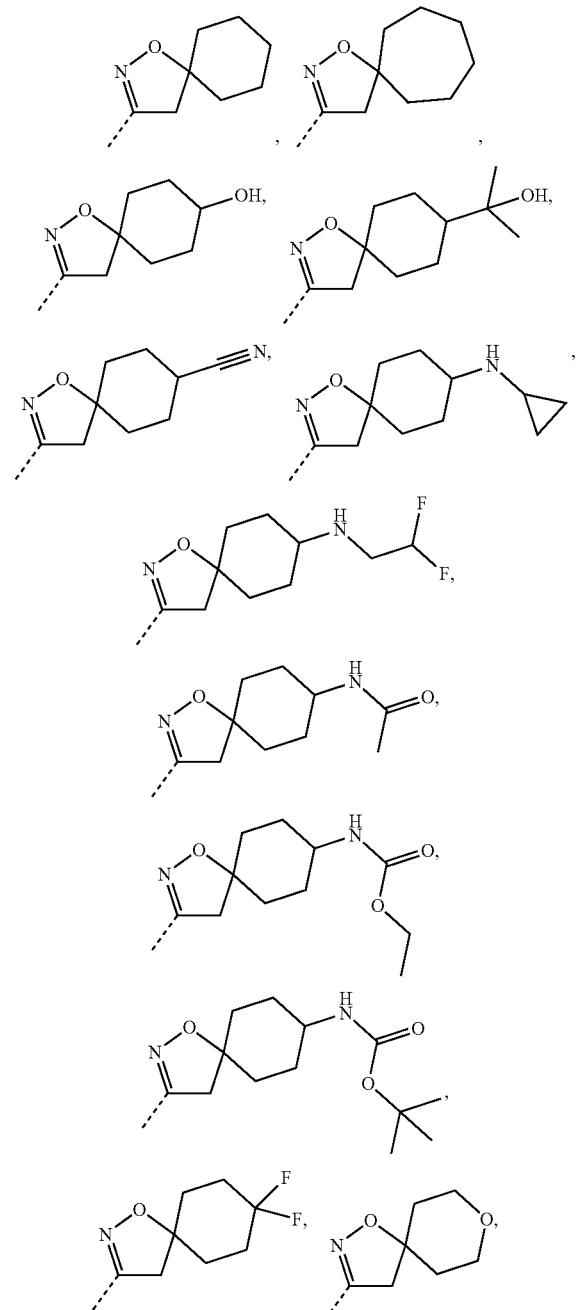

B)

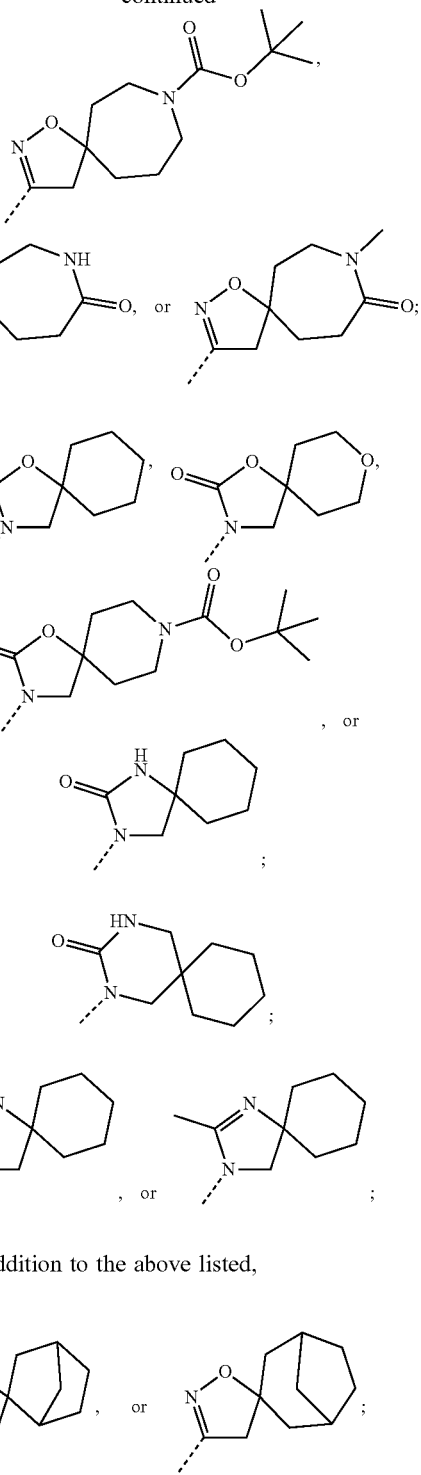

C)

D)

or, in addition to the above listed,

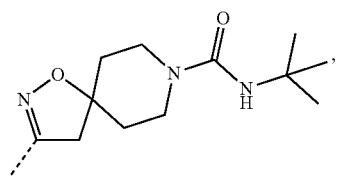

wherein each of the above groups A) to E) represent a particular sub-embodiment, wherein furthermore the above groups A) to D) form a particular sub-embodiment.

15) The invention, thus, relates to compounds of the Formula (I) as defined in embodiment 1), or to such compounds further limited by the characteristics of any one of embodiments 2) to 14), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form: 1, 2+1, 3+1, 4+1, 5+1, 6+1, 6+2+1, 6+3+1, 6+4+1, 6+5+1, 7+1, 7+2+1, 7+3+1, 7+4+1, 7+5+1, 8+1, 8+2+1, 8+3+1, 8+4+1, 8+5+1, 8+6+1, 8+6+2+1, 8+6+3+1, 8+6+4+1, 8+6+5+1, 8+7+1, 8+7+2+1, 8+7+3+1, 8+7+4+1, 8+7+5+1, 9+1, 9+2+1, 9+3+1, 9+4+1, 9+5+1, 9+6+1, 9+6+2+1, 9+6+3+1, 9+6+4+1, 9+6+5+1, 9+7+1, 9+7+2+1, 9+7+3+1, 9+7+4+1, 9+7+5+1, 10+1, 10+2+1, 10+3+1, 10+4+1, 10+5+1, 10+6+1, 10+6+2+1, 10+6+3+1, 10+6+4+1, 10+6+5+1, 10+7+1, 10+7+2+1, 10+7+3+1, 10+7+4+1, 10+7+5+1, 10+8+1, 10+8+2+1, 10+8+3+1, 10+8+4+1, 10+8+5+1, 10+8+6+1, 10+8+6+2+1, 10+8+6+3+1, 10+8+6+4+1, 10+8+6+5+1, 10+8+7+1, 10+8+7+2+1, 10+8+7+3+1, 10+8+7+4+1, 10+8+7+5+1, 10+9+1, 10+9+2+1, 10+9+3+1, 10+9+4+1, 10+9+5+1, 10+9+6+1, 10+9+6+2+1, 10+9+6+3+1, 10+9+6+4+1, 10+9+6+5+1, 10+9+7+1, 10+9+7+2+1, 10+9+7+3+1, 10+9+7+4+1, 10+9+7+5+1, 11+1, 11+2+1, 11+3+1, 11+4+1, 11+5+1, 11+6+1, 11+6+2+1, 11+6+3+1, 11+6+4+1, 11+6+5+1, 11+7+1, 11+7+2+1, 11+7+3+1, 11+7+4+1, 11+7+5+1, 11+8+1, 11+8+2+1, 11+8+3+1, 11+8+4+1, 11+8+5+1, 11+8+6+1, 11+8+6+2+1, 11+8+6+3+1, 11+8+6+4+1, 11+8+6+5+1, 11+8+7+1, 11+8+7+2+1, 11+8+7+3+1, 11+8+7+4+1, 11+8+7+5+1, 11+9+1, 11+9+2+1, 11+9+3+1, 11+9+4+1, 11+9+5+1, 11+9+6+1, 11+9+6+2+1, 11+9+6+3+1, 11+9+6+4+1, 11+9+6+5+1, 11+9+7+1, 11+9+7+2+1, 11+9+7+3+1, 11+9+7+4+1, 11+9+7+5+1, 12+1, 12+2+1, 12+3+1, 12+4+1, 12+5+1, 12+6+1, 12+6+2+1, 12+6+3+1, 12+6+4+1, 12+6+5+1, 12+7+1, 12+7+2+1, 12+7+3+1, 12+7+4+1, 12+7+5+1, 12+8+1, 12+8+2+1, 12+8+3+1, 12+8+4+1, 12+8+5+1, 12+8+6+1, 12+8+6+2+1, 12+8+6+3+1, 12+8+6+4+1, 12+8+6+5+1, 12+8+7+1, 12+8+7+2+1, 12+8+7+3+1, 12+8+7+4+1, 12+8+7+5+1, 12+9+1, 12+9+2+1, 12+9+3+1, 12+9+4+1, 12+9+5+1, 12+9+6+1, 12+9+6+2+1, 12+9+6+3+1, 12+9+6+4+1, 12+9+6+5+1, 12+9+7+1, 12+9+7+2+1, 12+9+7+3+1, 12+9+7+4+1, 12+9+7+5+1, 13+1, 13+2+1, 13+3+1, 13+4+1, 13+5+1, 13+6+1, 13+6+2+1, 13+6+3+1, 13+6+4+1, 13+6+5+1, 13+7+1, 13+7+2+1, 13+7+3+1, 13+7+4+1, 13+7+5+1, 13+8+1, 13+8+2+1, 13+8+3+1, 13+8+4+1, 13+8+5+1, 13+8+6+1, 13+8+6+2+1, 13+8+6+3+1, 13+8+6+4+1, 13+8+6+5+1, 13+8+7+1, 13+8+7+2+1, 13+8+7+3+1, 13+8+7+4+1, 13+8+7+5+1, 13+9+1, 13+9+2+1, 13+9+3+1, 13+9+4+1, 13+9+5+1, 13+9+6+1, 13+9+6+2+1, 13+9+6+3+1, 13+9+6+4+1, 13+9+6+5+1, 13+9+7+1, 13+9+7+2+1, 13+9+7+3+1, 13+9+7+4+1, 13+9+7+5+1, 14+1, 14+2+1, 14+3+1, 14+4+1, 14+5+1, 14+6+1, 14+6+2+1, 14+6+3+1, 14+6+4+1, 14+6+5+1, 14+7+1, 14+7+2+1, 14+7+3+1, 14+7+4+1, 14+7+5+1.

In the list above the numbers refer to the embodiments according to their numbering provided hereinabove whereas "+" indicates the dependency from another embodiment. The different individualized embodiments are separated by commas. In other words, "10+9+4+1" for example refers to embodiment 10) depending on embodiment 9), depending on embodiment 4), depending on embodiment 1), i.e. embodiment "10+9+4+1" corresponds to the compounds of Formula (I) according to embodiment 1) further limited by all the features of the embodiments 4), 9), and 10). 16) Another embodiment relates to compounds of Formula (I) according to embodiment 1), which are selected from the following compounds:

(2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate;

(2R,3R,4R,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-6-(hydroxymethyl)tetrahydro-2H-pyran-3,5-diol;

(2R,3R,4S,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate;

(2R,3R,4R,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-6-(hydroxymethyl)tetrahydro-2H-pyran-3,5-diol;

(2R,3R,4R,5R,6R)-2-((1-oxa-2-azaspiro[4.5]dec-2-en-3-yl)methyl)-6-(hydroxymethyl)-4-(4-(3,4,5-trifluorophenyl)-1H-1,2,3-triazol-1-yl)tetrahydro-2H-pyran-3,5-diol;

(2R,3R,4S,5R,6R)-6-((1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl (3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate;

(2R,3R,4S,5R,6R)-6-((1-oxa-2-azaspiro[4.5]dec-2-en-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

tert-butyl ((5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate;

(2R,3R,4S,5R,6R)-6-((1-oxa-2-azaspiro[4.5]dec-2-en-3-yl)methyl)-4-(4-(4-bromo-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3-fluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3-chloro-4,5-difluorophenyl)-1H-1,2,3-triazol-1-yl)-2-(hydroxymethyl)-5-methoxytetrahydro-2H-pyran-3-ol;

(2R,3R,4S,5R,6R)-6-((1,8-dioxa-2-azaspiro[4.5]dec-2-en-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((1,8-dioxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1,8-dioxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.6]undec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile;

tert-butyl ((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate;

tert-butyl ((5s,8S)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate;

tert-butyl ((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

tert-butyl ((5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

tert-butyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-y)methyl)-1-oxa-2-azaspiro[4.5]dec-2-en-8-yl)carbamate tert-butyl ((5s,8S)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(2R,3R,4S,5R,6R)-2-(hydroxymethyl)-6-(((5r,8R)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-2-(hydroxymethyl)-6-(((5s,8S)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((8-(2-hydroxypropan-2-yl)-1-oxa-2-azaspiro[4.5]dec-2-en-3-yl)methyl)-5-methoxytetrahydro-2H-pyran-3-ol;

(5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(5s,8S)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5s,8S)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(2R,3R,4S,5R,6R)-4-(4-(2,3-difluoro-4-methylphenyl)-1H-1,2,3-triazol-1-yl)-2-(hydroxymethyl)-6-(((5r,8R)-8-(2-hydroxypropan-2-yl)-1-oxa-2-azaspiro[4.5]dec-2-en-3-yl)methyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol;

3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-one;

(2R,3R,4S,5R,6R)-6-((1-oxa-2-azaspiro[4.5]dec-2-en-3-yl)methyl)-5-(2,2-difluoroethoxy)-2-(hydroxymethyl)-4-(4-(3,4,5-trifluorophenyl)-1H-1,2,3-triazol-1-yl)tetrahydro-2H-pyran-3-ol;

methyl 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate;

(2R,3R,4S,5R,6R)-6-((1-oxa-2-azaspiro[4.5]dec-2-en-3-yl)methyl)-5-ethoxy-2-(hydroxymethyl)-4-(4-(3,4,5-trifluorophenyl)-1H-1,2,3-triazol-1-yl)tetrahydro-2H-pyran-3-ol;

2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-methylacetamide;

2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one;

methyl 2-(((2R,3R,4S,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetate;

(2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl carbamate;

(2R,3R,4S,5R,6R)-4-(4-(2,3-difluoro-4-methylphenyl)-1H-1,2,3-triazol-1-yl)-6-(((5r,8R)-8-((2,2-difluoroethyl)amino)-1-oxa-2-azaspiro[4.5]dec-2-en-3-yl)methyl)-2-(hydroxymethyl)-5-methoxytetrahydro-2H-pyran-3-ol;

tert-butyl (RS)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2,8-diazaspiro[4.6]undec-2-ene-8-carboxylate;

(RS)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2,8-diazaspiro[4.6]undec-2-en-9-one;

(RS)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-8-methyl-1-oxa-2,8-diazaspiro[4.6]undec-2-en-9-one;

(5RS,8S)-7-(tert-butoxycarbonyl)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2,7-diazaspiro[4.4]non-2-ene-8-carboxylic acid;

3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol;

(5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol;

N-((5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)acetamide;

N-((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)acetamide;

N-((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)acetamide;

N-((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)acetamide;

ethyl ((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

ethyl ((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate;

ethyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

(2R,3R,4S,5R,6R)-2-(hydroxymethyl)-6-(((5r,8R)-8-(isopropylamino)-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((8-((2,2,2-trifluoroethyl)amino)-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-(((5r,8R)-8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((5r,8R)-8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

2-(((2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid;

2-(((2R,3R,4S,5R,6R)-2-((1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid;

2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid;

(2R,3R,4S,5R,6R)-6-(((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

N-(tert-butyl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-ene-8-carboxamide;

1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-en-8-yl)ethan-1-one;

tert-butyl 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxo-1-oxa-3,8-diazaspiro[4.5]decane-8-carboxylate;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-3-azaspiro[4.5]decan-2-one;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,8-dioxa-3-azaspiro[4.5]decan-2-one;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,3-diazaspiro[4.5]decan-2-one;

2-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-2,4-diazaspiro[5.5]undecan-3-one;
(2R,3R,4S,5R,6R)-4-(4-(2,3-difluoro-4-methylphenyl)-1H-1,2,3-triazol-1-yl)-2-(hydroxymethyl)-5-methoxy-6-((2-methyl-1,3-diazaspiro[4.5]dec-1-en-3-yl)methyl)tetrahydro-2H-pyran-3-ol; and
(2R,3R,4S,5R,6R)-6-((1,3-diazaspiro[4.5]dec-1-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol.

17) In addition to the compounds listed in embodiment 16), further compounds of Formula (I) according to embodiment 1) are selected from the following compounds:

(2R,3R,4S,5R,6R)-6-((4'H-spiro[bicyclo[2.2.1]heptane-2,5'-isoxazol]-3'-yl)methyl)-4-(4-(2,3-difluoro-4-methylphenyl)-1H-1,2,3-triazol-1-yl)-2-(hydroxymethyl)-5-methoxytetrahydro-2H-pyran-3-ol; and
(2R,3R,4S,5R,6R)-6-((4'H-spiro[bicyclo[3.2.1]octane-3,5'-isoxazol]-3'-yl)methyl)-4-(4-(2,3-difluoro-4-methylphenyl)-1H-1,2,3-triazol-1-yl)-2-(hydroxymethyl)-5-methoxytetrahydro-2H-pyran-3-ol.

The compounds of Formula (I) according to embodiments 1) to 17) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of Formula (I) according to embodiments 1) to 17). In a sub-embodiment of the invention, the administered amount is comprised between 1 mg and 1000 mg per day.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

18) Another embodiment relates to the compounds of formula (I) as defined in any one of embodiments 1) to 17) which are useful for the prevention/prophylaxis or treatment of diseases and disorders that are related to galectin-3 binding to natural ligands.

Such diseases and disorders that are related to Gal-3 binding to natural ligands are especially diseases and disorders in which inhibition of the physiological activity of Gal-3 is useful, such as diseases in which a Gal-3 receptor participates, is involved in the etiology or pathology of the disease, or is otherwise associated with at least one symptom of the disease.

Diseases or disorders that are related to galectin-3 binding to natural ligands may in particular be defined as including:
fibrosis of organs comprising:
   all forms of lung/pulmonary fibrosis including all forms of fibrosing interstitial lung diseases, especially idiopathic pulmonary fibrosis (alternatively named cryptogenic fibrosing alveolitis); pulmonary fibrosis secondary to systemic inflammatory disease such as rheumatoid arthritis, scleroderma (systemic sclerosis, SSc), lupus (systemic lupus erythematosus, SLE), polymyositis, or mixed connective tissue disease (MCTD); pulmonary fibrosis secondary to sarcoidosis; iatrogenic pulmonary fibrosis including radiation-induced fibrosis; silicosis-induced pulmonary fibrosis; asbestos-induced pulmonary fibrosis; and pleural fibrosis;
   renal/kidney fibrosis, including renal fibrosis caused by/associated with chronic kidney disease (CKD), (acute or chronic) renal failure, tubulointerstitial nephritis, and/or chronic nephropathies such as (primary) glomerulonephritis and glomerulonephritis secondary to systemic inflammatory diseases such as SLE or SSc, diabetes, focal segmental glomerular sclerosis, IgA nephropathy, hypertension, renal allograft, and Alport syndrome;
   all forms of liver/hepatic fibrosis (associated or not with portal hypertension) including cirrhosis, alcohol-induced liver fibrosis, nonalcoholic steatohepatitis, biliary duct injury, primary biliary cirrhosis (also known as primary biliary cholangitis), infection- or viral-induced liver fibrosis (e.g. chronic HCV infection), and autoimmune hepatitis;
   all forms of heart/cardiac fibrosis, including heart/cardiac fibrosis associated with cardiovascular diseases, heart failure, Fabry disease, CKD; diabetes, hypertension, or hypercholesterolemia;
   gut fibrosis, including gut fibrosis secondary to SSc, and radiation-induced gut fibrosis;
   skin fibrosis, including SSc and skin scarring;
   head and neck fibrosis, including radiation-induced head and neck fibrosis;
   eye/corneal fibrosis, including scarring (e.g. sequelae of laser-assisted in situ keratomileusis, or trabeculectomy);
   hypertrophic scarring and keloids, including burn-induced or surgical hypertrophic scarring and keloids;
   fibrosis sequelae of organ transplant (including corneal transplant);
   and other fibrotic diseases including endometriosis, spinal cord fibrosis, myelofibrosis, perivascular and aterial fibrosis; as well as formation of scar tissue, Peyronie's disease, abdominal or bowel adhesions, bladder fibrosis, fibrosis of the nasal passages, and fibrosis mediated by fibroblasts;
(acute or chronic) liver diseases and disorders including acute and chronic viral hepatitis; cirrhosis caused by/associated with arthritis and vasculitis; metabolic liver diseases caused by/associated with arthritis, myocarditis, diabetes, or neurologic symptoms; cholestatic diseases caused by/associated with hyperlipidaemia, inflammatory bowel disease (IBD), or ulcerative colitis; liver tumors; autoimmune hepatitis and cirrhosis caused by/associated with celiac disease, autoimmune haemolytic anaemia, IBD, autoimmune thyroiditis, ulcerative colitis, diabetes, glomerulonephritis, pericarditis, autoimmune thyroiditis, hyperthyroidism, polymyositis, Sjörgen syndrome, panniculitis, alveolitis or alcoholic steatosis; cirrhosis associated with dementia; cirrhosis associated with peripheral neuropathy; cirrhosis caused by/associated with oral or oesophageal cancer; non-alcoholic fatty liver disease (especially non-alcoholic steatohepatitis) caused by/associated with obesity, metabolic syndrome or type 2 diabetes; hepatic blood vessel disorders (including Budd-Chiari syndrome, portal vein thrombosis, sinusoidal obstruction syndrome); acute and chronic liver failure (associated or not with portal hypertension); liver hypofunction;

acute kidney injury and chronic kidney disease (CKD) [especially CKD of stages 1 to 5 as defined by the Kidney Disease Improving Global Outcomes (KDIGO) Guidelines], in particular CKD (notably of these stages) caused by/associated with cardiac diseases (also referred to as cardio-renal syndrome type 1 and type 2), or caused by/associated with hypertension, or caused by/associated with diabetes (also referred to as diabetic kidney disease (DKD), including DKD associated with hypertension), wherein such diabetes especially is type 1 or type 2 diabetes), or caused by/associated with inflammatory diseases and disorders (such as glomerulonephritis and glomerulonephritis secondary to systemic inflammatory diseases such as SLE or SSc, tubulo-interstitial nephritis, vasculitis, sepsis, urinary tract infection), or caused by/associated with polycystic kidney disease, or caused by/associated with obstructive nephropathy (including calculi, benign prostatic hyperplasia, prostate cancer, retroperitoneal pelvic tumor), or caused by/associated with symptoms associated with neuropathic bladder disease); as well as acute and chronic renal failure;

cardiovascular diseases and disorders (including atherosclerosis caused by/associated with hypertension, hypercholesterolemia, diabetes, inflammation, obesity, elderly/age; peripheral arterial disease caused by/associated with hypertension, hypercholesterolemia, diabetes, elderly/age; deep venous thrombosis; pulmonary embolism caused by/associated with obesity or cancer; aortic aneurysm and dissection caused by/associated with elderly/age, hypertension, Marfan syndrome, congenital heart disorders, inflammatory or infectious disorders; cerebrovascular disease caused by/associated with hypertension, atrial fibrillation, hypercholesterolemia, diabetes, elderly/age; coronary heart disease caused by/associated with hypertension, hypercholesterolemia, diabetes, elderly/age, or CKD (especially CKD of stages 1 to 5 as defined by the Kidney Disease Improving Global Outcomes (KDIGO) Guidelines); rheumatic heart disease caused by/associated with bacterial infection; heart and vascular tumors; cardiomyopathy and arrythmias; valvular heart disease (including valvular calcification and degenerative aortic stenosis); inflammatory heart disease caused by/associated with infection, carditis, glomerulonephritis, cancer; heart failure (HF) defined as including especially congestive HF, including in particular systolic HF/HF with reduced ejection fraction (HFrEF), and diastolic HF/HF with preserved ejection fraction (HFpEF);

interstitial lung diseases and disorders (including smoking-related interstitial lung disease; interstitial lung disease associated with/caused by chronic obstructive pulmonary disease; interstitial pneumonia associated with collagen vascular disease (including usual interstitial pneumonia), or pneumonia);

cell proliferative diseases and cancers (including solid tumors, solid tumor metastasis, carcinoma, sarcoma, myeloma (and multiple myeloma), leukemia, lymphoma, mixed types of cancers, vascular fibroma, Kaposi's sarcoma, chronic lymphocytic leukemia (CLL), spinal cord tumors and invasive metastasis of cancer cells);

inflammatory and autoimmune diseases and disorders including chronic and acute inflammatory and autoimmune diseases and disorders (in particular including sepsis, Q-fever, asthma, rheumatoid arthritis, multiple sclerosis, SLE, SSc, polymyositis, plaque psoriasis (including psoriasis caused by/associated with NASH), atopic dermatitis, inflammatory renal/kidney diseases such as nephropathy (including diabetic nephropathy, glomerulonephritis, tubulointerstitial nephritis), inflammatory cardiac/heart diseases, inflammatory lung/lung related diseases; inflammatory liver/liver related diseases; diabetes (type 1 or type 2) and diabetes related diseases such as diabetic vasculopathy, diabetic nephropathy, diabetic retinopathy, diabetic peripheral neuropathy or skin related condition; viral encephalitis; and COVID-19 and sequelae thereof);

gastrointestinal tract diseases and disorders (including irritable bowel syndrome (IBS), inflammatory bowel disease (IBD), gastritis, and abnormal pancreatic secretion);

pancreatic diseases and disorders (including pancreatitis, e.g. associated with cystic fibrosis);

abnormal angiogenesis-associated diseases and disorders (including arterial obstruction);

brain-associated diseases and disorders (including stroke and cerebral haemorrhage);

neuropathic pain and peripheral neuropathy;

ocular diseases and disorders (including dry eye disease (dry eye syndrome), macular degeneration (AMD associated with age, diabetes related disease (diabetic retinopathy), proliferative vitreoretinopathy (PVR), cicatricial pemphigoid, and glaucoma (including glaucoma associated with elevated intraocular pressure, and ocular scarring after glaucoma filtration surgery), and corneal angiogenesis/neovascularization); and transplant rejection comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy; and sequelae of such transplant rejection.

19) A further embodiment relates to the compounds of formula (I) for use according to embodiment 18) wherein said compounds are for use in the prevention/prophylaxis or treatment of fibrosis of organs including liver/hepatic fibrosis, renal/kidney fibrosis, lung/pulmonary fibrosis, heart/cardiac fibrosis, eye/corneal fibrosis, and skin fibrosis; as well as gut fibrosis, head and neck fibrosis, hypertrophic scarring and keloids; and fibrosis sequelae of organ transplant.

20) A further embodiment relates to the compounds of formula (I) for use according to embodiment 18) wherein said compounds are for use in the prevention/prophylaxis or treatment of cardiovascular diseases and disorders.

21) A further embodiment relates to the compounds of formula (I) for use according to embodiment 18) wherein said compounds are for use in the prevention/ prophylaxis or treatment of acute kidney injury and chronic kidney disease (CKD).
22) A further embodiment relates to the compounds of formula (I) for use according to embodiment 18) wherein said compounds are for use in the prevention/prophylaxis or treatment of (acute or chronic) liver diseases and disorders.
23) A further embodiment relates to the compounds of formula (I) for use according to embodiment 18) wherein said compounds are for use in the prevention/prophylaxis or treatment of interstitial lung diseases and disorders.
24) A further embodiment relates to the compounds of formula (I) for use according to embodiment 18) wherein said compounds are for use in the prevention/prophylaxis or treatment of ocular diseases and disorders.
25) A further embodiment relates to the compounds of formula (I) for use according to embodiment 18) wherein said compounds are for use in the prevention/prophylaxis or treatment of cell proliferative diseases and cancers.
26) A further embodiment relates to the compounds of formula (I) for use according to embodiment 18) wherein said compounds are for use in the prevention/prophylaxis or treatment of chronic or acute inflammatory and autoimmune diseases and disorders.
27) A further embodiment relates to the compounds of formula (I) for use according to embodiment 18) wherein said compounds are for use in the prevention/prophylaxis or treatment of gastrointestinal tract diseases and disorders.
28) A further embodiment relates to the compounds of formula (I) for use according to embodiment 18) wherein said compounds are for use in the prevention/prophylaxis or treatment of pancreatic diseases and disorders.
29) A further embodiment relates to the compounds of formula (I) for use according to embodiment 18) wherein said compounds are for use in the prevention/prophylaxis or treatment of abnormal angiogenesis-associated diseases and disorders.
30) A further embodiment relates to the compounds of formula (I) for use according to embodiment 18) wherein said compounds are for use in the prevention/prophylaxis or treatment of brain-associated diseases and disorders.
31) A further embodiment relates to the compounds of formula (I) for use according to embodiment 18) wherein said compounds are for use in the prevention/prophylaxis or treatment of neuropathic pain and peripheral neuropathy.
32) A further embodiment relates to the compounds of formula (I) for use according to embodiment 18) wherein said compounds are for use in the treatment of transplant rejection.

Preparation of Compounds of Formula (I):

The compounds of Formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases, the order of carrying out the following reaction schemes, and/or reaction steps, may be varied to facilitate the reaction or to avoid unwanted reaction products. In the general sequence of reactions outlined below, the generic groups $R^1$, A, B and $Ar^1$ are as defined for Formula (I). Other abbreviations used herein are explicitly defined, or are as defined in the experimental section. In some instances, the generic groups $R^1$, A, B and $Ar^1$ might be incompatible with the assembly illustrated in the schemes below and so will require the use of protecting groups (Pg). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases, the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of the Formula (I) of the present invention can be prepared according to the general sequence of reactions outlined below. Only a few of the synthetic possibilities leading to compounds of Formula (I) are described.

Structure 1

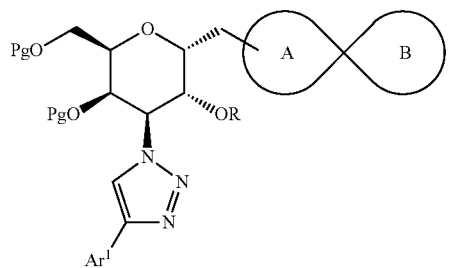

Compounds of Formula (I) are prepared by deprotecting a compound of Structure 1 in which R represents hydrogen, a suitable protective group such as acetyl, trimethylsilyl, TBDMS or $R^1$, as defined in Formula (I).

Compounds of Structure 1 in which ring A represents a 3,5,5-trisubstituted isoxazoline (Structure 1a) are synthesised as shown below by 1,3-dipolar cycloadditions of nitrile oxides with exocyclic alkenes of Structure 2. As precursors of nitrile oxides serve oximes such as Structures 3 which are oxidised in situ (e.g. with N-chlorosuccinimide) followed by elimination with a base such as lutidine, $NEt_3$ or DIPEA in a suitable solvent such as DCM or DMF at temperatures ranging between rt and 50° C. If ring B contains substituents, mixtures of diastereomers are formed during cycloaddition. These isomers can be separated by chromatography on silica gel using various solvent mixtures and gradients or HPLC as described in the experimental part.

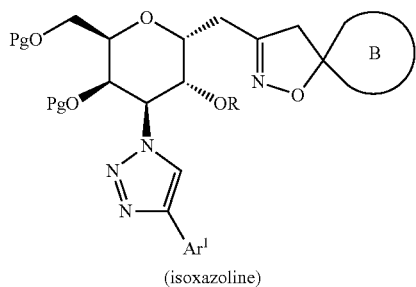

Structure 1a (isoxazoline)

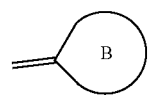

Structure 2

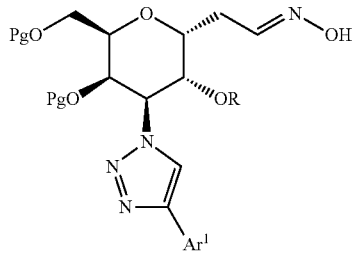

Structure 3

Compounds of Structure 1 in which ring A represents a 3,5,5-trisubstituted oxazolidinone (Structure 1b) can be prepared by opening a exocyclic epoxide of structure 4 with an amine of structure 5, followed by cyclisation with carbonic acid derivative such as CDI or phosgene.

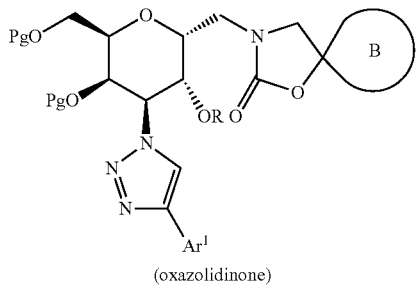

Structure 1b (oxazolidinone)

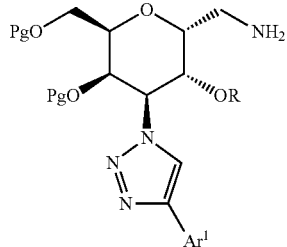

Structure 4

Structure 5

Compounds of Structure 1 in which ring A represents a cyclic 5- or 6-membered urea (Structure 1c) can be prepared by reductive amination of a compound of structure 6 with an amine of structure 5, followed by cyclisation using a strong base such as NaH, KOtBu or other non-nucleophilic strong bases as shown in the scheme below.

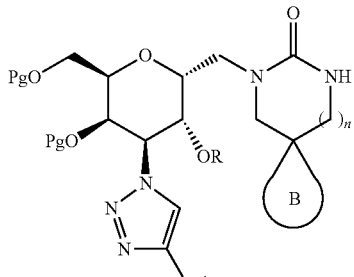

Structure 1c (cyclic urea)

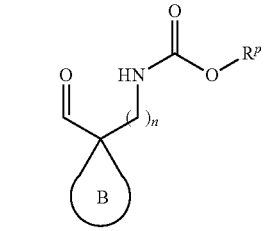

Structure 6

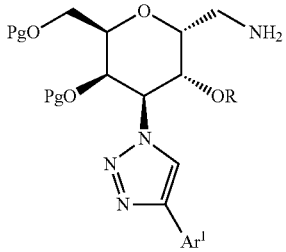

Structure 5

Compounds of Structure 1 in which the ring A represents a cyclic 5- or 6-membered amidine (Structure 1d) can be prepared by reductive amination of a compound of structure 6 with an amine of structure 5, followed by deprotection and cyclisation of the resulting diamine with an orthoformate or orthoacetate or derivatives thereof as shown in the scheme below.

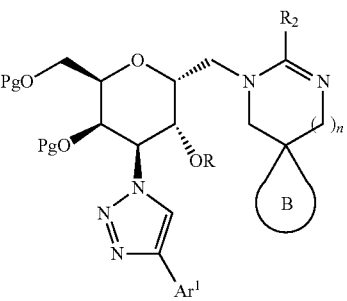

Structure 1d (cyclic amidines or guanidines)

Structure 6

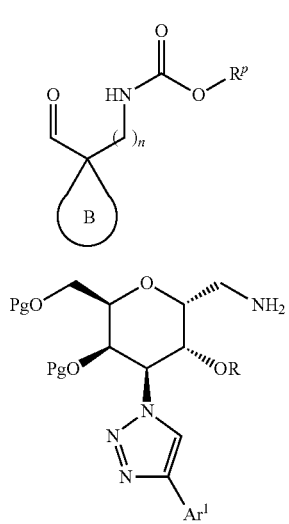

Structure 5

EXPERIMENTAL PART

The following examples illustrate the invention but do not at all limit the scope thereof.

All temperatures are stated in ° C. Commercially available starting materials were used as received without further purification. Unless otherwise specified, all reactions were carried out under an atmosphere of nitrogen or argon. Compounds were purified by flash chromatography on silica gel (Biotage), by prep TLC (TLC-plates from Merck, Silica gel 60 $F_{254}$) or by preparative HPLC. Compounds described in the invention are characterized by $^1$H-NMR (400 MHz or 500 MHz Bruker; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) using the conditions listed below.

Characterization methods used:

The LC-MS retention times have been obtained using the following elution conditions:

LC-MS (A):

Zorbax RRHD SB-Aq, 1.8 µm, 2.1×50 mm column thermostated at 40° C. The two elution solvents were as follows: solvent A=water+0.04% TFA; solvent B=acetonitrile. The eluent flow rate was 0.8 mL/min and the characteristics of the eluting mixture proportion in function of the time t from start of the elution are summarized in the table below (a linear gradient being used between two consecutive time points):

| t (min) | 0 | 0.01 | 1.20 | 1.90 | 2.10 |
|---|---|---|---|---|---|
| Solvent A (%) | 95 | 95 | 5 | 5 | 95 |
| Solvent B (%) | 5 | 5 | 95 | 95 | 5 |

Detection: UV at 210 nm.

The purifications by preparative LC-MS have been performed using the conditions described hereafter.

Preparative LC-MS (I):

A Waters column (Waters XBridge C18, 10 µm OBD, 30×75 mm) was used. The two elution solvents were as follows: solvent A=water+0.5% of a solution of 25% NH$_4$OH in water; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

Detection 210 nm.

Preparative LC-MS (II):

A Waters column (Waters XBridge C18, 10 µm OBD, 30×75 mm) was used. The two elution solvents were as follows: solvent A=water+HCOOH 0.5%; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

Detection 210 nm.

Preparative LC-MS (III):

A Waters column (Zorbax SB-AQ 30×75 mm 5 µm) was used. The two elution solvents were as follows: solvent A=water+HCOOH 0.5%; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 90 | 90 | 5 | 5 | 90 | 90 |
| Solvent B (%) | 10 | 10 | 95 | 95 | 10 | 10 |

Detection 210 nm.

Chiral Preparative HPLC Methods Used:

The separation of epimers has been performed by preparative chiral column chromatography using the conditions described hereafter.

Chiral Preparative HPLC (I):

ChiralPack OZ-H, 5 µm, 30×250 mm was used, column thermostated at 40° C. The two elution solvents were as follows: solvent A=CO$_2$; solvent B=ACN/EtOH 1:1. The eluent flow rate was 160 mL/min. The elution was done using 60% of the solvent A and 40% of the solvent B. The injection V=1.0 mL, 10 mg/mL MeOH. Wavelength 247 nm. (Examples 2.02/2.03)

Chiral Preparative HPLC (II):

ChiralPack OJ-H, 30×250 mm was used, column thermostated at 40° C. The two elution solvents were as follows: solvent A=CO$_2$; solvent B=ACN/MeOH 1:1. The eluent flow rate was 160 mL/min. The elution was done using 85% of the solvent A and 15% of the solvent B. The injection V=2 mL, 10 mg/mL MeOH. Wavelength 245 nm. (Examples 1.62/1.63, 1.64/1.65)

Chiral Preparative HPLC (III):
ChiralPack IC, 5 μm, 30×250 mm was used, column thermostated at 40° C. The two elution solvents were as follows: solvent A=CO$_2$; solvent B=ACN/EtOH/DEA 50:50:0, 1. The eluent flow rate was 160 mL/min. The elution was done using 60% of the solvent A and 40% of the solvent B. The injection V=1.2 mL, 11 mg/mL EtOH/ACN 1:1. (Examples 2.20/2.21, 2.22/2.23)

Chiral Preparative HPLC (IV):
ChiralPack IF, 5 μm, 30×250 mm was used, column thermostated at 40° C. The two elution solvents were as follows: solvent A=CO$_2$; solvent B=ACN/EtOH 50:50. The eluent flow rate was 160 mL/min. The elution was done using 60% of the solvent A and 40% of the solvent B. The injection V=1 mL, 11.2 mg/mL EtOH/ACN 1:1. (Examples 1.44/145 (acetal protected))

Chiral Preparative HPLC (V):
ChiralPack IE, 5 μm, 30×250 mm was used, column thermostated at 40° C. The two elution solvents were as follows: solvent A=CO$_2$; solvent B=ACN/MeOH 50:50. The eluent flow rate was 160 mL/min. The elution was done using 55% of the solvent A and 45% of the solvent B. The injection V=3 mL, 10 mg/mL MeOH/ACN 1:1. (Examples 1.15/1.16, 1.52/1.53, 1.61)

Chiral Preparative HPLC (VI):
ChiralPack OD-H, 30×250 mm was used, column thermostated at 40° C. The two elution solvents were as follows: solvent A=CO$_2$; solvent B=ACN/MeOH 1:1. The eluent flow rate was 160 mL/min. The elution was done using 70% of the solvent A and 30% of the solvent B. The injection V=1 mL, 10 mg/mL MeOH. (Examples 1.56/1.57, 1.58/1.59, 1.60/1.61)

Chiral Preparative HPLC (VII): ChiralCell OJ-H, 30×250 mm was used, column thermostated at 40° C. The two elution solvents were as follows: solvent A=CO$_2$; solvent B=ACN/MeOH 1:1. The eluent flow rate was 160 mL/min. The elution was done using 70% of the solvent A and 30% of the solvent B. The injection V=1 mL, 10 mg/mL MeOH. (Examples 1.27/1.28, 1.33/1.34)

NMR:
$^1$H-NMR spectra are recorded on a Bruker Avance II, 400 MHz Ultra Shield™ or Brooker Avance III HD, Ascend 500 MHz; chemical shifts are given in ppm relative to the solvent used; multiplicities: s=singlet, d=doublet, t=triplet, q=quadruplet, quint=quintuplet, hex=hextet, hept=heptet, m=multiplet, br=broad, coupling constants are given in Hz).

Abbreviations (as Used Herein)

Ac acetyl
Ac$_2$O acetic anhydride
AcOH acetic acid
aq. aqueous
BF$_3$OEt$_2$ boron trifluoride diethyletherate
Boc tert-butoxycarbonyl
Bu butyl (such as in nBuLi=n-butyl lithium)
CC column chromatography on silica
CDI 1,1-carbonyldiimidazole
conc. concentrated
DCM dichloromethane
dil. dilute
DIPEA N-ethyl diisopropyl amine
DMAP 4-dimethylamino pyridine
DMF dimethylformamide
DMSO dimethylsulfoxide
EA ethyl acetate
EDC HCl N-(3-dimethylaminopropyl)-N'-ethylcarbodiimide hydrochloride
eq (molar) equivalent(s)
Ex. example
Et ethyl
EtOH ethanol
Et$_2$O diethyl ether
FC flash chromatography
h hour(s)
HATU 1-[Bis(dimethylamino)methylene]-1H-1,2,3-triazolo[4,5-b]pyridinium 3-oxid hexafluorophosphate
Hept heptane
HOBt 1-hydroxybenzotriazole hydrate
HPLC high performance liquid chromatography
M molarity [mol L$^{-1}$]
Me methyl
MeCN acetonitrile
MeOH methanol
Ms methanesulfonyl
MS mass spectroscopy
min. minute(s)
N normality
NaOAc sodium acetate
NaOMe sodium methoxide
NaOtBu sodium tert. (tertiary) butoxide
NEt$_3$ triethyamine
o/n over night
org. organic
Pg protecting group
Ph phenyl
PTSA p-Toluenesulfonic acid
rt room temperature
sat. saturated
TBAF tetra n-butylammonium fluoride
TBME tert.-butylmethylether
TBSCI tert.-butyldimethylsilyl chloride
TBTU O-benzotriazol-1-yl-N,N,N',N'-tetramethyluronium tetrafluoroborate
tBu tert-butyl=tertiary butyl
TFA trifluoroacetic acid
THE tetrahydrofuran
TMEDA tetramethylethylenediamine
TMSCI trimethylsilyl chloride
T3P propylphosphonic anhydride
$t_R$ retention time A—Preparation of Precursors and Intermediates

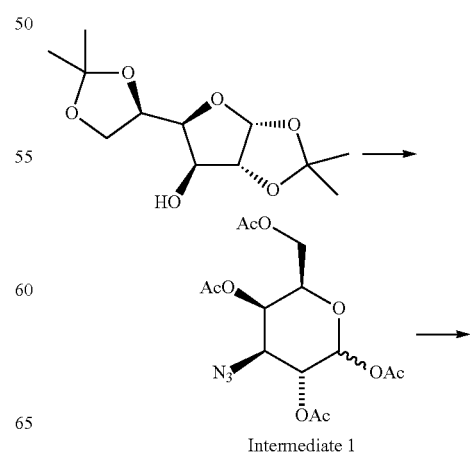

Intermediate 1

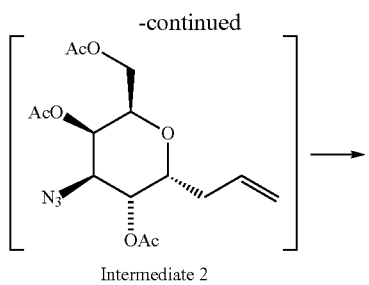

Intermediate 2

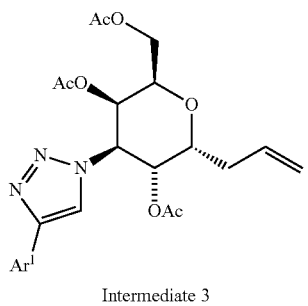

Intermediate 3

Intermediate 1: (3R,4S,5R,6R)-6-(Acetoxymethyl)-4-azidotetrahydro-2H-pyran-2,3,5-triyl triacetate (3R,4S,5R,6R)-6-(acetoxymethyl)-4-azidotetrahydro-2H-pyran-2,3,5-triyl triacetate is synthesized from (3aR,5S,6S,6aR)-5-(I-2,2-dimethyl-1,3-dioxolan-4-yl)-2,2-dimethyltetrahydrofuro[2,3-d][1,3]dioxol-6-ol following the literature procedures from Ref: Carbohydrate Research 1994, 251, 33-67 and references cited therein.

Intermediate 2: (2R,3R,4R,5R,6R)-2-(acetoxymethyl)-6-allyl-4-azidotetrahydro-2H-pyran-3,5-diyl diacetate A solution of Intermediate 1 (10 g, 26.8 mmol, 1 eq) in MeCN (100 mL) is cooled to 0° C. and allyltrimethylsilane 98% (13 mL, 80.4 mmol, 3 eq) and dropwise trimethylsilyl trifluoromethanesulfonate 99% (2.45 mL, 13.4 mmol, 0.5 eq) are added (not exothermic). The ice bath is removed and the mixture stirred at rt for 72 h. The mixture is poured to sat. NaHCO₃ solution and extracted with TBME. Org. phase is washed with brine, dried over MgSO₄ and concentrated. The crude is purified by filtration over SiO₂ (DCM/TBME 9:1) to give the title intermediate (as a 9:1 mixture of alpha/beta isomers) as a colourless oil which is used in the next step without further purification.

major isomer: $^1$H NMR (500 MHz, DMSO) δ: 5.70-5.78 (m, 2H), 5.31 (dd, J$^1$=1.6 Hz, J2=3.4 Hz, 1H), 5.06-5.14 (m, 2H), 4.98-5.04 (m, 1H), 4.39 (dd, J$^1$=3.4 Hz, J$^2$=10.6 Hz, 1H), 4.15 (m, 1H), 3.91-4.09 (m, 4H), 2.56-2.65 (m, 1H), 2.22-2.28 (m, 1H), 2.11 (s, 3H), 2.09 (s, 3H), 1.99 (s, 3H).

Intermediate 3a: (2R,3R,4R,5R,6R)-2-(acetoxymethyl)-6-allyl-4-(4-(3,4,5-trifluorophenyl)-1H-1,2,3-triazol-1-yl)tetrahydro-2H-pyran-3,5-diyl diacetate To a solution of Intermediate 2 (15 g, 42.5 mmol, 1 eq) in DMF (160 mL) are added 5-ethynyl-1,2,3-trifluorobenzene (9950 mg, 63.7 mmol, 1.5 eq), copper(I) iodide (809 mg, 4.25 mmol, 0.1 eq) and Net₃ (17.8 mL, 127 mmol, 3 eq) and stirred at rt overnight. The mixture is diluted with EA and dil. HCl. Org. phase is washed with water and brine, dried over MgSO₄ and concentrated. The crude is crystallised from EA (20 mL) and TBME (200 mL) to give the desired pure alpha isomer as a colourless solid. LCMS (A): t$_R$=1.02 min; [M+H]$^+$=512.15

$^1$H NMR (500 MHz, DMSO-d6) δ: 8.78 (s, 1H), 7.83-7.88 (m, 2H), 5.75-5.84 (m, 1H), 5.70-5.74 (m, 2H), 5.36 (s, 1H), 5.18-5.21 (m, 1H), 5.10-5.14 (m, 1H), 4.41 (m, 1H), 4.35 (m, 1H), 4.00-4.04 (m, 1H), 3.94 (dd, J$^1$=7.1 Hz, J2=11.3 Hz, 1H), 2.84-2.91 (m, 1H), 2.30-2.35 (m, 1H), 2.02 (s, 3H), 1.98 (s, 3H), 1.86 (s, 3H).

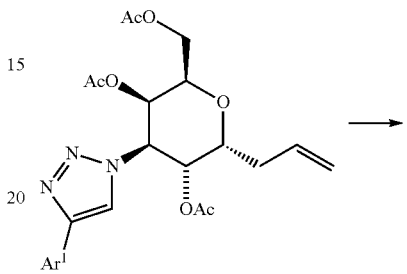

Intermediate 3

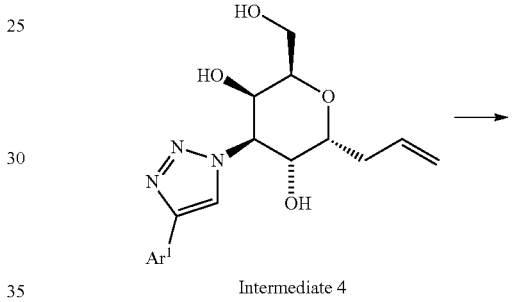

Intermediate 4

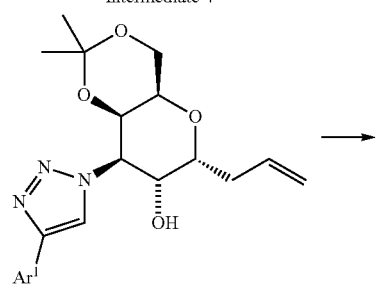

Intermediate 5

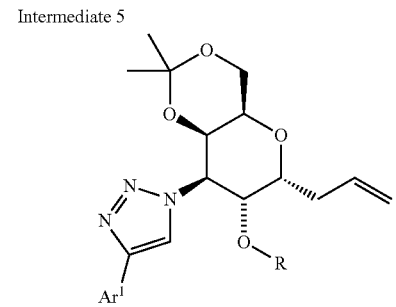

Intermediate 6

Intermediate 4a: (2R,3R,4R,5R,6R)-2-allyl-6-(hydroxymethyl)-4-(4-(3,4,5-trifluorophenyl)-1H-1,2,3-triazol-1-yl)tetrahydro-2H-pyran-3,5-diol To a solution of Intermediate 3a (12 g, 23.5 mmol, 1 eq) in methanol (240 mL) is added K₂CO₃ (324 mg, 2.35 mmol, 0.1 eq). The reaction mixture is stirred at rt for 2 h. The mixture is concentrated in vacuo to afford a beige foam. The crude compound is purified by FC (DCM/MeOH 9:1) to give the desired product as a colourless solid.

LCMS (A): $t_R$=0.7 min; [M+H]$^+$=385.76

$^1$H NMR (500 MHz, DMSO-d6) δ: 8.72 (s, 1H), 7.82-7.87 (m, 2H), 5.88 (m, 1H), 5.26 (d, J=5.7 Hz, 1H), 5.14-5.19 (m, 2H), 5.05-5.07 (m, 1H), 4.90 (dd, J1=2.9 Hz, J2=11.4 Hz, 1H), 4.58 (t, J=5.5 Hz, 1H), 4.52 (m, 1H), 4.02 (m, 1H), 3.93 (dd, J1=2.6 Hz, J2=6.4 Hz, 1H), 3.78 (t, J=6.2 Hz, 1H), 3.49 (m, 1H), 3.42 (m, 1H), 2.68-2.75 (m, 1H), 2.33-2.38 (m, 1H).

Intermediate 5a: (4aR,6R,7R,8R,8aR)-6-allyl-2,2-dimethyl-8-(4-(3,4,5-trifluorophenyl)-1H-1,2,3-triazol-1-yl)hexahydropyrano[3,2-d][1,3]dioxin-7-ol A solution of Intermediate 4a (15 g, 38.9 mmol, 1 eq) in THF (180 mL) is treated with 2,2-dimethoxypropane (19.1 mL, 156 mmol, 4 eq) and PTSA monohydrate (0.378 g, 1.95 mmol, 0.05 eq) and the light yellow solution is stirred at rt o/n. The mixture is diluted with EA and the org. layer is washed with sat. NaHCO$_3$ solution, water and brine, dried over MgSO$_4$, filtered and concentrated under reduced pressure to give the title intermediate as a colourless solid.

LCMS (A): $t_R$=0.93 min; [M+H]$^+$=426.13

$^1$H NMR (500 MHz, DMSO-d6) δ: 8.72 (s, 0H), 8.58-8.64 (m, 1H), 7.80-7.94 (m, 2H), 5.81-5.90 (m, 1H), 5.33-5.38 (m, 1H), 5.11-5.20 (m, 1H), 5.00-5.11 (m, 2H), 4.41-4.52 (m, 1H), 4.26-4.31 (m, 1H), 4.12 (ddd, J$^1$=11.5 Hz, J$^2$=5.7 Hz, J$^3$=3.2 Hz, 1H), 4.01 (dd, J$^1$=12.7 Hz, J$^2$=2.0 Hz, 1H), 3.66-3.71 (m, 1H), 3.57-3.65 (m, 1H), 2.64-2.72 (m, 1H), 2.34-2.41 (m, 1H), 1.32 (s, 3H), 1.20 (s, 3H).

Intermediate 6a: 1-((4aR,6R,7R,8R,8aR)-6-allyl-7-methoxy-2,2-dimethylhexahydropyrano[3,2-d][1,3]dioxin-8-yl)-4-(3,4,5-trifluorophenyl)-1H-1,2,3-triazole To a solution of Intermediate 5a (7.3 g, 17.2 mmol, 1 eq) in dry THF (50 mL) cooled to 0° C. is added dimethyl sulfate (2 mL, 20.6 mmol, 1.2 eq) followed by NaH [55% dispersion in paraffin] (824 mg, 20.6 mmol, 1.2 eq) portion wise. The mixture is stirred at 0° C. for 3 h. The mixture is quenched with sat. NH$_4$Cl and extracted twice with TBME. The combined org. layers are washed with brine, dried over MgSO$_4$, filtered and concentrated under reduced pressure to afford a colourless solid. LCMS (A): $t_R$=1.03 min; [M+H]$^+$=440.22

$^1$H NMR (500 MHz, DMSO-d6) δ: 8.71 (s, 1H), 7.68-7.98 (m, 2H), 5.70-5.97 (m, 1H), 5.14-5.21 (m, 2H), 5.09 (m, 1H), 4.48 (ddd, J$^1$=3.5 Hz, J$^2$=5.5 Hz, J$^3$=11.4 Hz, 1H), 4.30 (d, J=2.9 Hz, 1H), 4.22 (dd, J$^1$=5.7 Hz, J$^2$=11.5 Hz, 1H), 3.93-4.10 (m, 1H), 3.56-3.74 (m, 2H), 3.21 (s, 3H), 2.70-2.78 (m, 1H), 2.20-2.31 (m, 1H), 1.32 (s, 3H), 1.20 (s, 3H).

Intermediate 6b: (4aR,6R,7R,8S,8aR)-6-allyl-2,2-dimethyl-8-(4-(3,4,5-trifluorophenyl)-1H-1,2,3-triazol-1-yl)hexahydropyrano[3,2-d][1,3]dioxin-7-yl acetate Intermediate 5a (725 mg, 1.7 mmol, 1 eq) is dissolved in DCM (10 mL) and Ac$_2$O (0.193 mL, 2.05 mmol, 1.2 eq), DIPEA (0.438 mL, 2.56 mmol, 1.5 eq) and DMAP (10.4 mg, 0.0852 mmol, 0.05 eq) are added. The mixture is stirred at rt for 1 h. The mixture is partitioned between EA and NaHCO$_3$ solution. The org. phase is washed with sat NH$_4$Cl and brine, dried over MgSO$_4$ and concentrated. Purification by FC (hept/EA 2:1, 1:1, 1:2) gives the title intermediate as a colourless foam. LCMS (A): $t_R$=1.04 min; [M+H]+=467.98

$^1$H NMR (500 MHz, DMSO-d6) δ: 8.63 (s, 1H), 7.89 (m, 2H), 5.81 (m, 1H), 5.59 (dd, J$^1$=5.7 Hz, J$^2$=11.4 Hz, 1H), 5.47 (dd, J$^1$=3.2 Hz, J$^2$=11.4 Hz, 1H), 5.19 (dd, J$^1$=1.9 Hz, J$^2$=17.2 Hz, 1H), 5.09 (m, 1H), 4.36-4.41 (m, 2H), 4.03-4.06 (m, 1H), 3.76 (d, J=1.0 Hz, 1H), 3.66 (dd, J$^1$=1.7 Hz, J$^2$=12.8 Hz, 1H), 2.80 (m, 1H), 2.28-2.33 (m, 1H), 1.84 (s, 3H), 1.38 (s, 3H), 1.25 (s, 3H).

Intermediate 6c: ((2R,3R,4R,5R,6R)-3-acetoxy-6-allyl-5-methoxy-4-(4-(3,4,5-trifluorophenyl)-1H-1,2,3-triazol-1-yl)tetrahydro-2H-pyran-2-yl)methyl acetate Step 1: (2R,3R,4S,5R,6R)-6-allyl-2-(hydroxymethyl)-5-methoxy-4-(4-(3,4,5-trifluorophenyl)-1H-1,2,3-triazol-1-yl)tetrahydro-2H-pyran-3-ol To a mixture of Intermediate 6a (3050 mg, 6.94 mmol, 1 eq) in water (15 mL) is added acetic acid (30 mL) and the suspension is stirred at 55° C. for 3h. The solution is concentrated under reduced pressure and the residue is dried under hv o/n. The crude (light yellow solid) is used in the next step without further purification.

Step 2

To a solution of Intermediate of step 1 (3340 mg, 8.36 mmol, 1 eq) and Et$_3$N (6.99 mL, 50.2 mmol, 6 eq) in DCM (40 mL) at 0° C. under N$_2$ is added Ac$_2$O (2.42 mL, 25.1 mmol, 3 eq) and the solution is stirred at rt for o/n. Water is added and the mixture is extracted with DCM. The org. layer is dried over MgSO$_4$ and is then concentrated under reduced pressure to give the title intermediate as a colourless solid.

LCMS (A): $t_R$=1.03 min; [M+H]+=484.20

Intermediate 6d: 1-((4aR,6R,7R,8S,8aR)-6-allyl-7-((tert-butyldimethylsilyl)oxy)-2,2-dimethylhexahydropyrano[3,2-d][1,3]dioxin-8-yl)-4-(3,4,5-trifluorophenyl)-1H-1,2,3-triazole Intermediate 5a (2000 mg, 4.7 mmol, 1 eq) is dissolved in dry DCM (30 mL) and the solution is cooled to 0° C. Under N$_2$ is added 2,6-lutidine (1.1 mL, 9.4 mmol, 2 eq), followed by the dropwise addition of tert-butyldimethylsilyl trifluoromethanesulfonate (1.32 mL, 5.64 mmol, 1.2 eq) within 5 min. The yellowish solution is stirred at 0° C. for 30 min and at rt overnight. The mixture is quenched with water and the two layers are separated. The org. layer is dried using a phase separator and is then concentrated under reduced pressure to give an off-white foam which is used without further purification. LCMS (A): $t_R$=1.23 min; [M+H]+=540.22

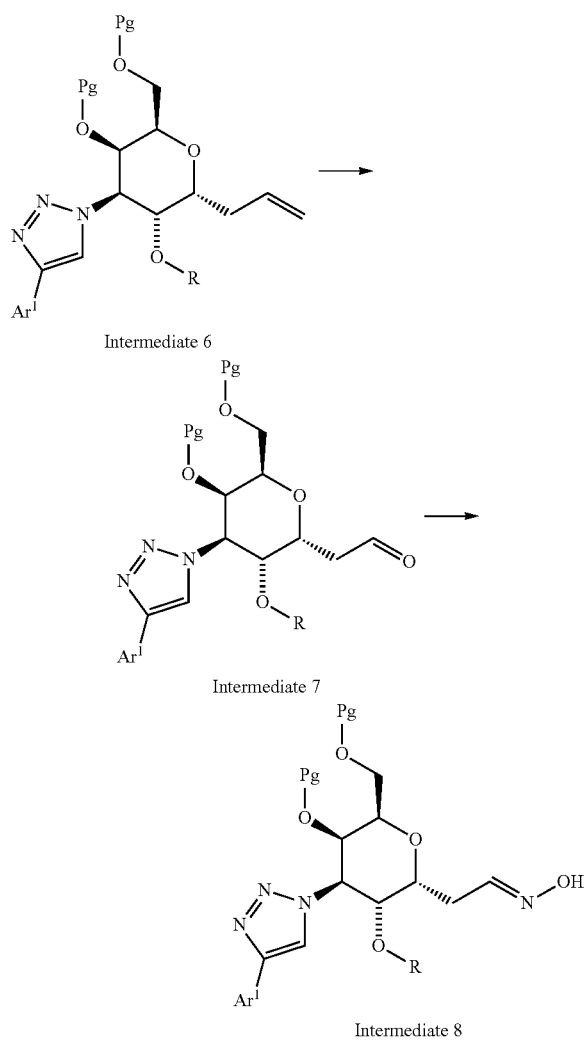

Intermediate 6

Intermediate 7

Intermediate 8

Intermediate 7a: 2-((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)acetaldehyde Intermediate 6a (4270 mg, 9.72 mmol, 1 eq) is suspended in 1,4-dioxane (50 mL) and water (15 mL). 2,6-lutidine (1.24 mL, 10.6 mmol, 3 eq) and sodium periodate (6235 mg, 29.2 mmol, 3 eq) are added, followed by the addition of potassium osmate dihydrate (15 mg, 0.0408 mmol, 0.0042 eq). The suspension is vigorously stirred at rt o/n. The mixture is diluted with water and EA and adjusted carefully to pH 2-3 with HCl 1N. The two layers are separated and the org. layer is washed with brine, dried over $MgSO_4$ and concentrated under reduced pressure. The crude is purified by FC using CombiFlash (40 g $SiO_2$ column; gradient: 0-100% EA in hept) to give the desired aldehyde as a colourless solid. LCMS (A): $t_R$=0.91 min; $[M+H]^+$=442.12

$^1$H NMR (500 MHz, DMSO-d6) δ: 9.72 (m, 1H), 8.73 (s, 1H), 7.87 (dd, $J^1$=9.0 Hz, $J^2$=6.8 Hz, 2H), 5.11-5.18 (m, 2H), 4.24-4.30 (m, 2H), 4.01-4.04 (m, 1H), 3.57-3.69 (m, 2H), 3.32 (s), 3.20 (s, 3H), 2.98 (ddd, $J^1$=16.2 Hz, $J^2$=9.2 Hz, $J^3$=3.0 Hz, 1H), 2.83 (ddd, $J^1$=16.2 Hz, $J^2$=5.0 Hz, $J^3$=1.4 Hz, 1H), 1.18-1.33 (m, 6H).

Intermediate 7b: (4aR,6R,7R,8S,8aR)-2,2-dimethyl-6-(2-oxoethyl)-8-(4-(3,4,5-trifluorophenyl)-1H-1,2,3-triazol-1-yl)hexahydropyrano[3,2-d][1,3]dioxin-7-yl acetate Preparation in analogy to Intermediate 7a, starting from Intermediate 6b. LCMS (A): $t_R$=0.92 min; $[M+H]^+$=469.96

Intermediate 7c: (2R,3R,4R,5R,6R)-2-(acetoxymethyl)-6-(2-oxoethyl)-4-(4-(3,4,5-trifluorophenyl)-1H-1,2,3-triazol-1-yl)tetrahydro-2H-pyran-3,5-diyl diacetate Preparation in analogy to Intermediate 7a, starting from Intermediate 3a. LCMS (A): $t_R$=0.93 min; $[M+H]^+$=514.10

Intermediate 7d: 2-((4aR,6R,7R,8S,8aR)-7-((tert-butyldimethylsilyl)oxy)-2,2-dimethyl-8-(4-(3,4,5-trifluorophenyl)-1H-1,2,3-triazol-1-yl)hexahydropyrano[3,2-d][1,3]dioxin-6-yl)acetaldehyde Preparation in analogy to Intermediate 7a, starting from Intermediate 6d. LCMS (A): $t_R$=1.16 min; $[M+H]1$=542.18

Intermediate 8a: -2-((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)acetaldehyde oxime Intermediate 7a (1390 mg, 3.15 mmol, 1 eq), hydroxylamine HCl (328 mg, 4.72 mmol, 1.5 eq) and NaOAc (775 mg, 9.45 mmol, 3 eq) are charged into a flask and suspended in EtOH (5 mL) and $H_2O$ (5 mL). THF (10 mL) are added and the mixture is stirred at rt for 1.5 h. The mixture is partitioned between EA and water. The org. layer is washed with brine, dried over $MgSO_4$ and concentrated under reduced pressure. The crude is triturated in TBME and hept 3/1 (20 mL), treated with ultrasonic sound and off-white crystals are filtered off and dried at hv.

The desired oxime (E/Z mixture) is isolated as an off-white solid. LCMS (A): $t_R$=0.88 min; $[M+H]^+$=457.16

Intermediate 8b: (4aR,6R,7R,8S,8aR)-6-(-2-(hydroxyimino)ethyl)-2,2-dimethyl-8-(4-(3,4,5-trifluorophenyl)-1H-1,2,3-triazol-1-yl)hexahydropyrano[3,2-d][1,3]dioxin-7-yl acetate Preparation in analogy to Intermediate 8a, starting from Intermediate 7b. LCMS (A): $t_R$=0.90 min; $[M+H]^+$=485.18

Intermediate 8c: (2R,3R,4R,5R,6R)-2-(acetoxymethyl)-6-(-2-(hydroxyimino)ethyl)-4-(4-(3,4,5-trifluorophenyl)-1H-1,2,3-triazol-1-yl)tetrahydro-2H-pyran-3,5-diyl diacetate Preparation in analogy to Intermediate 8a, starting from Intermediate 7c. LCMS (A): $t_R$=0.89 min; $[M+H]^+$=529.05

Intermediate 8d: 2-((4aR,6R,7R,8S,8aR)-7-((tert-butyldimethylsilyl)oxy)-2,2-dimethyl-8-(4-(3,4,5-trifluorophenyl)-1H-1,2,3-triazol-1-yl)hexahydropyrano[3,2-d][1,3]dioxin-6-yl)acetaldehyde oxime Preparation in analogy to Intermediate 8a, starting from Intermediate 7d. LCMS (A): $t_R$=1.11 min; $[M+H]^+$=558.19

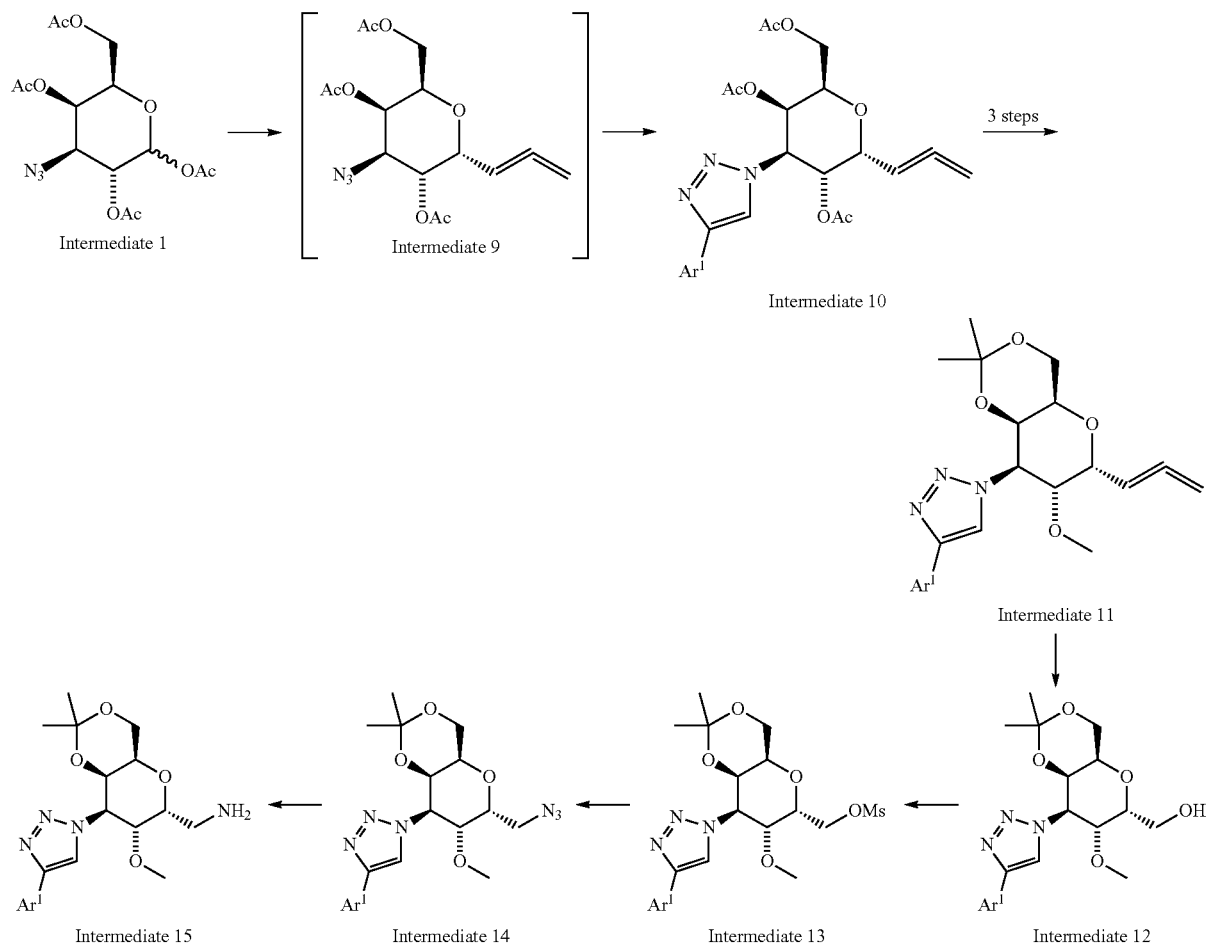

Intermediate 9: (2R,3R,4R,5R,6R)-2-(acetoxymethyl)-6-(propa-1,2-dien-1-yl)-4-(214-triaza-1,2-dien-1-yl)tetrahydro-2H-pyran-3,5-diyl diacetate Intermediate 1 (3733 mg, 10 mmol, 1 eq) is dissolved in MeCN (20 mL) and cooled to 3° C. Trimethyl(propargyl)silane (3.73 mL, 25 mmol, 2.5 eq) is added followed by BF$_3$Oet$_2$ (3.7 mL, 30 mmol, 3 eq) and trimethylsilyl trifluoromethanesulfonate (3.66 mL, 20 mmol, 2 eq) dropwise. The mixture is stirred at 0° C. for 1.5 h and at rt for 1 h. Mixture is partitioned between TBME and sat NaHCO$_3$. The org. phase is washed with brine, dried over MgSO$_4$ and concentrated. The crude product is purified by FC (hept/EA 2:1) to give the desired allene intermediate as a yellowish oil.

$^1$H NMR (500 MHz, DMSO-D6) δ: 5.56 (q, J=6.7 Hz, 1H), 5.35 (d, J=2.2 Hz, 1H), 4.98-5.05 (m, 3H), 4.74 (m, 1H), 4.35 (dd, J$^1$=3.3 Hz, J$^2$=11.2 Hz, 1H), 4.20-4.23 (m, 1H), 4.00-4.03 (m, 1H), 3.90 (dd, J$^1$=7.0 Hz, J$^2$=11.4 Hz, 1H), 2.12 (s, 3H), 2.09 (s, 3H), 2.00-2.02 (m, 4H).

Intermediate 10a: (2R,3R,4R,5R,6R)-2-(acetoxymethyl)-6-(propa-1,2-dien-1-yl)-4-(4-(3,4,5-trifluorophenyl)-1H-1,2,3-triazol-1-yl)tetrahydro-2H-pyran-3,5-diyl diacetate The title compound is prepared in analogy to Intermediate 3a, starting from Intermediate 9. LCMS (A): t$_R$=1.02 min; [M+H]$^+$=510.24

$^1$H NMR (500 MHz, DMSO-d6) δ: 8.81 (s, 1H), 7.82-7.86 (m, 2H), 5.80 (q, J=6.8 Hz, 1H), 5.65-5.72 (m, 2H), 5.40 (d, J=1.5 Hz, 1H), 5.06 (dd, J$^1$=6.6 Hz, J$^2$=2.3 Hz, 2H), 4.96-4.99 (m, 1H), 4.50 (t, J=6.3 Hz, 1H), 4.01 (m, 2H), 2.00-2.04 (m, 6H), 1.87 (s, 3H).

Intermediate 11a: 1-((4aR,6R,7R,8R,8aR)-7-methoxy-2,2-dimethyl-6-(propa-1,2-dien-1-yl)hexahydropyrano[3,2-d][1,3]dioxin-8-yl)-4-(3,4,5-trifluorophenyl)-1H-1,2,3-triazole The title intermediate is prepared starting from Intermediate 10a and following the procedures of Intermediates 4a, 5a and 6a. LCMS (A): t$_R$=1.02 min; [M+H]$^+$=438.21

$^1$H NMR (500 MHz, DMSO-d6) δ: 8.71 (s, 1H), 7.87 (dd, J$^1$=6.8 Hz, J$^2$=9.0 Hz, 2H), 5.75 (m, 1H), 5.13 (dd, J$^1$=3.3 Hz, J$^2$=11.4 Hz, 1H), 5.07 (m, 1H), 4.98 (m, 2H), 4.34-4.34 (m, 1H), 4.26 (dd, J$^1$=5.6 Hz, J$^2$=11.5 Hz, 1H), 4.04 (dd, J$^1$=2.0 Hz, J$^2$=12.9 Hz, 1H), 3.82 (d, J=0.7 Hz, 1H), 3.68 (dd, J$^1$=1.5 Hz, J$^2$=12.9 Hz, 1H), 3.22 (s, 3H), 1.32 (s, 3H), 1.21 (s, 3H).

Intermediate 12a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl)methanol Intermediate 11a (1000 mg, 2.29 mmol, 1 eq) is dissolved in DCM/MeOH 4:1 (60 mL) and cooled to −70° C. Ozone is bubbled through the solution until the KI solution in the scrubber turned brown (~60 min). Excess $O_3$ is purged by bubbling $N_2$ through for 10 min. $NaBH_4$ (86.5 mg, 2.29 mmol, 1 eq) is added at −78° C., the dry ice bath is removed and the mixture is allowed to warm up to rt within 1h. The mixture is then carefully quenched with water (25 mL), the layers are separated, the org. layer is dried over $MgSO_4$ and concentrated under reduced pressure.

The crude solid is purified by FC using CombiFlash (24 g $SiO_2$ column; gradient from hept/EA 2/1 to 100% EA in 20 min) to give the title intermediate as a colourless solid. LCMS (A): $t_R$=0.84 min; $[M+H]^+$=430.29

$^1$H NMR (500 MHz, DMSO-d6) δ: 8.69 (s, 1H), 7.86 (m, 2H), 5.29 (dd, $J^1$=11.4 Hz, $J^2$=3.4 Hz, 1H), 4.80 (t, J=5.5 Hz, 1H), 4.34 (m, 2H), 4.24 (dd, $J^1$=11.4 Hz, $J^2$=6.1 Hz, 1H), 3.96-4.07 (m, 2H), 3.91 (s, 1H), 3.71 (dd, $J^1$=12.7 Hz, $J^2$=1.4 Hz, 1H), 3.63 (ddd, $J^1$=12.3 Hz, $J^2$=5.8 Hz, $J^3$=2.9 Hz, 1H), 3.23 (s, 3H), 1.32 (s, 3H), 1.20 (s, 3H).

Intermediate 13a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl) methyl methanesulfonate Intermediate 12a (400 mg, 0.932 mmol, 1 eq) is dissolved in DCM (8 mL) and cooled to 0° C. At this temperature MsCl (0.0736 mL, 0.932 mmol, 1 eq) and DIPEA (0.191 mL, 1.12 mmol, 1.2 eq) are added and the mixture is stirred at 0° C. for 30 min. More MsCl (0.0144 mL, 0.186 mmol, 0.2 eq) is added and the mixture is stirred at 0° C. for further 30 min. The mixture is diluted with DCM and washed with water. The org. layer is dried over a phase separator and concentrated under reduced pressure. The crude foam is purified by FC using CombiFlash (12 g $SiO_2$ column; gradient from hept to hept/EA 1/2 in 16 min) to give the desired intermediate as a colourless solid. LCMS (A): $t_R$=0.96 min; $[M+H]^+$=508.14

$^1$H NMR (500 MHz, DMSO-d6) δ: 8.72-8.74 (m, 1H), 7.83-7.90 (m, 2H), 5.18-5.27 (m, 1H), 4.89-4.98 (m, 1H), 4.75-4.84 (m, 1H), 4.27-4.37 (m, 3H), 4.06-4.09 (m, 1H), 3.83 (s, 1H), 3.73 (dd, $J^1$=12.9 Hz, $J^2$=1.5 Hz, 1H), 3.26 (d, J=6.1 Hz, 6H), 1.34 (s, 3H), 1.22 (s, 3H).

Intermediate 14a: 1-((4aR,6R,7R,8R,8aR)-6-(azidomethyl)-7-methoxy-2,2-dimethylhexahydropyrano[3,2-d][1,3]dioxin-8-yl)-4-(3,4,5-trifluorophenyl)-1H-1,2,3-triazole To a solution of Intermediate 13a (409 mg, 0.806 mmol, 1 eq) in dry DMF (10 mL) under $N_2$ is added sodium azide (62.9 mg, 0.967 mmol, 1.2 eq). The reaction mixture is heated at 70° C. for 5 h. The temperature is increased to 80° C. and the mixture stirred at this temperature until completion of the reaction. The mixture is allowed to cool to rt, diluted with EA and water and the layers are separated. The aq. layer is extracted once more with EA. The combined org. layers are washed twice with water, brine, dried over $MgSO_4$, filtered and concentrated under reduced pressure. The crude colorless solid is purified by FC using CombiFlash (12 g $SiO_2$ column; gradient: hept to hept/EA 1/1 in 17 min) to give the desired intermediate as a colourless solid. LCMS (A): $t_R$=1.01 min; $[M+H]^+$=455.19

$^1$H NMR (500 MHz, DMSO) δ: 8.68-8.74 (m, 1H), 7.82-7.91 (m, 2H), 5.13-5.23 (m, 1H), 4.67-4.74 (m, 1H), 4.27-4.33 (m, 2H), 4.17-4.25 (m, 1H), 4.05-4.12 (m, 1H), 3.78-3.86 (m, 1H), 3.66-3.74 (m, 1H), 3.23-3.26 (m, 1H), 3.22 (s, 3H), 1.34 (s, 3H), 1.23 (s, 3H).

Intermediate 15a: ((4aR,6R,7R,8R,8aR)-7-methoxy-2,2-dimethyl-8-(4-(3,4,5-trifluorophenyl)-1H-1,2,3-triazol-1-yl)hexahydropyrano[3,2-d][1,3]dioxin-6-yl) methanamine To a solution of Intermediate 14a (500 mg, 1.1 mmol, 1 eq) in THF (7.5 mL) is added $PPh_3$ (583 mg, 2.2 mmol, 2 eq) and water (1.5 mL). The resulting mixture is then heated under $N_2$ at 60° C. for 3h. The mixture is diluted with EA and is then extracted with 10% citric acid (3 times) until all amine is removed from org phase. The combined aq. layers are once more extracted with EA and are then basified with aq. sat. $NaHCO_3$. The basic aq. layer is extracted twice with EA. The combined org. layers are dried over $MgSO_4$, filtered and concentrated under reduced pressure. Used as such.

LCMS (A): $t_R$=0.72 min; $[M+H]^+$=429.09

$^1$H NMR (500 MHz, DMSO) δ: 8.42-8.90 (m, 1H), 7.77-7.89 (m, 2H), 5.09 (dd, $J^1$=11.4 Hz, $J^2$=3.4 Hz, 1H), 4.27-4.31 (m, 2H), 4.23 (m, 1H), 3.99-4.03 (m, 1H), 3.74 (dd, $J^1$=1.5 Hz, $J^2$=12.8 Hz, 1H), 3.68 (s, 1H), 3.21 (s, 3H), 3.11 (dd, $J^1$=13.8 Hz, $J^2$=10.5 Hz, 1H), 2.67 (dd, $J^1$=13.8 Hz, $J^2$=3.4 Hz, 1H), 1.32 (s, 3H).

All further analogs of Intermediates 3-15 with different $Ar^1$-substituents have been prepared in analogy to above procedures starting from known or commercially available substituted aryl acetylenes.

The following most important analogs of Intermediates of 6, 8, 14 and 15 were namely prepared and used in the synthesis of final examples:

| Intermediate | Compound | $t_R$ [min] (LC-MS method A) | MS Data m/z [M + H]+ |
|---|---|---|---|
| 6e | 1-((4aR,6R,7R,8R,8aR)-6-allyl-7-methoxy-2,2-dimethylhexahydropyrano[3,2-d][1,3]dioxin-8-yl)-4-(3,5-difluoro-4-methylphenyl)-1H-1,2,3-triazol | 1.04 | 436.23 |
| 6f | 1-((4aR,6R,7R,8R,8aR)-6-allyl-7-methoxy-2,2-dimethylhexahydropyrano[3,2-d][1,3]dioxin-8-yl)-4-(4-chloro-3,5-difluorophenyl)-1H-1,2,3-triazole | 1.06 | 456.16 |
| 6g | ((2R,3R,4R,5R,6R)-3-acetoxy-6-allyl-4-(4-(3,5-difluoro-4-methylphenyl)-1H-1,2,3-triazol-1-yl)-5-methoxytetrahydro-2H-pyran-2-yl)methyl acetate | 1.03 | 480.16 |
| 6h | ((2R,3R,4R,5R,6R)-3-acetoxy-6-allyl-4-(4-(4-chloro-3,5-difluorophenyl)-1H-1,2,3-triazol-1-yl)-5-methoxytetrahydro-2H-pyran-2-yl)methyl acetate | 1.05 | 500.07 |
| 6i | 1-((4aR,6R,7R,8R,8aR)-6-allyl-7-methoxy-2,2-dimethylhexahydropyrano[3,2-d][1,3]dioxin-8-yl)-4-(3-fluoro-4-methylphenyl)-1H-1,2,3-triazole | 1.00 | 418.25 |
| 6j | 1-((4aR,6R,7R,8R,8aR)-6-allyl-7-methoxy-2,2-dimethylhexahydropyrano[3,2-d][1,3]dioxin-8-yl)-4-(2,3-difluoro-4-methylphenyl)-1H-1,2,3-triazole | 1.06 | 436.25 |

-continued

| Intermediate | Compound | t_R [min] (LC-MS method A) | MS Data m/z [M + H]+ |
|---|---|---|---|
| 6k | 1-((4aR,6R,7R,8R,8aR)-6-allyl-7-methoxy-2,2-dimethylhexahydropyrano[3,2-d][1,3]dioxin-8-yl)-4-(4-chloro-2,3-difluorophenyl)-1H-1,2,3-triazole | 1.08 | 456.17 |
| 6l | 1-((4aR,6R,7R,8R,8aR)-6-allyl-7-methoxy-2,2-dimethylhexahydropyrano[3,2-d][1,3]dioxin-8-yl)-4-(4-bromo-2,3-difluorophenyl)-1H-1,2,3-triazole | 1.06 | 500.10 |
| 6m | 1-((4aR,6R,7R,8R,8aR)-6-allyl-7-methoxy-2,2-dimethylhexahydropyrano[3,2-d][1,3]dioxin-8-yl)-4-(4-chloro-3-fluorophenyl)-1H-1,2,3-triazole | 1.02 | 438.16 |
| 6n | 1-((4aR,6R,7R,8R,8aR)-6-allyl-7-methoxy-2,2-dimethylhexahydropyrano[3,2-d][1,3]dioxin-8-yl)-4-(2,3,4-trifluorophenyl)-1H-1,2,3-triazole | 1.02 | 440.20 |
| 6o | (4aR,6R,7R,8S,8aR)-6-allyl-8-(4-(2,3-difluoro-4-methylphenyl)-1H-1,2,3-triazol-1-yl)-2,2-dimethylhexahydropyrano[3,2-d][1,3]dioxin-7-yl acetate | 1.05 | 464.20 |
| 6p | 1-((4aR,6R,7R,8R,8aR)-6-allyl-7-methoxy-2,2-dimethylhexahydropyrano[3,2-d][1,3]dioxin-8-yl)-4-(3-chloro-4,5-difluorophenyl)-1H-1,2,3-triazole | 1.05 | 456.21 |
| 6q | 1-((4aR,6R,7R,8R,8aR)-6-allyl-7-methoxy-2,2-dimethylhexahydropyrano[3,2-d][1,3]dioxin-8-yl)-4-(2,5-difluoro-4-methylphenyl)-1H-1,2,3-triazole | 1.04 | 436.21 |
| 6r | 4-(1-((4aR,6R,7R,8R,8aR)-6-allyl-7-methoxy-2,2-dimethylhexahydropyrano[3,2-d][1,3]dioxin-8-yl)-1H-1,2,3-triazol-4-yl)-2,6-difluorobenzonitrile | 1.03 | 447.22 |
| 6s | 4-(1-((4aR,6R,7R,8R,8aR)-6-allyl-7-methoxy-2,2-dimethylhexahydropyrano[3,2-d][1,3]dioxin-8-yl)-1H-1,2,3-triazol-4-yl)-2,3-difluorobenzonitrile | 1.03 | 452.24 |
| 6t | 1-((4aR,6R,7R,8R,8aR)-6-allyl-7-methoxy-2,2-dimethylhexahydropyrano[3,2-d][1,3]dioxin-8-yl)-4-(2,3-difluoro-4-methoxyphenyl)-1H-1,2,3-triazole | 1.01 | 452.24 |
| 8e | ((2R,3R,4R,5R,6R)-3-acetoxy-6-(2-(hydroxyimino)ethyl)-5-methoxy-4-(4-(3,4,5-trifluorophenyl)-1H-1,2,3-triazol-1-yl)tetrahydro-2H-pyran-2-yl)methyl acetate | 0.89 | 501.16 |
| 8f | ((2R,3R,4R,5R,6R)-3-acetoxy-4-(4-(3,5-difluoro-4-methylphenyl)-1H-1,2,3-triazol-1-yl)-6-(2-(hydroxyimino)ethyl)-5-methoxytetrahydro-2H-pyran-2-yl)methyl acetate | 0.89 | 497.11 |
| 8g | ((2R,3R,4R,5R,6R)-3-acetoxy-4-(4-(4-chloro-3,5-difluorophenyl)-1H-1,2,3-triazol-1-yl)-6-(2-(hydroxyimino)ethyl)-5-methoxytetrahydro-2H-pyran-2-yl)methyl acetate | 0.91 | 517.01 |
| 8h | 2-((4aR,6R,7R,8R,8aR)-8-(4-(3-fluorophenyl)-1H-1,2,3-triazol-1-yl)-7-methoxy-2,2-dimethylhexahydropyrano[3,2-d][1,3]dioxin-6-yl)acetaldehyde oxime | 0.81 | 421.12 |
| 8i | 2-((4aR,6R,7R,8R,8aR)-8-(4-(4-chloro-3-fluorophenyl)-1H-1,2,3-triazol-1-yl)-7-methoxy-2,2-dimethylhexahydropyrano[3,2-d][1,3]dioxin-6-yl)acetaldehyde oxime | 0.88 | 455.07 |
| 8j | 2-((4aR,6R,7R,8R,8aR)-8-(4-(3,5-difluorophenyl)-1H-1,2,3-triazol-1-yl)-7-methoxy-2,2-dimethylhexahydropyrano[3,2-d][1,3]dioxin-6-yl)acetaldehyde oxime | 0.85 | 439.10 |
| 8k | 2-((4aR,6R,7R,8R,8aR)-8-(4-(4-bromo-3-fluorophenyl)-1H-1,2,3-triazol-1-yl)-7-methoxy-2,2-dimethylhexahydropyrano[3,2-d][1,3]dioxin-6-yl)acetaldehyde oxime | 0.89 | 500.99 |
| 8l | 2-((4aR,6R,7R,8R,8aR)-8-(4-(3,5-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.18 |
| 8m | 2-((4aR,6R,7R,8R,8aR)-8-(4-(3-fluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.86 | 435.18 |
| 8n | 2-((4aR,6R,7R,8R,8aR)-8-(4-(4-chloro-2,3-difluorophenyl)-1H-1,2,3-triazol-1-yl)-7-methoxy-2,2-dimethylhexahydropyrano[3,2-d][1,3]dioxin-6-yl)acetaldehyde oxime | 0.93 | 473.19 |
| 8o | 2-((4aR,6R,7R,8R,8aR)-8-(4-(4-bromo-2,3-difluorophenyl)-1H-1,2,3-triazol-1-yl)-7-methoxy-2,2-dimethylhexahydropyrano[3,2-d][1,3]dioxin-6-yl)acetaldehyde oxime | 0.93 | 519.14 |
| 8p | 2-((4aR,6R,7R,8R,8aR)-8-(4-(4-chloro-3,5-difluorophenyl)-1H-1,2,3-triazol-1-yl)-7-methoxy-2,2-dimethylhexahydropyrano[3,2-d][1,3]dioxin-6-yl)acetaldehyde oxime | 0.92 | 473.12 |
| 8q | 2-((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.19 |
| 8r | 2-((4aR,6R,7R,8R,8aR)-8-(4-(3-chloro-5-fluorophenyl)-1H-1,2,3-triazol-1-yl)-7-methoxy-2,2-dimethylhexahydropyrano[3,2-d][1,3]dioxin-6-yl)acetaldehyde oxime | 0.89 | 455.19 |

-continued

| Intermediate | Compound | $t_R$ [min] (LC-MS method A) | MS Data m/z [M + H]+ |
|---|---|---|---|
| 8s | (4aR,6R,7R,8S,8aR)-8-(4-(2,3-difluoro-4-methylphenyl)-1H-1,2,3-triazol-1-yl)-6-(2-(hydroxyimino)ethyl)-2,2-dimethylhexahydropyrano[3,2-d][1,3]dioxin-7-yl acetate | 0.91 | 481.21 |
| 8t | 2-((4aR,6R,7R,8R,8aR)-7-methoxy-2,2-dimethyl-8-(4-(2,3,4-trifluorophenyl)-1H-1,2,3-triazol-1-yl)hexahydropyrano[3,2-d][1,3]dioxin-6-yl)acetaldehyde oxime | 0.88 | 457.19 |
| 8u | 2-((4aR,6R,7R,8R,8aR)-8-(4-(3-chloro-4,5-difluorophenyl)-1H-1,2,3-triazol-1-yl)-7-methoxy-2,2-dimethylhexahydropyrano[3,2-d][1,3]dioxin-6-yl)acetaldehyde oxime | 0.92 | 473.18 |
| 8v | 2-((4aR,6R,7R,8R,8aR)-8-(4-(2,5-difluoro-4-methylphenyl)-1H-1,2,3-triazol-1-yl)-7-methoxy-2,2-dimethylhexahydropyrano[3,2-d][1,3]dioxin-6-yl)acetaldehyde oxime | 0.89 | 453.23 |
| 14c | 1-((4aR,6R,7R,8R,8aR)-6-(azidomethyl)-7-methoxy-2,2-dimethylhexahydropyrano[3,2-d][1,3]dioxin-8-yl)-4-(4-chloro-2,3-difluorophenyl)-1H-1,2,3-triazole | 1.06 | 471.17 |
| 15b | ((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methanamine | 0.70 | 425.31 |
| 15c | ((4aR,6R,7R,8R,8aR)-8-(4-(4-chloro-2,3-difluorophenyl)-1H-1,2,3-triazol-1-yl)-7-methoxy-2,2-dimethylhexahydropyrano[3,2-d][1,3]dioxin-6-yl)methanamine | 0.71 | 445.18 |

B—Preparation of Examples

General Procedure A: Cycloadditions of Nitrile Oxides with Alkenes

A solution of oxime intermediate (1 eq) and NCS (1.5 eq) in DMF (5 mL/mmol) is stirred at rt until complete conversion to hydroximoyl chloride. Alkene (1-3 eq) and DIPEA or 2,6-lutidine (3 eq) are added and the mixture stirred at rt or 50° C. until complete conversion of intermediate. The products are isolated after aqueous workup (dil. HCl/EA) and purified as described in the general methods.

General procedure B: Deprotection with aq. AcOH

The protected intermediate (acetal and/or silyl Pg) (1 eq) is refluxed in AcOH/H$_2$O 1:1 (5 ml/mmol) until completion of reaction. The products are purified as described in the general methods.

General Procedure C: Acetate Deprotection with K$_2$CO$_3$ in MeOH

K$_2$CO$_3$ (0.1 eq) is added to the acetate protected intermediate (1 eq) in MeOH (5 mL/mmol) and stirred at rt until completion of reaction. The products are purified as described in the general methods.

General Procedure D: Boc Deprotection with TFA

TFA (10-20 eq) is added to a solution of Boc-protected intermediate (1 eq) in DCM (5 mL/mmol). The mixture is stirred at rt until complete conversion. Volatiles are removed under reduced pressure and the residue partitioned between DCM and dil. NH$_4$OH solution. The org. phase is dried over MgSO$_4$ and concentrated in vacuo. If necessary, the product is further purified as described in the general methods General Procedure E: Boc Deprotection with HCl A solution of Boc-protected amine (1 eq) in dioxane (5 mL/mmol) is treated with a solution of HCl in dioxane (4 M, 10-20 eq) and the resulting mixture is stirred at rt until completion of reaction. Volatiles are removed under reduced pressure and the crude product isolated by trituration with TBME.

General Procedure F: Schotten Baumann Acylation

Acyl chloride or anhydride (1.2 eq) is added at 0° C. to a biphasic mixture of amine (1 eq) in DCM (5 mL/mmol) and sat. NaHCO$_3$ solution (5 mL/mmol) under vigorous stirring. The mixture is further stirred at rt until complete conversion. The phases are separated and the org. phase dried over MgSO$_4$ and concentrated. The product is purified as described in the general methods.

General Procedure G: Derivatization with Sulfonyl Chlorides, Chloroformates or Isocyanates The electrophile (sulfonyl chloride, chloroformate or isocyanate, 1.1 eq) is added to a mixture of starting amine (1 eq, either free base or as TFA or HCl salt) in DCM (5 mL/mmol) and a base (NEt$_3$ or DIPEA, 5 eq) at 0° C. or rt. The mixture is stirred at rt until completion of reaction. The product is purified as described in the general methods.

General Procedure H: Reductive Amination.

A mixture of amine intermediate (1 eq) and aldehyde BB or ketone (1-2 eq) in DCM is treated with NaBH(OAc)$_3$ (3 eq) and the mixture stirred at rt until complete conversion. After aqueous workup (DCM/dil. NH$_4$OH) the desired products are isolated as described in the general methods.

General Procedure I: Saponification

The ester (1 eq) in THF/H$_2$O 1:1 or THF/MeOH/H$_2$O 3:2:1 (1 mL/mmol) and LiOH·H$_2$O (1.5-3 eq) are stirred at rt until completion of reaction. After aqueous workup (EA/H$_2$O), the product is purified as described in the general methods.

General Procedure J: Wittig Olefination

To a suspension of Methyltriphenylphosphonium bromide 98% (1.05eq) in Et$_2$O dry (1.5 mL/mmol) under N$_2$ at 0° C. is dropwise added n-Butyllithium solution 1.6 M in hexanes (1.05 eq) within 15 min while the temperature is kept below 5° C. The resulting suspension is stirred rt for 1h. Then is dropwise added a solution of the ketone (1eq) in Et$_2$O dry (1 mL/mmol) within 15 min. The resulting suspension is stirred at rt until completion of the reaction. The mixture is carefully quenched with water (2 drops), Et$_2$O (1.5 mL/mmol) is added and the suspension is filtered and washed with Et$_2$O. The filtrate is concentrated under reduced pressure and the residue stored in the freezer.

General Procedure K: Ketone Reduction with NaBH$_4$

The ketone (1eq) is dissolved in EtOH (11 mL/mmol) and THF (6 mL/mmol) and cooled to 0° C. NaBH$_4$ (2eq) is added and the mixture stirred at 0° C. until completion conversion of the reaction. The mixture is diluted with EA and water, acidified by addition of 1N HCl. The phases are separated and org phase is washed with water, and brine, dried over MgSO$_4$ and concentrated. The product is purified as described in the general methods.

General Procedure L. Epoxide Opening with Amines

A solution of epoxide (1.1 eq) and amine (1eq) in MeOH (10 ml/mmol) is heated at reflux in a sealed vial until completion of the reaction. The mixture is concentrated in vacuo and purified as described in the general methods.

General Procedure M: Cyclisation with Triphosgene

A solution of triphosgene (1 eq) in DCM (5 ml/mmol) is added to a solution of amino alcohol (1 eq) and DIPEA (10eq) in DCM (10 ml/mmol) at rt. The mixture is stirred at rt until completion of reaction. After aqueous workup (DCM/sat NaHCO$_3$) the compound is purified as described in the general methods.

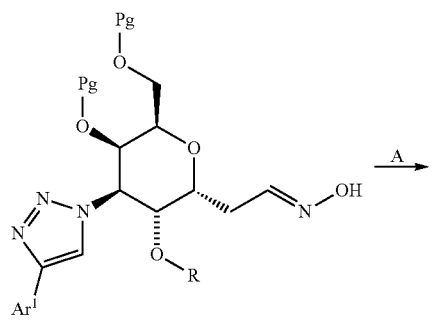

Intermediate 8

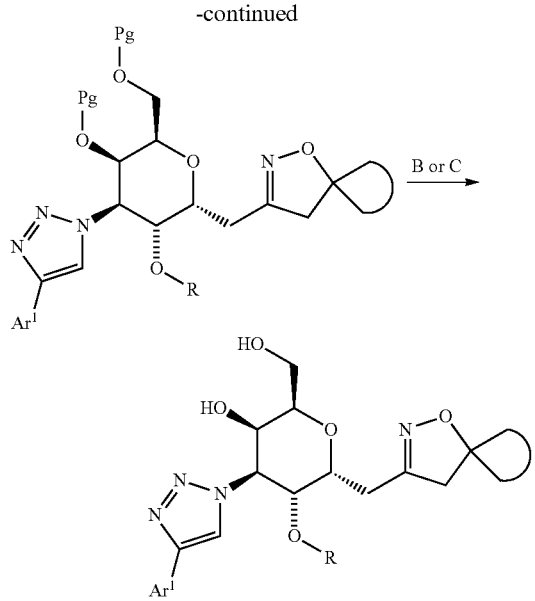

Compounds of Examples 1.01-1.82 listed in Table 1 below are prepared starting from intermediate 8 by applying General procedure A to the appropriate exocyclic methylene derivative (either commercially available or prepared from the corresponding cyclic ketone by Wittig olefination (general procedure J), followed by deprotection according to General Procedure C or D. Diastereomers are separated by chiral preparative chromatography using the appropriate method listed above.

TABLE 1

| Ex. | Compound | $t_R$ [min] (LC-MS method A) | MS Data m/z [M + H]+ |
| --- | --- | --- | --- |
| 1.01 | (2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate | 0.81 | 537.23 |
| 1.02 | (2R,3R,4R,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-6-(hydroxymethyl)tetrahydro-2H-pyran-3,5-diol | 0.69 | 495.21 |
| 1.03 | (2R,3R,4S,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate | 0.93 | 571.26 |
| 1.04 | (2R,3R,4R,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-6-(hydroxymethyl)tetrahydro-2H-pyran-3,5-diol | 0.83 | 529.24 |
| 1.05 | (2R,3R,4R,5R,6R)-2-((1-oxa-2-azaspiro[4.5]dec-2-en-3-yl)methyl)-6-(hydroxymethyl)-4-(4-(3,4,5-trifluorophenyl)-1H-1,2,3-triazol-1-yl)tetrahydro-2H-pyran-3,5-diol | 0.81 | 497.16 |
| 1.06 | tert-butyl 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-ene-8-carboxylate | 0.94 | 612.00 |
| 1.07 | (2R,3R,4S,5R,6R)-6-((1-oxa-2,8-diazaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.64 | 512.16 |
| 1.08 | (2R,3R,4S,5R,6R)-6-((1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 | 511.18 |
| 1.09 | (2R,3R,4S,5R,6R)-6-((1-oxa-2-azaspiro[4.4]non-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.88 | 497.19 |
| 1.10 | (2R,3R,4S,5R,6R)-6-((5-oxa-6-azaspiro[3.4]oct-6-en-7-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.85 | 483.13 |

TABLE 1-continued

| Ex. | Compound | t_R [min] (LC-MS method A) | MS Data m/z [M + H]+ |
|---|---|---|---|
| 1.11 | tert-butyl (3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate (mixture of epimers) | 0.93 | 626.27 |
| 1.12 | (2R,3R,4S,5R,6R)-6-((1-oxa-2-azaspiro[4.5]dec-2-en-yl)methyl)-4-(4-(4-chloro-3-fluorophenyl)-1H-1,2,3-triazol-1-yl)-2-(hydroxymethyl)-5-methoxytetrahydro-2H-pyran-3-ol | 0.92 | 509.24 |
| 1.13 | (2R,3R,4S,5R,6R)-6-((1-oxa-2-azaspiro[4.5]dec-2-en-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.91 | 511.26 |
| 1.14 | (2R,3R,4S,5R,6R)-6-((1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.92 | 507.31 |
| 1.15 | tert-butyl ((5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate (separation of Example 1.11) | 0.93 | 626.24 |
| 1.16 | tert-butyl ((5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate (separation of Example 1.11) | 0.94 | 626.29 |
| 1.17 | (2R,3R,4S,5R,6R)-6-((1-oxa-2-azaspiro[4.5]dec-2-en-3-yl)methyl)-4-(4-(4-bromo-2,3-difluorophenyl)-1H-1,2,3-triazol-1-yl)-2-(hydroxymethyl)-5-methoxytetrahydro-2H-pyran-3-ol | 0.96 | 573.08 |
| 1.18 | (2R,3R,4S,5R,6R)-6-((1-oxa-2-azaspiro[4.5]dec-2-en-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol | 0.96 | 527.20 |
| 1.19 | (2R,3R,4S,5R,6R)-6-((1-oxa-2-azaspiro[4.5]dec-2-en-3-yl)methyl)-4-(4-(3-chloro-5-fluorophenyl)-1H-1,2,3-triazol-1-yl)-2-(hydroxymethyl)-5-methoxytetrahydro-2H-pyran-3-ol | 0.94 | 509.24 |
| 1.20 | (2R,3R,4S,5R,6R)-6-((1-oxa-2-azaspiro[4.5]dec-2-en-3-yl)methyl)-4-(4-(3-fluoro-4-methylphenyl)-1H-1,2,3-triazol-1-yl)-2-(hydroxymethyl)-5-methoxytetrahydro-2H-pyran-3-ol | 0.91 | 489.32 |
| 1.21 | (2R,3R,4S,5R,6R)-6-((1-oxa-2-azaspiro[4.5]dec-2-en-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol | 0.94 | 507.25 |
| 1.22 | (2R,3R,4S,5R,6R)-6-((1-oxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 0.96 | 527.15 |
| 1.23 | (2R,3R,4S,5R,6R)-6-((1,8-dioxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.79 | 513.20 |
| 1.24 | (2R,3R,4S,5R,6R)-6-((8,8-difluoro-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.92 | 547.21 |
| 1.25 | (2R,3R,4S,5R,6R)-2-(hydroxymethyl)-6-((8-isopropyl-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol (mixture of epimers) | 1.05 | 553.27 |
| 1.26 | (2R,3R,4S,5R,6R)-6-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.93 | 543.25 |
| 1.27 | (2R,3R,4S,5R,6R)-2-(hydroxymethyl)-6-(((5r,8R)-8-isopropyl-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol (separation of Example 1.25) | 1.04 | 553.27 |
| 1.28 | (2R,3R,4S,5R,6R)-2-(hydroxymethyl)-6-(((5s,8S)-8-isopropyl-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol (separation of Example 1.25) | 1.05 | 553.27 |
| 1.29 | (2R,3R,4S,5R,6R)-6-((8,8-dimethyl-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 1.00 | 539.25 |
| 1.30 | (2R,3R,4S,5R,6R)-2-(hydroxymethyl)-5-methoxy-6-((8-methyl-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (mixture of epimers) | 0.97 | 526.26 |
| 1.31 | (2R,3R,4S,5R,6R)-6-((1-oxa-2-azaspiro[4.5]dec-2-en-3-yl)methyl)-4-(4-(3-chloro-4,5-difluorophenyl)-1H-1,2,3-triazol-1-yl)-2-(hydroxymethyl)-5-methoxytetrahydro-2H-pyran-3-ol [1-(1,3-di-deoxy-2-O-methyl-3-[4-(3-chloro-4,5-difluorophenyl)-1H-1,2,3-triazol-1-yl]-α-D-galacto-pyranose)-1(1-oxa-2-azaspiro[4.5]dec-2-en-3-yl)-methane] | 0.96 | 527.22 |
| 1.32 | (2R,3R,4S,5R,6R)-6-((7,7-dimethyl-1-oxa-2-azaspiro[4.4]non-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (mixture of epimers) | 0.98 | 525.24 |

TABLE 1-continued

| Ex. | Compound | $t_R$ [min] (LC-MS method A) | MS Data m/z [M + H]+ |
|---|---|---|---|
| 1.33 | (2R,3R,4S,5R,6R)-2-(hydroxymethyl)-5-methoxy-6-(((5r,8R)-8-methyl-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (separation of Example 1.30) | 0.97 | 525.25 |
| 1.34 | (2R,3R,4S,5R,6R)-2-(hydroxymethyl)-5-methoxy-6-(((5s,8S)-8-methyl-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (separation of Example 1.30) | 0.97 | 525.25 |
| 1.35 | (2R,3R,4S,5R,6R)-6-((1,8-dioxa-2-azaspiro[4.5]dec-2-en-3-yl)methyl)-2-(hydroxymethyl)-5-methoxy-4-(4-(2,3,4-trifluorophenyl)-1H-1,2,3-triazol-1-yl)tetrahydro-2H-pyran-3-ol | 0.77 | 513.22 |
| 1.36 | (2R,3R,4S,5R,6R)-6-((1,8-dioxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.79 | 509.22 |
| 1.37 | (2R,3R,4S,5R,6R)-6-((1,8-dioxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol | 0.81 | 529.18 |
| 1.38 | (2R,3R,4S,5R,6R)-6-((1-oxa-2-azaspiro[4.6]undec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol | 0.95 | 525.25 |
| 1.39 | (5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile | 0.85 | 536.19 |
| 1.40 | (5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile [1-(1,3-di-deoxy-2-O-methyl-3-[4-(3,4,5-trifluorophenyl)-1H-1,2,3-triazol-1-yl]-α-D-galacto-pyranose)-1-(trans-8-cyano-1-oxa-2-azaspiro[4.5]dec-2-en-3-yl)-methane] | 0.86 | 536.22 |
| 1.41 | tert-butyl ((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate (separation of Example 1.50) | 0.92 | 626.30 |
| 1.42 | tert-butyl ((5s,8S)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate (separation of Example 1.50) | 0.93 | 626.33 |
| 1.43 | tert-butyl ((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate (separation of Example 1.51) | 0.93 | 622.32 |
| 1.44 | tert-butyl ((5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate (separation of Example 1.51) | 0.94 | 622.33 |
| 1.45 | tert-butyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate (separation of Example 1.49) | 0.95 | 642.26 |
| 1.46 | tert-butyl ((5s,8S)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate (separation of Example 1.49) | 0.96 | 642.29 |
| 1.47 | (2R,3R,4S,5R,6R)-6-((1-oxa-2-azaspiro[4.5]dec-2-en-3-yl)methyl)-4-(4-(2,5-difluoro-4-methylphenyl)-1H-1,2,3-triazol-1-yl)-2-(hydroxymethyl)-5-methoxytetrahydro-2H-pyran-3-ol | 0.92 | 507.28 |
| 1.48 | (2R,3R,4S,5R,6R)-2-(hydroxymethyl)-6-((8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol (mixture of epimers) | 0.83 | 569.24 |
| 1.49 | 3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile (mixture of epimers) | 0.88 | 552.05 |
| 1.50 | 3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile (mixture of epimers) | 0.84 | 536.22 |
| 1.51 | 3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile (mixture of epimers) | 0.84 | 532.10 |
| 1.52 | (2R,3R,4S,5R,6R)-2-(hydroxymethyl)-6-(((5r,8R)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol (separation of Example 1.48) | 0.83 | 569.25 |
| 1.53 | (2R,3R,4S,5R,6R)-2-(hydroxymethyl)-6-(((5s,8S)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol (separation of Example 1.48) | 0.84 | 569.24 |

TABLE 1-continued

| Ex. | Compound | $t_R$ [min] (LC-MS method A) | MS Data m/z [M + H]+ |
|---|---|---|---|
| 1.54 | (2R,3R,4S,5R,6R)-4-(4-(2,3-difluoro-4-methylphenyl)-1H-1,2,3-triazol-1-yl)-2-(hydroxymethyl)-6-((8-(2-hydroxypropan-2-yl)-1-oxa-2-azaspiro[4.5]dec-2-en-3-yl)methyl)-5-methoxytetrahydro-2H-pyran-3-ol (mixture of epimers) | 0.85 | 565.09 |
| 1.55 | (2R,3R,4S,5R,6R)-4-(4-(4-chloro-2,3-difluorophenyl)-1H-1,2,3-triazol-1-yl)-2-(hydroxymethyl)-6-((8-(2-hydroxypropan-2-yl)-1-oxa-2-azaspiro[4.5]dec-2-en-3-yl)methyl)-5-methoxytetrahydro-2H-pyran-3-ol (mixture of epimers) | 0.88 | 585.19 |
| 1.56 | (5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile | 0.86 | 532.24 |
| 1.57 | (5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile | 0.86 | 532.23 |
| 1.58 | (5s,8S)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile | 0.84 | 536.22 |
| 1.59 | (5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile | 0.85 | 536.22 |
| 1.60 | (5s,8S)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile | 0.88 | 552.16 |
| 1.61 | (5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile | 0.88 | 552.17 |
| 1.62 | (2R,3R,4S,5R,6R)-4-(4-(2,3-difluoro-4-methylphenyl)-1H-1,2,3-triazol-1-yl)-2-(hydroxymethyl)-6-(((5r,8R)-8-(2-hydroxypropan-2-yl)-1-oxa-2-azaspiro[4.5]dec-2-en-3-yl)methyl)-5-methoxytetrahydro-2H-pyran-3-ol | 0.84 | 565.09 |
| 1.63 | (2R,3R,4S,5R,6R)-4-(4-(2,3-difluoro-4-methylphenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol | 0.85 | 565.15 |
| 1.64 | (2R,3R,4S,5R,6R)-4-(4-(4-chloro-2,3-difluorophenyl)-1H-1,2,3-triazol-1-yl)-2-(hydroxymethyl)-6-(((5r,8R)-8-(2-hydroxypropan-2-yl)-1-oxa-2-azaspiro[4.5]dec-2-en-3-yl)methyl)-5-methoxytetrahydro-2H-pyran-3-ol | 0.87 | 585.17 |
| 1.65 | (2R,3R,4S,5R,6R)-4-(4-(4-chloro-2,3-difluorophenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol | 0.88 | 585.16 |
| 1.66 | 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-one | 0.8 | 525.19 |
| 1.67 | (2R,3R,4S,5R,6R)-6-((1-oxa-2-azaspiro[4.5]dec-2-en-3-yl)methyl)-5-(2,2-difluoroethoxy)-2-(hydroxymethyl)-4-(4-(3,4,5-trifluorophenyl)-1H-1,2,3-triazol-1-yl)tetrahydro-2H-pyran-3-ol | 0.96 | 562.03 |
| 1.68 | methyl 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate | 0.93 | 569.22 |
| 1.69 | (2R,3R,4S,5R,6R)-6-((1-oxa-2-azaspiro[4.5]dec-2-en-3-yl)methyl)-5-ethoxy-2-(hydroxymethyl)-4-(4-(3,4,5-trifluorophenyl)-1H-1,2,3-triazol-1-yl)tetrahydro-2H-pyran-3-ol | 0.96 | 525.25 |
| 1.70 | 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-N-methylacetamide | 0.84 | 568.21 |
| 1.71 | 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)-1-morpholinoethan-1-one | 0.84 | 624.28 |
| 1.72 | methyl 2-(((2R,3R,4S,5R,6R)-2-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetate | 0.92 | 601.24 |
| 1.73 | (2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl carbamate | 0.82 | 540.22 |
| 1.74 | (2R,3R,4S,5R,6R)-4-(4-(2,3-difluoro-4-methylphenyl)-1H-1,2,3-triazol-1-yl)-6-(((5r,8R)-8-((2,2-difluoroethyl)amino)-1-oxa-2-azaspiro[4.5]dec-2-en-3-yl)methyl)-2-(hydroxymethyl)-5-methoxytetrahydro-2H-pyran-3-ol | 0.65 | 586.23 |
| 1.75 | tert-butyl (RS)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2,8-diazaspiro[4.6]undec-2-ene-8-carboxylate (mixture of epimers) [1-(1,3-di-deoxy-2-O-methyl-3-[4-(2,3-difluoro-4-methylphenyl)-1H-1,2,3-triazol-1-yl]-α-D-galacto-pyranose)-1-(8-(tert-butoxycarbonyl)-1-oxa-2,8-diazaspiro[4.6]undec-2-en-3-yl)-methane] | 0.97 | 622.27 |
| 1.76 | (RS)-3-(2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2,8-diazaspiro[4.6]undec-2-en-9-one (mixture of epimers) | 0.71 | 536.25 |

TABLE 1-continued

| Ex. | Compound | $t_R$ [min] (LC-MS method A) | MS Data m/z [M + H]+ |
|---|---|---|---|
| 1.77 | (RS)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-8-methyl-1-oxa-2,8-diazaspiro[4.6]undec-2-en-9-one (mixture of epimers) | 0.74 | 550.0 |
| 1.78 | (5RS,8S)-7-(tert-butoxycarbonyl)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2,7-diazaspiro[4.4]non-2-ene-8-carboxylic acid (mixture of epimers) | 0.85 | 657.92 |
| 1.79 | tert-butyl (RS)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2,7-diazaspiro[4.4]non-2-ene-7-carboxylate (mixture of epimers) | 0.93 | 614.14 |
| 1.80 | tert-butyl 7-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-5-oxa-2,6-diazaspiro[3.4]oct-6-ene-2-carboxylate | 0.93 | 600.08 |
| 1.81 | (2R,3R,4S,5R,6R)-6-((4'H-spiro[bicyclo[2.2.1]heptane-2,5'-isoxazol]-3'-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.95 | 519.51 |
| 1.82 | (2R,3R,4S,5R,6R)-6-((4'H-spiro[bicyclo[3.2.1]octane-3,5'-isoxazol]-3'-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.97 | 533.13 |

The following examples (Table 2) are prepared starting form oxime intermediates 8 and exocyclic alkenes applying general procedure A, followed by deprotection (procedure B, C, D, E or 1) and subsequent derivatisation following procedures F, G, H or K). Final deprotection (if necessary) is performed following procedures B or C.

TABLE 2

| Ex. | Compound | $t_R$ [min] (LC-MS method A) | MS Data m/z [M + H]+ |
|---|---|---|---|
| 2.01 | 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol (mixture of epimers) | 0.76 | 527.21 |
| 2.02 | (5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol (separation of Example 2.01) | 0.76 | 527.2 |
| 2.03 | (5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol (separation of Example 2.01) | 0.76 | 527.2 |
| 2.04 | N-((5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)acetamide | 0.771 | 568.2 |
| 2.05 | N-((5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)acetamide | 0.78 | 568,21 |
| 2.06 | N-(5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)acetamide | 0.76 | 564.27 |
| 2.07 | N-((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)acetamide | 0.79 | 584.22 |
| 2.08 | N-((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)acetamide | 0.75 | 568.26 |
| 2.09 | ethyl ((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate | 0.87 | 594.27 |
| 2.10 | ethyl ((5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-en-8-yl)carbamate | 0.85 | 598.03 |
| 2.11 | ethyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate | 0.89 | 614.02 |
| 2.12 | (2R,3R,4S,5R,6R)-2-(hydroxymethyl)-6-(((5r,8R)-8-(isopropylamino)-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol | 0.67 | 568.24 |
| 2.13 | (2R,3R,4S,5R,6R)-2-(hydroxymethyl)-6-(((5s,8S)-8-(isopropylamino)-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol | 0.68 | 568.24 |

TABLE 2-continued

| Ex. | Compound | $t_R$ [min] (LC-MS method A) | MS Data m/z [M + H]+ |
|---|---|---|---|
| 2.14 | (2R,3R,4S,5R,6R)-2-(hydroxymethyl)-5-methoxy-6-((8-(pentan-3-ylamino)-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (mixture of epimers) | 0.73 | 596.26 |
| 2.15 | (2R,3R,4S,5R,6R)-6-((8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (mixture of epimers) | 0.66 | 590.2 |
| 2.16 | (2R,3R,4S,5R,6R)-6-((8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (mixture of epimers) | 0.67 | 566.22 |
| 2.17 | (2R,3R,4S,5R,6R)-2-(hydroxymethyl)-5-methoxy-6-((8-((2,2,2-trifluoroethyl)amino)-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (mixture of epimers) | 0.68 | 608.19 |
| 2.18 | 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-one oxime (mixture of E/Z isomers) | 0.77 | 540.17 |
| 2.19 | (2R,3R,4S,5R,6R)-2-(hydroxymethyl)-5-methoxy-6-((8-morpholino-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol (mixture of epimers) | 0.66 | 596.27 |
| 2.20 | (2R,3R,4S,5R,6R)-6-(((5r,8R)-8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (separation of Example 2.15) | 0.84 | 590.10 |
| 2.21 | (2R,3R,4S,5R,6R)-6-(((5s,8S)-8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (separation of Example 2.15) | 0.86 | 590.11 |
| 2.22 | (2R,3R,4S,5R,6R)-6-(((5r,8R)-8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (separation of Example 2.16) | 0.67 | 566.22 |
| 2.23 | (2R,3R,4S,5R,6R)-6-(((5s,8S)-8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol (separation of Example 2.16) | 0.67 | 566.22 |
| 2.24 | 2-(((2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid | 0.69 | 553.2 |
| 2.25 | 2-(((2R,3R,4S,5R,6R)-2-((1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid | 0.81 | 551.23 |
| 2.26 | 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid | 0.82 | 555.19 |
| 2.27 | (2R,3R,4S,5R,6R)-6-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol | 0.82 | 587.24 |
| 2.28 | N-(tert-butyl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-ene-8-carboxamide | 0.86 | 611.19 |
| 2.29 | (2R,3R,4S,5R,6R)-2-(hydroxymethyl)-5-methoxy-6-((8-methyl-1-oxa-2,8-diazaspiro[4.5]dec-2-en-3-yl)methyl)-4-(4-(3,4,5-trifluorophenyl)-1H-1,2,3-triazol-1-yl)tetrahydro-2H-pyran-3-ol | 0.65 | 526.21 |
| 2.30 | 1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-en-8-yl)ethan-1-one | 0.76 | 554.18 |

TABLE 2-continued

| Ex. | Compound | $t_R$ [min] (LC-MS method A) | MS Data m/z [M + H]+ |
|---|---|---|---|
| 2.31 | (2R,3R,4S,5R,6R)-2-(hydroxymethyl)-5-methoxy-6-((8-(methylsulfonyl)-1-oxa-2,8-diazaspiro[4.5]dec-2-en-3-yl)methyl)-4-(4-(3,4,5-trifluorophenyl)-1H-1,2,3-triazol-1-yl)tetrahydro-2H-pyran-3-ol | 0.81 | 590.10 |

The examples of table 3 are prepared starting with amines (Intermediates 15) and epoxides according to General procedure L and M, followed by deprotection (general procedure B or C)

TABLE 3

| Ex. | Compound | $t_R$ [min] (LC-MS method A) | MS Data m/z [M + H]+ |
|---|---|---|---|
| 3.01 | tert-butyl 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxo-1-oxa-3,8-diazaspiro[4.5]decane-8-carboxylate | 0.92 | 628.23 |
| 3.02 | 3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-3-azaspiro[4.5]decan-2-one [1-(1,3-di-deoxy-2-O-methyl-3-[4-(2,3-difluoro-4-methylphenyl)-1H-1,2,3-triazol-1-yl]-α-D-galacto-pyranose)-1(1-oxa-3-azaspiro[4.5]decan-2-on-yl)-methane] | 0.90 | 523.25 |
| 3.03 | 3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,8-dioxa-3-azaspiro[4.5]decan-2-one | 0.76 | 525.23 |

Example 4.01: 3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,3-diazaspiro[4.5]decan-2-one Step 1: tert-butyl (1-(((((4aR,6R,7R,8R,8aR)-8-(4-(2,3-difluoro-4-methylphenyl)-1H-1,2,3-triazol-1-yl)-7-methoxy-2,2-dimethylhexahydropyrano[3,2-d][1,3]dioxin-6-yl)methyl)amino)methyl)cyclohexyl)carbamate Intermediate 15b (300 mg, 0.707 mmol, 1 eq) is dissolved in DCM/MeOH 4:1 (12 mL) and 1-(Boc-amino)-1-formyl-cyclohexane (338 mg, 1.41 mmol, 2 eq), sodium triacetoxyborohydride 97% (237 mg, 1.06 mmol, 1.5 eq) and AcOH (0.0404 mL, 0.707 mmol, 1 eq) is added under $N_2$ at rt. The mixture is stirred at rt until complete conversion. The title intermediate is isolated after aqueous workup (DCM/sat NaHCO$_3$ solution) and column chromatography on silica gel (0-15% MeOH in DCM) as a colourless solid. LCMS (A): $t_R$=0.92 min; [M+H]$^+$=636.32

Step 2: Title Compound

Above intermediate (50 mg) is dissolved in DMF (0.7 ml) and treated with NaH (55% dispersion in mineral oil, 2 eq) at 0° C. The mixture is stirred at rt for 48h, partitioned between EA and water. The org phase is dried over MgSO4 and concentrated. The isolated intermediate is deprotected following general procedure B. LCMS (A): $t_R$=0.86 min; [M+H]$^+$=522.22

Example 4.02: 2-(((2R,3R,4S,5R,6R)-4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-2,4-diazaspiro[5.5]undecan-3-one The title compound is prepared in analogy to Example 4.01 steps 1 and 2, starting from Intermediate 15c and tert-butyl ((1-formylcyclohexyl)methyl)carbamate (CAS 1476035-56-9). LCMS (A): $t_R$=0.91 min; [M+H]$^+$=556.18

Example 4.03: (2R,3R,4S,5R,6R)-4-(4-(2,3-difluoro-4-methylphenyl)-1H-1,2,3-triazol-1-yl)-2-(hydroxymethyl)-5-methoxy-6-((2-methyl-1,3-diazaspiro[4.5]dec-1-en-3-yl)methyl)tetrahydro-2H-pyran-3-ol Step 1: (2R,3R,4S,5R,6R)-6-((((1-aminocyclohexyl)methyl)amino)methyl)-4-(4-(2,3-difluoro-4-methylphenyl)-1H-1,2,3-triazol-1-yl)-2-(hydroxymethyl)-5-methoxytetrahydro-2H-pyran-3-ol Intermediate of Example 4.01, step 1 (200 mg, 0.315 mmol, 1 eq) is dissolved in DCM (3 mL) at rt and 4M HCl in dioxane (3 mL) is added. The white suspension is stirred at rt. Water is added and the aq. phase is basified with 32% NaOH solution, extracted with DCM (3×), dried over MgSO$_4$, filtered and concentrated to dryness and dried at HV to give the title intermediate as a colourless resin which is used without purification. LCMS (A): $t_R$=0.59 min; [M+H]$^+$=496.28

Step 2: (2R,3R,4S,5R,6R)-6-((((1-aminocyclohexyl)methyl)amino)methyl)-2-(((tert-butyldimethylsilyl)oxy)methyl)-4-(4-(2,3-difluoro-4-methylphenyl)-1H-1,2,3-triazol-1-yl)-5-methoxytetrahydro-2H-pyran-3-ol To a solution of above intermediate (130 mg) and NEt$_3$ (0.022 mL, 0.157 mmol, 0.6 eq) in dry DCM (3 mL) is added TBSCI (excess) at 0° C. under nitrogen. The mixture is stirred at rt for 3 days. Water is added and the product extracted with DCM. Chromatography on $SiO_2$ (0-20% MeOH in DCM (+0.5% NH4OH) gave the title intermediate as a colourless solid. LCMS (A): $t_R$=0.83 min; $[M+H]^+$=610.13

Step 3: (2R,3R,4S,5R,6R)-2-(((tert-butyldimethylsilyl)oxy) methyl)-4-(4-(2,3-difluoro-4-methylphenyl)-1H-1,2,3-triazol-1-yl)-5-methoxy-6-((2-methyl-1,3-diazaspiro[4.5]dec-1-en-3-yl)methyl)tetrahydro-2H-pyran-3-ol Intermediate of step 2 (60 mg) is dissolved in dioxane (1 ml) and triethyl orthoacetate (2 eq) is added. The mixture is heated at reflux for 1.5h. The mixture is concentrated in vacuo and dried at hv. LCMS (A): $t_R$=0.98 min; $[M+H]^+$=634.28

Step 4: Title Compound

Intermediate of step 3 is dissolved in THE (2 ml) and TBAF (1M in THF, 1.2 eq) is added. The mixture is stirred at rt for 1h, diluted with water and extracted with EA and DCM. Combined org extracts are dried and concentrated and purified by prep HPLC (prep LC-MS III). LCMS (A): $t_R$=0.75 min; $[M+H]^+$=520.24

Example 4.03: (2R,3R,4S,5R,6R)-6-((1,3-diazaspiro [4.5]dec-1-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol This example is prepared in analogy to Example 4.03, steps 3 and 4 using triethyl orthoformate instead of triethyl orthoacetate. LCMS (A): $t_R$=0.74 min; $[M+H]^+$=506.21

II. Biological Assays sEvaluation of Compound Inhibitory Activity ($IC_{50}$)

The inhibitory activity of compounds is determined in competitive binding assays. This spectrophotometric assay measures the binding of biotinylated human Gal-3 (hGal-3) or human Gal-1 (hGal-1), respectively, to a microplate-adsorbed glycoprotein, asialofetuin (ASF) (Proc Natl Acad Sci USA. 2013 Mar. 26; 110(13):5052-7.). Alternatively, and preferably, a human Gal-1 version in which all six cysteines are substituted by serines may be used.

Briefly, compounds are serially diluted in DMSO (working dilutions). ASF-coated 384 well plates are supplemented with 22.8 µL/well of biotinylated hGal-3 or hGal-1 in assay buffer (i.e. 300-1000 ng/mL biotinylated hGal-3 or hGal-1) to which 1.2 □L of compound working dilutions are added and mixed.

Plates are incubated for 3 hours at 4° C., then washed with cold assay buffer (3×50 uL), incubated for 1 hour with 25 µL/well of a streptavidin-peroxidase solution (diluted in assay buffer to 80 ng/mL) at 4° C., followed by further washing steps with assay buffer (3×50 uL). Finally, 25 L/well of ABTS substrate is added. OD (410 nm) is recorded after 30 to 45 min and $IC_{50}$ values are calculated.

The calculated $IC_{50}$ values may fluctuate depending on the daily assay performance. Fluctuations of this kind are known to those skilled in the art. $IC_{50}$ values from several measurements are given as mean values.

Activity on hGal-3 ($IC_{50}$ in µM)

TABLE 4

| Ex. | Gal-3 $IC_{50}$ | Ex. | Gal-3 $IC_{50}$ | Ex. | Gal-3 $IC_{50}$ | Ex. | Gal-3 $IC_{50}$ |
|---|---|---|---|---|---|---|---|
| 1.01 | 0.061 | 1.02 | 0.084 | 1.03 | 0.079 | 1.04 | 0.17 |
| 1.05 | 0.28 | 1.06 | 0.34 | 1.07 | 0.32 | 1.08 | 0.24 |

TABLE 4-continued

| Ex. | Gal-3 $IC_{50}$ | Ex. | Gal-3 $IC_{50}$ | Ex. | Gal-3 $IC_{50}$ | Ex. | Gal-3 $IC_{50}$ |
|---|---|---|---|---|---|---|---|
| 1.09 | 0.95 | 1.10 | 0.62 | 1.11 | 0.069 | 1.12 | 0.31 |
| 1.13 | 0.14 | 1.14 | 0.078 | 1.15 | 0.035 | 1.16 | 0.34 |
| 1.17 | 0.16 | 1.18 | 0.18 | 1.19 | 0.68 | 1.20 | 0.12 |
| 1.21 | 0.11 | 1.22 | 0.076 | 1.23 | 0.76 | 1.24 | 0.45 |
| 1.25 | 1.3 | 1.26 | 0.11 | 1.27 | 1.1 | 1.28 | 2.0 |
| 1.29 | 0.44 | 1.30 | 0.50 | 1.31 | 0.26 | 1.32 | 0.34 |
| 1.33 | 0.33 | 1.34 | 0.52 | 1.35 | 0.11 | 1.36 | 0.064 |
| 1.37 | 0.12 | 1.38 | 0.16 | 1.39 | 0.26 | 1.40 | 0.089 |
| 1.41 | 0.012 | 1.42 | 0.132 | 1.43 | 0.015 | 1.44 | 0.10 |
| 1.45 | 0.010 | 1.46 | 0.060 | 1.47 | 0.43 | 1.48 | 0.49 |
| 1.49 | 0.11 | 1.50 | 0.16 | 1.51 | 0.10 | 1.52 | 0.26 |
| 1.53 | 0.27 | 1.54 | 0.20 | 1.55 | 0.40 | 1.56 | 0.12 |
| 1.57 | 0.041 | 1.58 | 0.11 | 1.59 | 0.13 | 1.60 | 0.090 |
| 1.61 | 0.049 | 1.62 | 0.19 | 1.63 | 0.18 | 1.64 | 0.49 |
| 1.65 | 0.12 | 1.66 | 0.25 | 1.67 | 0.23 | 1.68 | 0.22 |
| 1.69 | 0.30 | 1.70 | 0.24 | 1.71 | 0.20 | 1.72 | 0.14 |
| 1.73 | 0.11 | 1.74 | 0.12 | 1.75 | 0.16 | 1.76 | 0.11 |
| 1.77 | 0.10 | 1.78 | 0.27 | 1.79 | 0.49 | 1.80 | 0.31 |
| 1.81 | 0.06 | 1.82 | 0.05 | | | | |
| 2.01 | 0.25 | 2.02 | 0.70 | 2.03 | 0.19 | 2.04 | 0.061 |
| 2.05 | 0.45 | 2.06 | 0.071 | 2.07 | 0.062 | 2.08 | 0.052 |
| 2.09 | 0.017 | 2.10 | 0.020 | 2.11 | 0.019 | 2.12 | 0.22 |
| 2.13 | 0.55 | 2.14 | 0.39 | 2.15 | 0.28 | 2.16 | 0.24 |
| 2.17 | 0.21 | 2.18 | 0.32 | 2.19 | 0.39 | 2.20 | 0.11 |
| 2.21 | 0.38 | 2.22 | 0.14 | 2.23 | 0.59 | 2.24 | 0.080 |
| 2.25 | 0.037 | 2.26 | 0.090 | 2.27 | 0.081 | 2.28 | 0.14 |
| 2.29 | 0.38 | 2.30 | 0.28 | 2.31 | 0.53 | | |
| 3.01 | 0.12 | 3.02 | 0.036 | 3.03 | 0.090 | | |
| 4.01 | 0.046 | 4.02 | 0.074 | 4.03 | 0.074 | 4.04 | 0.081 |

Activities on hGal-1 IC50 (µM)

TABLE 5

| Ex. | Gal-1 $IC_{50}$ | Ex. | Gal-1 $IC_{50}$ | Ex. | Gal-1 $IC_{50}$ | Ex. | Gal-1 $IC_{50}$ |
|---|---|---|---|---|---|---|---|
| 1.01 | 4.2 | 1.02 | 5.2 | 1.03 | >100 | 1.04 | 10.4 |
| 1.05 | 2.2 | 1.06 | 4.2 | 1.07 | 5.7 | 1.08 | 1.9 |
| 1.09 | 2.7 | 1.10 | 2.2 | 1.11 | 1.5 | 1.12 | 1.1 |
| 1.13 | 0.52 | 1.14 | 2.1 | 1.15 | 1.1 | 1.16 | 2.3 |
| 1.17 | 6.0 | 1.18 | 10.3 | 1.19 | 4.2 | 1.20 | 5.3 |
| 1.21 | 11.4 | 1.22 | 3.7 | 1.23 | 3.5 | 1.24 | 4.9 |
| 1.25 | 11.1 | 1.26 | 4.0 | 1.27 | 18.8 | 1.28 | 6.9 |
| 1.29 | 2.2 | 1.30 | 3.1 | 1.31 | 0.97 | 1.32 | 3.4 |
| 1.33 | 3.7 | 1.34 | 2.5 | 1.35 | 1.4 | 1.36 | 3.8 |
| 1.37 | 4.6 | 1.38 | 6.4 | 1.39 | 7.1 | 1.40 | 2.0 |
| 1.41 | 0.30 | 1.42 | 0.85 | 1.43 | 1.24 | 1.44 | 4.9 |
| 1.45 | 0.80 | 1.46 | 1.8 | 1.47 | 2.2 | 1.48 | 2.6 |
| 1.49 | 1.2 | 1.50 | 0.57 | 1.51 | 1.9 | 1.52 | 2.8 |
| 1.53 | 1.2 | 1.54 | 5.4 | 1.55 | 4.4 | 1.56 | 3.6 |
| 1.57 | 0.53 | 1.58 | 0.64 | 1.59 | 0.22 | 1.60 | 1.6 |
| 1.61 | 0.46 | 1.62 | 4.6 | 1.63 | 3.4 | 1.64 | 2.4 |
| 1.65 | 2.7 | 1.66 | 2.7 | 1.67 | 2.9 | 1.68 | 3.7 |
| 1.69 | 3.1 | 1.70 | 5.1 | 1.71 | 2.9 | 1.72 | 5.6 |
| 1.73 | 6.5 | 1.74 | 2.4 | 1.75 | 8.2 | 1.76 | 2.7 |
| 1.77 | 4.8 | 1.78 | 12.0 | 1.79 | 4.8 | 1.80 | 7.2 |
| 1.81 | 2.37 | 1.82 | 1.95 | | | | |
| 2.01 | 2.2 | 2.02 | 5.1 | 2.03 | 2.0 | 2.04 | 0.81 |
| 2.05 | 3.6 | 2.06 | 0.34 | 2.07 | 0.91 | 2.08 | 0.31 |
| 2.09 | 0.64 | 2.10 | 0.32 | 2.11 | 0.34 | 2.12 | 2.4 |
| 2.13 | 7.0 | 2.14 | 2.6 | 2.15 | 7.2 | 2.16 | 2.4 |
| 2.17 | 1.4 | 2.18 | 2.9 | 2.19 | 1.7 | 2.20 | 1.8 |
| 2.21 | 1.6 | 2.22 | 1.3 | 2.23 | 1.6 | 2.24 | 6.7 |
| 2.25 | 3.7 | 2.26 | 3.5 | 2.27 | 11.5 | 2.28 | 1.7 |
| 2.29 | 4.8 | 2.30 | 2.8 | 2.31 | 3.5 | | |
| 3.01 | 2.7 | 3.02 | 1.4 | 3.03 | 2.3 | | |
| 4.01 | 1.3 | 4.02 | 0.4 | 4.03 | 1.7 | 4.04 | 1.3 |

The invention claimed is:
1. A compound of Formula (I)

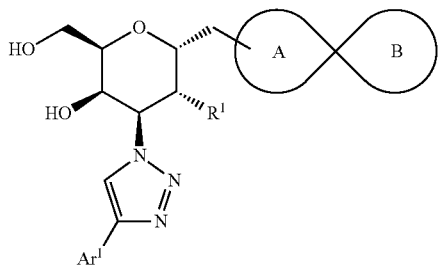

Formula (I)

wherein
Ar$^1$ represents
aryl which is unsubstituted, or mono-, di-, tri-, tetra-, or penta-substituted, wherein the substituents are independently selected from halogen, methyl, cyano, methoxy, trifluoromethyl, and trifluoromethoxy;
5- or 6-membered heteroaryl, wherein said 5- or 6-membered heteroaryl independently is unsubstituted, mono- or di-substituted, wherein the substituents are independently selected from halogen, methyl, cyano, and methoxy; or
9- or 10-membered heteroaryl, wherein said 9- or 10-membered heteroaryl independently is unsubstituted, or mono-substituted with methyl;
R$^1$ represents
hydroxy;
C$_{1-4}$-alkoxy;
—O—CO—C$_{1-3}$-alkyl;
O—CO—NH—R$^{N11}$ wherein R$^{N11}$ represents hydrogen or C$_{1-3}$-alkyl;
—O—CH$_2$—C$_1$-fluoroalkyl; or
—O—CH$_2$—CO—R$^{1X}$ wherein R$^{1X}$ represents
hydroxy;
C$_{1-3}$-alkoxy;
morpholin-4-yl; or
—NR$^{N21}$R$^{N22}$ wherein R$^{N21}$ and R$^{N22}$ both independently represent hydrogen or methyl; and

represents a spirocyclic fragment, wherein:
ring A represents a heterocycloalkylene selected from

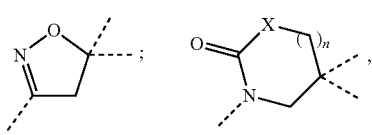

wherein X represents nitrogen or oxygen, and n represents the integer 0 or 1; and wherein in case X represents nitrogen, said nitrogen is unsubstituted or mono-substituted with C$_{1-4}$-alkyl;

and

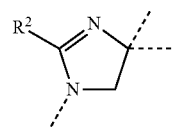

wherein R$^2$ represents hydrogen or C$_{1-4}$-alkyl; and
ring B represents
C$_{4-7}$-cycloalkane-diyl wherein said C$_{4-7}$-cycloalkane-diyl is unsubstituted, mono-, or di-substituted wherein the substituents are independently selected from C$_{1-4}$-alkyl; C$_{1-3}$-fluoroalkyl; C$_{1-4}$-alkoxy; halogen; cyano; oxo; hydroxy; hydroxy-C$_{1-4}$-alkyl; hydroxyimino; morpholin-4-yl; and —NH—R$^{N11}$ wherein R$^{N11}$ represents C$_{1-6}$-alkyl, C$_{2-4}$-alkoxy, C$_{3-6}$-cycloalkyl, C$_{2-3}$-fluoroalkyl, —CO—C$_{1-4}$-alkyl, or —CO—C$_{1-4}$-alkoxy;
4- to 7-membered heterocycloalkane-diyl wherein said heterocycloalkane-diyl contains one ring oxygen atom;
4- to 7-membered heterocycloalkane-diyl wherein said heterocycloalkane-diyl contains one ring nitrogen atom, wherein said ring nitrogen atom is unsubstituted or mono-substituted with C$_{1-4}$-alkyl, —CO—C$_{1-4}$-alkyl, —SO$_2$—C$_{1-4}$-alkyl, —CO—C$_{1-4}$-alkoxy, or —CO—NH—C$_{1-4}$-alkyl; and wherein said 4- to 7-membered heterocycloalkane-diyl carries no further substituent in addition to said substituent on the ring nitrogen atom, or carries one further substituent on a ring carbon atom that is attached to said ring nitrogen atom wherein said substituent is oxo, or —CO—OH; or
bridged bicyclic C$_{6-9}$-cycloalkane-diyl;
or a pharmaceutically acceptable salt thereof.

2. A compound according to claim 1, wherein Ar$^1$ represents phenyl which is di-, or tri-substituted, wherein the substituents are independently selected from halogen, methyl, cyano, methoxy, trifluoromethyl, and trifluoromethoxy;
or a pharmaceutically acceptable salt thereof.

3. A compound according to claim 1, wherein Ar$^1$ represents phenyl which is di- or tri-substituted, wherein the substituents are independently selected from halogen and methyl; wherein at least one of said substituents is attached in a meta- and/or in para-position of said phenyl;
or a pharmaceutically acceptable salt thereof.

4. A compound according to claim 1, wherein R$^1$ represents methoxy;
or a pharmaceutically acceptable salt thereof.

5. A compound according to claim 1, wherein ring A represents a heterocycloalkylene selected from

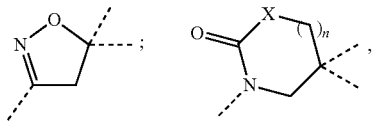

wherein X represents nitrogen or oxygen, and n represents the integer 0 or 1; and wherein in case X represents nitrogen, said nitrogen is unsubstituted;

and

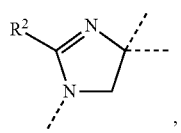

wherein R² represents hydrogen or methyl;
or a pharmaceutically acceptable salt thereof.

6. A compound according to claim 5, wherein ring B represents
unsubstituted $C_{4-7}$-cycloalkane-diyl;
$C_{4-7}$-cycloalkane-diyl wherein said $C_{4-7}$-cycloalkane-diyl is mono-substituted wherein the substituent is selected from $C_{1-4}$-alkyl; cyano; hydroxy; hydroxy-$C_{1-4}$-alkyl; and —NH—$R^{N11}$ wherein $R^{N11}$ represents $C_{1-6}$-alkyl, $C_{2-4}$-alkoxy, $C_{3-6}$-cycloalkyl, $C_{2-3}$-fluoroalkyl, —CO—$C_{1-4}$-alkyl, or —CO—$C_{1-4}$-alkoxy;
$C_{4-7}$-cycloalkane-diyl wherein said $C_{4-7}$-cycloalkane-diyl is di-substituted wherein the substituents are independently selected from $C_{1-4}$-alkyl and halogen;
4- to 7-membered heterocycloalkane-diyl wherein said heterocycloalkane-diyl contains one ring oxygen atom; or
4- to 7-membered heterocycloalkane-diyl wherein said heterocycloalkane-diyl contains one ring nitrogen atom, wherein said nitrogen atom is unsubstituted or mono-substituted with $C_{1-4}$-alkyl, —CO—$C_{1-4}$-alkoxy, or —CO—NH—$C_{1-4}$-alkyl; and wherein said 4- to 7-membered heterocycloalkane-diyl carries no further substituent in addition to said substituent on the ring nitrogen atom, or carries one further substituent on a ring carbon atom that is attached to said ring nitrogen atom wherein said substituent is oxo;
or a pharmaceutically acceptable salt thereof.

7. A compound according to claim 5, wherein ring B represents
cyclohexane-1,1-diyl or cycloheptane-1,1-diyl;
cyclohexane-1,1-diyl which is mono-substituted wherein the substituent is selected from $C_{1-4}$-alkyl; cyano; hydroxy; hydroxy-$C_{1-4}$-alkyl; and —NH—$R^{N11}$ wherein $R^{N11}$ represents cyclopropyl, $C_{2-3}$-fluoroalkyl, —CO—$C_{1-4}$-alkyl, or —CO—$C_{1-4}$-alkoxy;
cyclohexane-1,1-diyl which is di-substituted wherein the substituents are selected from $C_{1-4}$-alkyl and halogen;
tetrahydropyran-4,4-diyl;
piperidin-4,4-diyl, wherein the nitrogen atom of said piperidin-4,4-diyl is mono-substituted with —CO—$C_{1-4}$-alkoxy, or —CO—NH—$C_{1-4}$-alkyl; and wherein said piperidin-4,4-diyl carries no further substituent in addition to said substituent on the ring nitrogen atom; or
azepan-4,4-diyl, wherein the nitrogen atom of said azepan-4,4-diyl is unsubstituted or mono-substituted with $C_{1-4}$-alkyl, or —CO—$C_{1-4}$-alkoxy; and wherein said azepan-4,4-diyl carries no further substituent in addition to said substituent on the ring nitrogen atom, or carries one further substituent on a ring carbon atom that is attached to said ring nitrogen atom wherein said substituent is oxo;
or a pharmaceutically acceptable salt thereof.

8. A compound according to claim 5, wherein ring B represents
cyclohexane-1,1-diyl;
cyclohexane-1,1-diyl which is mono-substituted wherein the substituent is selected from cyano; hydroxy-$C_{1-4}$-alkyl; and —NH—$R^{N11}$ wherein $R^{N11}$ represents —CO—$C_{1-4}$-alkyl, or —CO—$C_{1-4}$-alkoxy;
cyclohexane-1,1-diyl which is di-substituted with fluoro; or
tetrahydropyran-4,4-diyl;
or a pharmaceutically acceptable salt thereof.

9. A compound according to claim 1, wherein

represents a spirocyclic fragment selected from the following groups:

A)

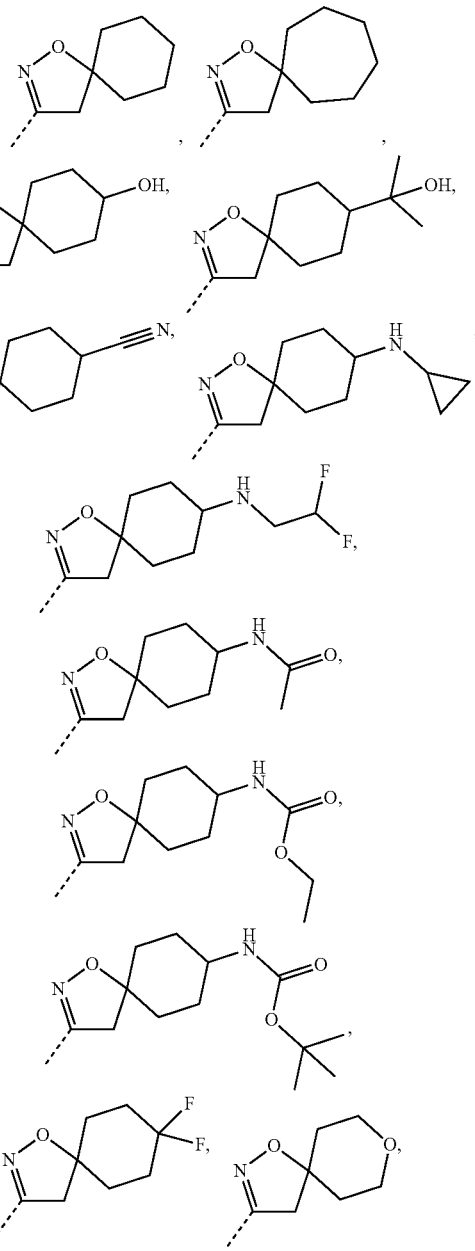

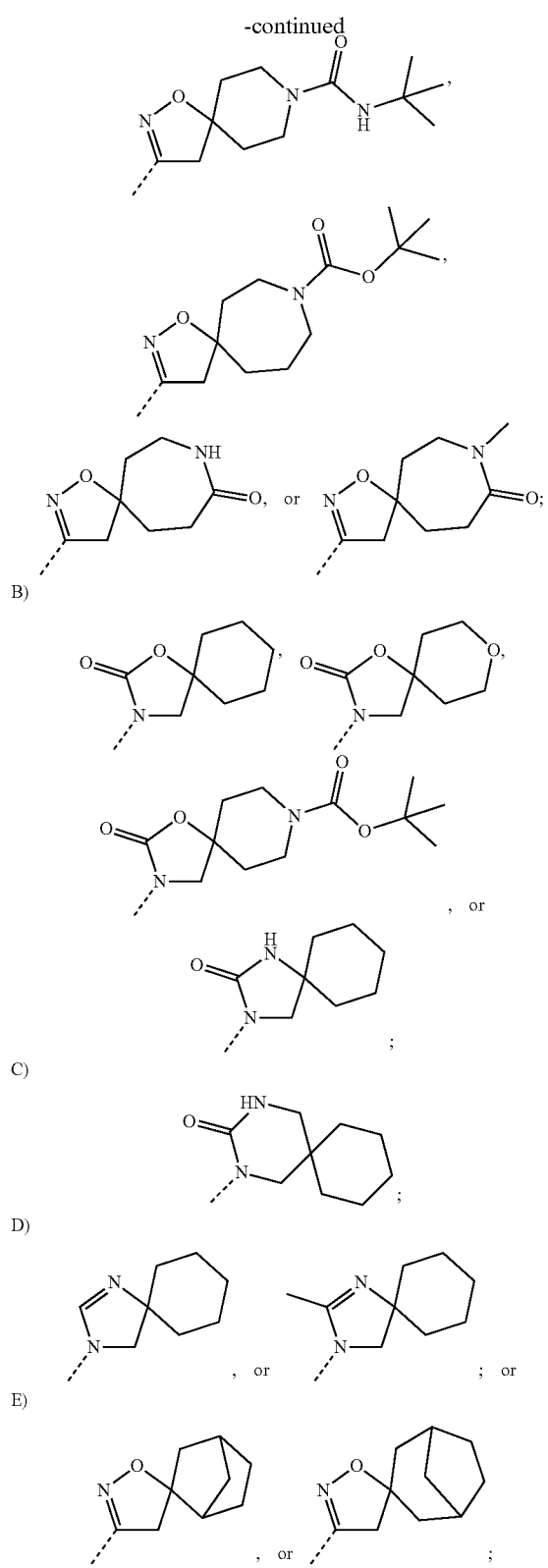

B)

C)

D)

E)

or a pharmaceutically acceptable salt thereof.

10. A compound according to claim 3, wherein $R^1$ represents methoxy;

or a pharmaceutically acceptable salt thereof.

11. A compound according to claim 10, wherein ring A represents a heterocycloalkylene selected from wherein X represents nitrogen or oxygen, and n represents the integer 0 or 1; and wherein in case X represents nitrogen, said nitrogen is unsubstituted;

and wherein $R^2$ represents hydrogen or methyl;

or a pharmaceutically acceptable salt thereof.

12. A compound according to claim 11, wherein ring B represents cyclohexane-1,1-diyl;

cyclohexane-1,1-diyl which is mono-substituted wherein the substituent is selected from cyano; hydroxy-$C_{1-4}$-alkyl; and —NH—$R^{N11}$ wherein $R^{N11}$ represents —CO—$C_{1-4}$-alkyl, or —CO—$C_{1-4}$-alkoxy;

cyclohexane-1,1-diyl which is di-substituted with fluoro; or tetrahydropyran-4,4-diyl;

or a pharmaceutically acceptable salt thereof.

13. A compound according to claim 10, wherein represents a spirocyclic fragment selected from the following groups:

A)

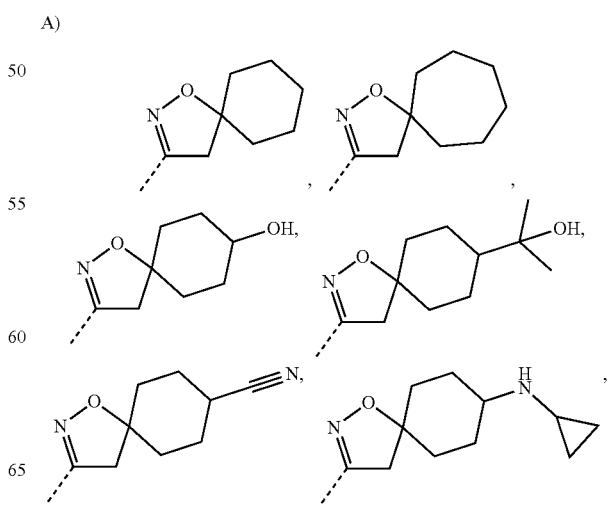

-continued

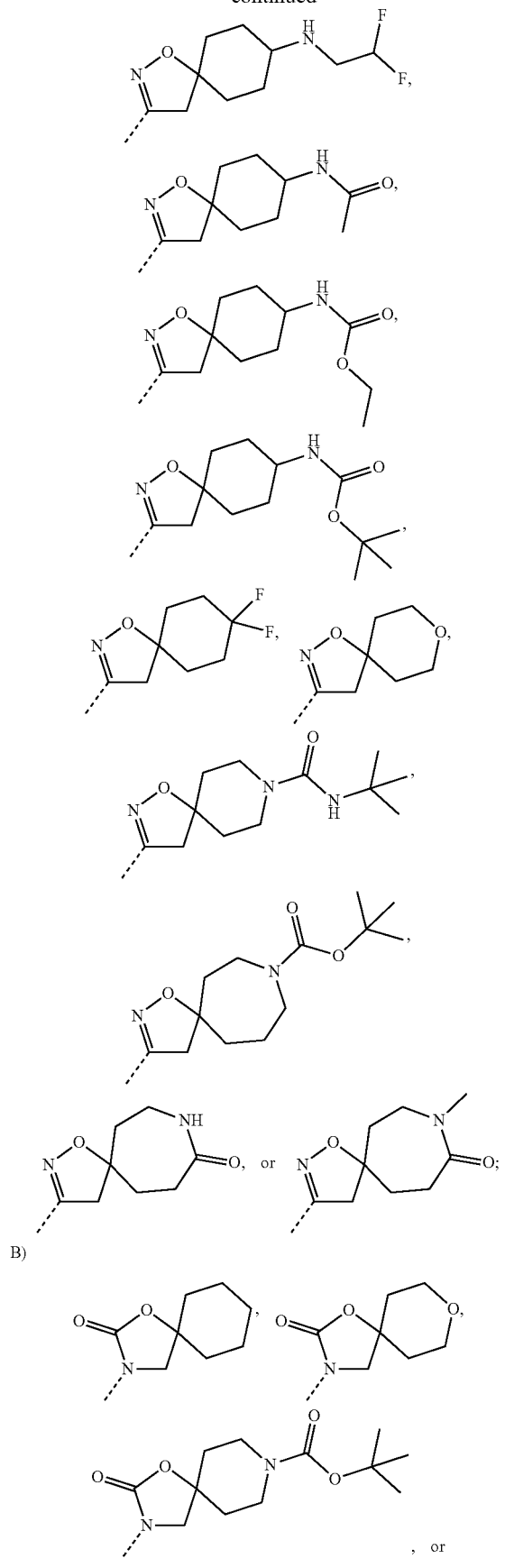

-continued

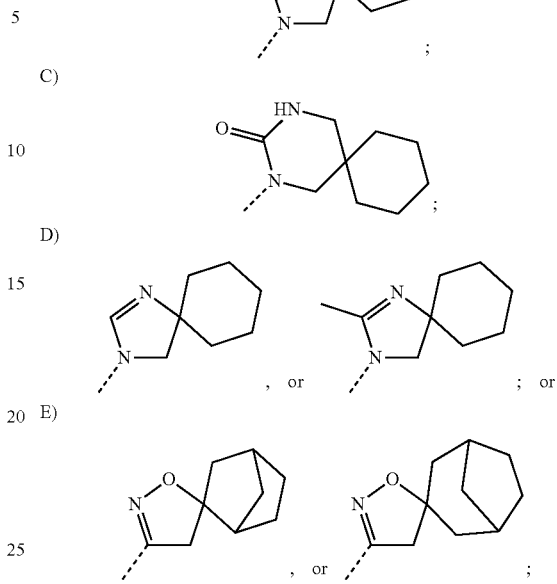

or a pharmaceutically acceptable salt thereof.

14. A pharmaceutical composition comprising a compound according to claim 1, or a pharmaceutically acceptable salt thereof, and a pharmaceutically acceptable carrier.

15. A method for the treatment of fibrosis of organs; liver diseases and disorders; cardiovascular diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; acute kidney injury and chronic kidney disease; interstitial lung diseases and disorders; and transplant rejection; comprising administering to a subject in a need thereof an effective amount of a compound as defined in claim 1, or of a pharmaceutically acceptable salt thereof.

16. A compound wherein said compound is:
(2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl acetate;
(2R,3R,4R,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-6-(hydroxymethyl)tetrahydro-2H-pyran-3,5-diol;
(2R,3R,4S,5R,6R)-2-((8,8-difluoro-1-oxa-2-azaspiro[4.5]dec-2-en-3-yl)methyl)-4-(4-(2,3-difluoro-4-methylph enyl)-1H-1,2,3-triazol-1-yl)-5-hydroxy-6-(hydroxymethyl)tetrahydro-2H-pyran-3-yl acetate;
(2R,3R,4R,5R,6R)-2-((8,8-difluoro-1-oxa-2-azaspiro[4.5]dec-2-en-3-yl)methyl)-4-(4-(2,3-difluoro-4-methylph enyl)-1H-1,2,3-triazol-1-yl)-6-(hydroxymethyl)tetrahydro-2H-pyran-3,5-diol;
(2R,3R,4R,5R,6R)-2-((1-oxa-2-azaspiro[4.5]dec-2-en-3-yl)methyl)-6-(hydroxymethyl)-4-(4-(3,4,5-trifluoroph enyl)-1H-1,2,3-triazol-1-yl)tetrahydro-2H-pyran-3,5-diol;

(2R,3R,4S,5R,6R)-6-((1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

tert-butyl (3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-yl)carbamate;

(2R,3R,4S,5R,6R)-6-((1-oxa-2-azaspiro[4.5]dec-2-en-3-yl)methyl)-2-(hydroxymethyl)-5-methoxy-4-(4-(2,3,4-trifluorophenyl)-1H-1,2,3-triazol-1-yl)tetrahydro-2H-pyran-3-ol;

(2R,3R,4S,5R,6R)-6-((1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

tert-butyl ((5r,8R)-3-(((2R,3R,4S,5R,6R)-5-hydroxy-6-(hydroxymethyl)-3-methoxy-4-(4-(3,4,5-trifluorophenyl)-1H-1,2, 3-triazol-1-yl)tetrahydro-2H-pyran-2-yl)methyl)-1-oxa-2-azaspiro[4.5]dec-2-en-8-yl)carbamate;

(2R,3R,4S,5R,6R)-6-((1-oxa-2-azaspiro[4.5]dec-2-en-3-yl)methyl)-4-(4-(4-bromo-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(4-chloro-3,5-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3-fluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3,5-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.5]dec-2-en-3-yl)methyl)-4-(4-(3-chloro-4,5-difluorophenyl)-1H-1,2,3-triazol-1-yl)-2-(hydroxymethyl)-5-methoxytetrahydro-2H-pyran-3-ol;

(2R,3R,4S,5R,6R)-6-((1,8-dioxa-2-azaspiro[4.5]dec-2-en-3-yl)methyl)-2-(hydroxymethyl)-5-methoxy-4-(4-(2, 3,4-trifluorophenyl)-1H-1,2,3-triazol-1-yl)tetrahydro-2H-pyran-3-ol;

(2R,3R,4S,5R,6R)-6-((1,8-dioxa-2-azaspiro[4.5]dec-2-en-3-yl)methyl)-4-(4-(2,3-difluoro-4-methylphenyl)-1H-1, 2,3-triazol-1-yl)-2-(hydroxymethyl)-5-methoxytetrahydro-2H-pyran-3-ol;

(2R,3R,4S,5R,6R)-6-((1,8-dioxa-2-azaspiro[4.5]dec-2-en-3-yl)methyl)-4-(4-(4-chloro-2,3-difluorophenyl)-1H-1,2,3-triazol-1-yl)-2-(hydroxymethyl)-5-methoxytetrahydro-2H-pyran-3-ol;

(2R,3R,4S,5R,6R)-6-((1-oxa-2-azaspiro[4.6]undec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(5s,8S)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-ene-8-carbonitrile;

tert-butyl ((5r,8R)-3-(((2R,3R,4S,5R,6R)-5-hydroxy-6-(hydroxymethyl)-3-methoxy-4-(4-(2,3,4-trifluorophenyl)-1H-1,2, 3-triazol-1-yl)tetrahydro-2H-pyran-2-yl)methyl)-1-oxa-2-azaspiro[4.5]dec-2-en-8-yl)carbamate;

tert-butyl ((5s,8S)-3-(((2R,3R,4S,5R,6R)-5-hydroxy-6-(hydroxymethyl)-3-methoxy-4-(4-(2,3,4-trifluorophenyl)-1H-1,2, 3-triazol-1-yl)tetrahydro-2H-pyran-2-yl)methyl)-1-oxa-2-azaspiro[4.5]dec-2-en-8-yl)carbamate;

tert-butyl ((5r,8R)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

tert-butyl ((5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

tert-butyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

tert-butyl ((5s,8S)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(2R,3R,4S,5R,6R)-2-(hydroxymethyl)-6-(((5r,8R)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-2-(hydroxymethyl)-6-(((5s,8S)-8-(2-hydroxypropan-2-yl)-1-oxa-2-azaspiro[4.5]dec-2-en-3-yl)methyl)-5-methoxy-4-(4-(2,3,4-trifluorophenyl)-1H-1,2,3-triazol-1-yl)tetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-((8-(2-hydroxypropan-2-yl)-1-oxa-2-azaspiro[4.5]dec-2-en-3-yl)methyl)-5-methoxytetrahydro-2H-pyran-3-ol;

(5s,8S)-3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-ene-8-carbonitrile;

(5r,8R)-3-(((2R,3R,4S,5R,6R)-4-(4-(2,3-difluoro-4-methylphenyl)-1H-1,2,3-triazol-1-yl)-5-hydroxy-6-(hydrox ymethyl)-3-methoxytetrahydro-2H-pyran-2-yl)methyl)-1-oxa-2-azaspiro[4.5]dec-2-ene-8-carbonitrile;

(5s,8S)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5r,8R)-3-(((2R,3R,4S,5R,6R)-5-hydroxy-6-(hydroxymethyl)-3-methoxy-4-(4-(2,3,4-trifluorophenyl)-1H-1,2,3-triazol-1-yl)tetrahydro-2H-pyran-2-yl)methyl)-1-oxa-2-azaspiro[4.5]dec-2-ene-8-carbonitrile;

(5s,8S)-3-(((2R,3R,4S,5R,6R)-4-(4-(4-chloro-2,3-difluorophenyl)-1H-1,2,3-triazol-1-yl)-5-hydroxy-6-(hydroxy methyl)-3-methoxytetrahydro-2H-pyran-2-yl)methyl)-1-oxa-2-azaspiro[4.5]dec-2-ene-8-carbonitrile;

(5r,8R)-3-(((2R,3R,4S,5R,6R)-4-(4-(4-chloro-2,3-difluorophenyl)-1H-1,2,3-triazol-1-yl)-5-hydroxy-6-(hydroxy methyl)-3-methoxytetrahydro-2H-pyran-2-yl)methyl)-1-oxa-2-azaspiro[4.5]dec-2-ene-8-carbonitrile;

(2R,3R,4S,5R,6R)-4-(4-(2,3-difluoro-4-methylphenyl)-1H-1,2,3-triazol-1-yl)-2-(hydroxymethyl)-6-(((5r,8R)-8-(2-hydroxypropan-2-yl)-1-oxa-2-azaspiro[4.5]dec-2-en-3-yl)methyl)-5-methoxytetrahydro-2H-pyran-3-ol;

(2R,3R,4S,5R,6R)-4-(4-(2,3-difluoro-4-methylphenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol;

(2R,3R,4S,5R,6R)-4-(4-(4-chloro-2,3-difluorophenyl)-1H-1,2,3-triazol-1-yl)-2-(hydroxymethyl)-6-(((5s,8S)-8-(2-hydroxypropan-2-yl)-1-oxa-2-azaspiro[4.5]dec-2-en-3-yl)methyl)-5-methoxytetrahydro-2H-pyran-3-ol;

3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-one;

(2R,3R,4S,5R,6R)-6-((1-oxa-2-azaspiro[4.5]dec-2-en-3-yl)methyl)-5-(2,2-difluoroethoxy)-2-(hydroxymethyl)-4-(4-(3,4,5-trifluorophenyl)-1H-1,2,3-triazol-1-yl)tetrahydro-2H-pyran-3-ol;

methyl 2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetate;

(2R,3R,4S,5R,6R)-6-((1-oxa-2-azaspiro[4.5]dec-2-en-3-yl)methyl)-5-ethoxy-2-(hydroxymethyl)-4-(4-(3,4,5-tr ifluorophenyl)-1H-1,2,3-triazol-1-yl)tetrahydro-2H-pyran-3-ol;

2-(((2R,3R,4S,5R,6R)-2-((1-oxa-2-azaspiro[4.5]dec-2-en-3-yl)methyl)-5-hydroxy-6-(hydroxymethyl)-4-(4-(3, 4,5-trifluorophenyl)-1H-1,2,3-triazol-1-yl)tetrahydro-2H-pyran-3-yl)oxy)-N-methylacetamide;

2-(((2R,3R,4S,5R,6R)-2-((1-oxa-2-azaspiro[4.5]dec-2-en-3-yl)methyl)-5-hydroxy-6-(hydroxymethyl)-4-(4-(3, 4,5-trifluorophenyl)-1H-1,2,3-triazol-1-yl)tetrahydro-2H-pyran-3-yl)oxy)-1-morpholinoethan-1-one;

methyl 2-(((2R,3R,4S,5R,6R)-2-((8,8-difluoro-1-oxa-2-azaspiro[4.5]dec-2-en-3-yl)methyl)-4-(4-(2,3-difluoro-4-meth ylphenyl)-1H-1,2,3-triazol-1-yl)-5-hydroxy-6-(hydroxymethyl)tetrahydro-2H-pyran-3-yl)oxy) acetate;

(2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl carbamate;

(2R,3R,4S,5R,6R)-4-(4-(2,3-difluoro-4-methylphenyl)-1H-1,2,3-triazol-1-yl)-6-(((5r,8R)-8-((2,2-difluoroethyl) amino)-1-oxa-2-azaspiro[4.5]dec-2-en-3-yl)methyl)-2-(hydroxymethyl)-5-methoxytetrahydro-2H-pyran-3-ol;

tert-butyl (RS)-3-(((2R,3R,4S,5R,6R)-4-(4-(2,3-difluoro-4-methylphenyl)-1H-1,2,3-triazol-1-yl)-5-hydroxy-6-(hydroxym ethyl)-3-methoxytetrahydro-2H-pyran-2-yl)methyl)-1-oxa-2,8-diazaspiro[4.6]undec-2-ene-8-carboxylate;

(RS)-3-(((2R,3R,4S,5R,6R)-4-(4-(2,3-difluoro-4-methylphenyl)-1H-1,2,3-triazol-1-yl)-5-hydroxy-6-(hydroxym ethyl)-3-methoxytetrahydro-2H-pyran-2-yl)methyl)-1-oxa-2,8-diazaspiro[4.6]undec-2-en-9-one;

(RS)-3-(((2R,3R,4S,5R,6R)-4-(4-(2,3-difluoro-4-methylphenyl)-1H-1,2,3-triazol-1-yl)-5-hydroxy-6-(hydroxym ethyl)-3-methoxytetrahydro-2H-pyran-2-yl)methyl)-8-methyl-1-oxa-2,8-diazaspiro[4.6]undec-2-en-9-one;

(5RS,8S)-7-(tert-butoxycarbonyl)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2,7-diazaspiro[4.4]no n-2-ene-8-carboxylic acid;

3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol;

(5r,8R)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2-azaspiro[4.5]dec-2-en-8-ol;

N-((5r,8R)-3-(((2R,3R,4S,5R,6R)-5-hydroxy-6-(hydroxymethyl)-3-methoxy-4-(4-(3,4,5-trifluorophenyl)-1H-1, 2,3-triazol-1-yl)tetrahydro-2H-pyran-2-yl)methyl)-1-oxa-2-azaspiro[4.5]dec-2-en-8-yl) acetamide;

N-((5r,8R)-3-(((2R,3R,4S,5R,6R)-4-(4-(2,3-difluoro-4-methylphenyl)-1H-1,2,3-triazol-1-yl)-5-hydroxy-6-(hydr oxymethyl)-3-methoxytetrahydro-2H-pyran-2-yl)methyl)-1-oxa-2-azaspiro[4.5]dec-2-en-8-yl) acetamide;

N-((5r,8R)-3-(((2R,3R,4S,5R,6R)-4-(4-(4-chloro-2,3-difluorophenyl)-1H-1,2,3-triazol-1-yl)-5-hydroxy-6-(hydr oxymethyl)-3-methoxytetrahydro-2H-pyran-2-yl)methyl)-1-oxa-2-azaspiro[4.5]dec-2-en-8-yl) acetamide;

N-((5r,8R)-3-(((2R,3R,4S,5R,6R)-5-hydroxy-6-(hydroxymethyl)-3-methoxy-4-(4-(2,3,4-trifluorophenyl)-1H-1, 2,3-triazol-1-yl)tetrahydro-2H-pyran-2-yl)methyl)-1-oxa-2-azaspiro[4.5]dec-2-en-8-yl) acetamide;

ethyl ((5r,8R)-3-(((2R,3R,4S,5R,6R)-4-(4-(2,3-difluoro-4-methylphenyl)-1H-1,2,3-triazol-1-yl)-5-hydroxy-6-(hydrox ymethyl)-3-methoxytetrahydro-2H-pyran-2-yl)methyl)-1-oxa-2-azaspiro[4.5]dec-2-en-8-yl) carbamate;

ethyl ((5r,8R)-3-(((2R,3R,4S,5R,6R)-5-hydroxy-6-(hydroxymethyl)-3-methoxy-4-(4-(2,3,4-trifluorophenyl)-1H-1,2, 3-triazol-1-yl)tetrahydro-2H-pyran-2-yl)methyl)-1-oxa-2-azaspiro[4.5]dec-2-en-8-yl) carbamate;

ethyl ((5r,8R)-3-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-1-oxa-2-azaspiro[4.5]dec-2-en-8-yl)carbamate;

(2R,3R,4S,5R,6R)-2-(hydroxymethyl)-6-((((5r,8R)-8-(isopropylamino)-1-oxa-2-azaspiro[4.5]dec-2-en-3-yl)methyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-((8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-2-(hydroxymethyl)-5-methoxy-6-((8-((2,2,2-trifluoroethyl)amino)-1-oxa-2-azaspiro[4.5]dec-2-en-3-yl)methyl)-4-(4-(3,4,5-trifluorophenyl)-1H-1,2,3-triazol-1-yl)tetrahydro-2H-pyran-3-ol;

(2R,3R,4S,5R,6R)-6-(((5r,8R)-8-((2,2-difluoroethyl)amino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

(2R,3R,4S,5R,6R)-6-(((5r,8R)-8-(cyclopropylamino)-1-oxa-2-azaspiro[4.5]dec-2-en-3-yl)methyl)-2-(hydroxymethyl)-5-methoxy-4-(4-(3,4,5-trifluorophenyl)-1H-1,2,3-triazol-1-yl)tetrahydro-2H-pyran-3-ol;

2-(((2R,3R,4S,5R,6R)-2-((1,8-dioxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid;

2-(((2R,3R,4S,5R,6R)-2-((1-oxa-2-azaspiro[4.5]dec-2-en-3-yl)methyl)-4-(4-(2,3-difluoro-4-methylphenyl)-1H-1,2,3-triazol-1-yl)-5-hydroxy-6-(hydroxymethyl)tetrahydro-2H-pyran-3-yl)oxy)acetic acid;

2-(((2R,3R,4S,5R,6R)-2-((1-oxa-2-azaspiro[4.5]dec-2-en-3-yl)methyl)-5-hydroxy-6-(hydroxymethyl)-4-(4-(3,4,5-trifluorophenyl)-1H-1,2,3-triazol-1-yl)tetrahydro-2H-pyran-3-yl)oxy)acetic acid;

(2R,3R,4S,5R,6R)-6-((8,8-difluoro-1-oxa-2-azaspiro[4.5]dec-2-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

N-(tert-butyl)-3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-ene-8-carboxamide;

1-(3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-1-oxa-2,8-diazaspiro[4.5]dec-2-en-8-yl)ethan-1-one;

tert-butyl 3-(((2R,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)methyl)-2-oxo-1-oxa-3,8-diazaspiro[4.5]decane-8-carboxylate;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1-oxa-3-azaspiro[4.5]decan-2-one;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,8-dioxa-3-azaspiro[4.5]decan-2-one;

3-(((2R,3R,4S,5R,6R)-4-(4-(2,3-difluoro-4-methylphenyl)-1H-1,2,3-triazol-1-yl)-5-hydroxy-6-(hydroxymethyl)-3-methoxytetrahydro-2H-pyran-2-yl)methyl)-1,3-diazaspiro[4.5]decan-2-one;

2-(((2R,3R,4S,5R,6R)-4-(4-(4-chloro-2,3-difluorophenyl)-1H-1,2,3-triazol-1-yl)-5-hydroxy-6-(hydroxymethyl)-3-methoxytetrahydro-2H-pyran-2-yl)methyl)-2,4-diazaspiro[5.5]undecan-3-one;

(2R,3R,4S,5R,6R)-4-(4-(2,3-difluoro-4-methylphenyl)-1H-1,2,3-triazol-1-yl)-2-(hydroxymethyl)-5-methoxy-6-((2-methyl-1,3-diazaspiro[4.5]dec-1-en-3-yl)methyl)tetrahydro-2H-pyran-3-ol; or (2R,3R,4S,5R,6R)-6-((1,3-diazaspiro[4.5]dec-1-en-3-yl)methyl)-4-(4-(2,3-difluoro-4-methylphenyl)-1H-1,2,3-triazol-1-yl)-2-(hydroxymethyl)-5-methoxytetrahydro-2H-pyran-3-ol;

or a pharmaceutically acceptable salt thereof.

17. A pharmaceutical composition comprising a compound according to claim 16, or a pharmaceutically acceptable salt thereof, and a pharmaceutically acceptable carrier.

18. A method for the or treatment of fibrosis of an indication selected from organs; liver diseases and disorders; cardiovascular diseases and disorders; cell proliferative diseases and cancers; inflammatory and autoimmune diseases and disorders; gastrointestinal tract diseases and disorders; pancreatic diseases and disorders; abnormal angiogenesis-associated diseases and disorders; brain-associated diseases and disorders; neuropathic pain and peripheral neuropathy; ocular diseases and disorders; acute kidney injury and chronic kidney disease; interstitial lung diseases and disorders; or transplant rejection; comprising administering to a subject in a need thereof an effective amount of a compound as defined in claim 10, or of a pharmaceutically acceptable salt thereof.

* * * * *